United States Patent
Schwartz et al.

(10) Patent No.: US 8,993,117 B2
(45) Date of Patent: Mar. 31, 2015

(54) DEVICES WITH MULTIPLE SURFACE FUNCTIONALITY

(75) Inventors: Jeffrey Schwartz, Princeton, NJ (US); Ellen S. Gawalt, Pittsburgh, PA (US); Michael J. Avaltroni, Staten Island, NY (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 13/349,367

(22) Filed: Jan. 12, 2012

(65) Prior Publication Data

US 2012/0121661 A1    May 17, 2012

Related U.S. Application Data

(63) Continuation of application No. 11/330,814, filed on Jan. 12, 2006, now abandoned.

(60) Provisional application No. 60/643,647, filed on Jan. 13, 2005, provisional application No. 60/643,648, filed on Jan. 13, 2005, provisional application No. 60/684,159, filed on May 25, 2005, provisional application No. 60/699,498, filed on Jul. 15, 2005, provisional application No. 60/707,525, filed on Aug. 12, 2005.

(51) Int. Cl.
| | | |
|---|---|---|
| *B32B 15/04* | (2006.01) | |
| *A61F 2/28* | (2006.01) | |
| *A61F 2/02* | (2006.01) | |
| *A61L 27/32* | (2006.01) | |
| *A61L 29/10* | (2006.01) | |
| *A61L 31/08* | (2006.01) | |
| *B05D 1/18* | (2006.01) | |
| *B82Y 30/00* | (2011.01) | |
| *B82Y 40/00* | (2011.01) | |
| *C03C 17/00* | (2006.01) | |
| *C03C 17/23* | (2006.01) | |
| *C23C 14/06* | (2006.01) | |
| *C23C 22/02* | (2006.01) | |
| *C23C 22/48* | (2006.01) | |

(52) U.S. Cl.
CPC .............. *A61L 27/32* (2013.01); *A61L 29/106* (2013.01); *A61L 31/086* (2013.01); *B05D 1/185* (2013.01); *B82Y 30/00* (2013.01); *B82Y 40/00* (2013.01); *C03C 17/001* (2013.01); *C03C 17/23* (2013.01); *C23C 14/06* (2013.01); *C23C 22/02* (2013.01); *C23C 22/48* (2013.01)
USPC ...... 428/624; 428/632; 623/16.11; 623/23.76

(58) Field of Classification Search
None
See application file for complete search history.

(56) References Cited

U.S. PATENT DOCUMENTS

| | | |
|---|---|---|
| 3,224,908 A | 12/1965 | Duch et al. |
| 3,293,088 A | 12/1966 | Herbst et al. |
| 3,634,146 A | 1/1972 | Wystrach et al. |
| 3,772,355 A | 11/1973 | Merz |
| 4,403,941 A | 9/1983 | Okiura et al. |
| 4,578,156 A | 3/1986 | Plazter |
| 4,788,176 A | 11/1988 | Wieserman et al. |
| 4,830,993 A | 5/1989 | Legrand et al. |
| 4,909,846 A | 3/1990 | Barfurth et al. |
| 4,929,589 A | 5/1990 | Martin et al. |
| 4,962,073 A | 10/1990 | Martin et al. |
| 4,994,429 A | 2/1991 | Wieserman et al. |
| 5,032,237 A | 7/1991 | Wieserman et al. |
| 5,102,507 A | 4/1992 | Wieserman et al. |
| 5,103,550 A | 4/1992 | Wefers et al. |
| 5,126,210 A | 6/1992 | Wieserman et al. |
| 5,139,601 A | 8/1992 | Holmes-Farley et al. |
| 5,185,208 A | 2/1993 | Yamashita et al. |
| 5,231,151 A | 7/1993 | Spencer et al. |
| 5,238,715 A | 8/1993 | Wefers et al. |
| 5,277,788 A | 1/1994 | Nitowski et al. |
| 5,279,720 A | 1/1994 | Divigalpitiya |
| 5,286,571 A | 2/1994 | Mirkin et al. |
| 5,397,642 A | 3/1995 | Li et al. |

(Continued)

FOREIGN PATENT DOCUMENTS

| | | |
|---|---|---|
| DE | 10040993 B4 | 7/2007 |
| JP | 2018463 A | 1/1990 |

(Continued)

OTHER PUBLICATIONS

Definition of "coordinate bond", The Free Dictionary, http://www.thefreedictionary.com/coordinate+bond, printed Jul. 28, 2013.*
Miller et al., The Importance of Liquid Kinetic Basicity on the Preparation of Surface Supported Zirconium Complexes by Proton Transfer fromHydroxylated Aluminium on Silicon J.Am.Chem Soc., 115, 8239-8247 (1993).
Galiardi et al., Pre-Resonance Raman Characterisation of Metal-Organic Films from Titanium Alkoxide Carboxylate Complexes, Mat. Res. Soc. Syp. Proc., 180,801-805 (1990).

(Continued)

*Primary Examiner* — Adam Krupicka
(74) *Attorney, Agent, or Firm* — Fox Rothschild LLP; Peter J. Butch, III; Robert N. Henrie, II

(57) ABSTRACT

Phosphorus-based coatings having a plurality of phosphate moieties, a plurality of phosphonate moieties, or both, covalently bonded to an oxide surface of an implantable substrate exhibiting one or more of the following characteristics: (a) the surface phosphorus-containing group density of the coated regions of the substrate is at least about 0.1 nmol/cm$^2$; (b) the phosphorus-based coating has a thickness of less than about 10 nm; or (c) the surface phosphorus-containing group density of the coated regions of the substrate is equal to or greater than the surface hydroxyl group density of the oxide surface of the substrate. Implantable devices embodying the coated substrates are also disclosed.

29 Claims, 11 Drawing Sheets

(56) References Cited

U.S. PATENT DOCUMENTS

| | | | |
|---|---|---|---|
| 5,463,804 | A | 11/1995 | McCleary et al. |
| 5,728,203 | A | 3/1998 | Vorse et al. |
| 5,767,032 | A | 6/1998 | Hokkanen et al. |
| 6,020,047 | A | 2/2000 | Everhart |
| 6,030,710 | A | 2/2000 | Nitowski et al. |
| 6,066,403 | A | 5/2000 | Sherwood et al. |
| 6,129,928 | A | 10/2000 | Sarangapani et al. |
| 6,146,767 | A | 11/2000 | Schwartz |
| 6,167,609 | B1 | 1/2001 | Marinelli et al. |
| 6,225,239 | B1 | 5/2001 | Ohno et al. |
| 6,380,101 | B1 | 4/2002 | Breen et al. |
| 6,433,359 | B1 | 8/2002 | Kelley et al. |
| 6,436,475 | B1 | 8/2002 | Adler et al. |
| 6,488,990 | B1 | 12/2002 | Wetterer et al. |
| 6,645,644 | B1 | 11/2003 | Schwartz et al. |
| 6,824,882 | B2 | 11/2004 | Boardman et al. |
| 6,866,791 | B1 | 3/2005 | Breen et al. |
| 6,887,332 | B1 | 5/2005 | Kagan et al. |
| 7,090,496 | B2 | 8/2006 | Descouts et al. |
| 7,396,594 | B2 | 7/2008 | Schwartz et al. |
| 7,507,483 | B2 | 3/2009 | Schwartz et al. |
| 7,569,285 | B2 | 8/2009 | Schwartz et al. |
| 2002/0130441 | A1 | 9/2002 | Robinson et al. |
| 2003/0186914 | A1 | 10/2003 | Hofer et al. |
| 2004/0023048 | A1* | 2/2004 | Schwartz et al. .......... 428/472.1 |
| 2004/0049287 | A1 | 3/2004 | Descouts et al. |
| 2004/0054422 | A1 | 3/2004 | Descouts et al. |
| 2005/0031910 | A1 | 2/2005 | Schwartz et al. |

FOREIGN PATENT DOCUMENTS

| | | |
|---|---|---|
| JP | 5224448 A | 9/1993 |
| WO | 0220873 A2 | 3/2002 |
| WO | 02/40074 A1 | 5/2002 |
| WO | 0240073 A1 | 5/2002 |
| WO | 0240075 A1 | 5/2002 |
| WO | 2005000575 A1 | 1/2005 |

OTHER PUBLICATIONS

Labimis et al. Orthogonal Self-Assembled Mono-Layers: Alkanethiols on Gold and Alkane Carboxylic Acids on Alumina, Science, 245,845 (1989).

Gao et al.., Self Assembled Monlayers of Alkylphosohoric Acids on Metal Oxides, Langmuir, 12, 6429-6435 (1996).

Fang et al., XPS, AES and Raman Studies of Antitarnish Film on Tin, Corrosion, 47, 169-173 (1991).

Strivastava, Characterization of adhesive bonded lap joints ofC/C—SiC composite and Ti—6Al—4V alloy under varying conditions, Intl. J. Adhesion and Adhesives, 23, 59-67 (2003).

Seto, Stabilization of Self-Assembled Monolayers on Native Oxides, Thesis No. 6066, Available Princeton University Library System on Oct. 17, 1995.

Gawalt et al.,Enhanced Bonding of Alkanephosphonic acids to Oxidized Titanium Using Surface-Bound Alkoxyzirconium Complex Interfaces,Langmuir—The ACS Journal of Surfaces and Colloids,vol. 15, No. 26, pp. 8929-8933, Oct. 7, 1999.

Lee et al., "Adsorption of Ordered Zirconium Phosphonate Multilayer Films on Silicon and Gold Surfaces," J. Phys. Chem (1988); vol. 92, pp. 2597-2601.

Folkers et al., "Self-Assembled Monolayers of Long-Chain Hydroxamic Acids on the Native Oxides of Metals," Langmuir (1995); vol. 11, pp. 813-824.

Brovelli et al., "Highly Oriented, Self-Assembled Alkanephophate Monolayers on Tantalum(V) Oxide Surfaces," Langmuir (1999); vol. 15, pp. 4324-4327.

Gawalt et al., "Bonding Organics to Ti Alloys: Facilitating Human Osteoblast Attachment and Spreading on Surgical Implant Materials," Langmuir (2003); vol. 19, pp. 200-204.

Gawalt et al., "Additionas and Corrections," Langmuir (2003); vol. 19, pp. 7147.

Helmy et al., "Self-Assembled Monolayers Supported on TiP2: Comparison of C18H31SiX3(X=H,Cl,0CH3), C18H37Si (CH3) and C18H37Po(OH)2," Langmuir (2002); vol. 18, pp. 8927-8928.

Marcinko et al., "Polymeric Materials," Science and Engineering (2003); vol. 89, p. 493.

Neves et al., "Spread Coating of OPA on Mica: From Multilayers of Self-Assembled Monolayers," Langmuir (2001); vol. 17, pp. 8193-8198.

Kelley et al., "High-Performance OTFTs Using Surface-Modified Alumina Dielectrics," J. Phys. Chem. B. (2003); vol. 107, pp. 5877-5881.

Neves et al., "Thermal Stability Study of self-assembled Monolayers on mica," Langmuir (2000); vol. 16, pp. 2409-2412.

Gawalt et al., "Self-Assembly and Bonding of Alkanephophonic Acids on the Native Oxide Surface of Titanium," Langmuir (2001); vol. 17, pp. 5736-5738.

* cited by examiner

DEVICES WITH MULTIPLE SURFACE FUNCTIONALITY

CROSS-REFERENCE TO RELATED APPLICATIONS

The present application is a Continuation of U.S. patent application Ser. No. 11/330,814 filed Jan. 12, 2006 which claims priority to U.S. Provisional Application No. 60/643,647 filed Jan. 13, 2005; U.S. Provisional Application No. 60/643,648 filed Jan. 13, 2005; U.S. Application No. 60/684,159 filed May 25, 2005; U.S. Application No. 60/699,498 filed Jul. 15, 2005; and, U.S. Application No. 60/707,525 filed Aug. 12, 2005, the entire contents of all of which are hereby incorporated by reference.

STATEMENT REGARDING FEDERALLY FUNDED RESEARCH

This invention was made with government support under Grant CHE-0310178 awarded by the National Science Foundation and Grant No. CA-045339 awarded by the National Institutes of Health. The U.S. government has certain rights in this invention.

FIELD OF THE INVENTION

The present invention relates to the provision of a medical device with one or more surface coatings covalently bonded to the oxide surface of one or more regions of the device to create different desirable surface properties on each region of the device surface. The present invention also relates to the provision of an adherent, self-assembled, phosphorous acid-based coating on an oxide surface, both as a coating layer for the surface and as an interface between the oxide surface and overlaying layers. Although the present application is illustrated below with the provision of orthopedic devices with multiple surface functionality derived from surface-bonded, organic acid-based mono-layers, it will be appreciated that the methods and devices of the present invention provided thereby have much broader applicability.

BACKGROUND OF THE INVENTION

Implantable medical devices, whether partially or completely implanted in the body, are frequently exposed to multiple types of physiological environments. It is frequently desirable for a device to exhibit different properties or biological functionality on different regions of the device surface depending on the physiological environment. Examples of specific functions that may be desirable for medical implant surfaces include:

Example 1—Cell Specific Adhesion and Attraction: It is frequently desirable to promote the adhesion of specific cells to surfaces. For example, for orthopedic implants and dental, it is desirable to specifically attract osteoblasts to a surface. For devices in contact with arterial walls, such as stents, it may be desirable to promote adhesion of specific endothelial cells to the outer wall of the stent to promote the arterial wall to heal and incorporate the stent.

Example 2—Non-Adhesion: It is frequently desirable to prevent adhesion of cells, proteins or other biomolecules to certain surfaces of medical implants. For example, implant surfaces with long term exposure to blood may generate thrombus. Inflammatory cells may also adhere to and proliferate on implant surfaces leading to increased inflammation and decreased healing rates. Adherence of thrombus and inflammatory cells can be minimized by a non-adherent surface.

Example 3—Anti-Corrosion: When exposed to physiological conditions, the surface of a metal implant corrodes and leaches metal ions into the body. Some patients exhibit heightened sensitivity or allergic response to certain metal alloys. For example, some patients exhibit nickel sensitivity. Metal sensitivity may lead to implant rejection and require explantation. Other metal ions, such as chromium, may have long term toxicity. It would be desirable to design a coated medical device that retains its medical functionality, but that exhibits significantly lower leaching of metal ions.

Example 4—Anti-infection: Infection presents a serious concern for implants. It would be desirable to covalently attach antibiotics, anti-microbial agents or agents that disrupt microbial pathogenesis such as anti-quorum sensing agents to regions of an implant.

Example 5—Anti-inflammatory: Implantation or deployment of medical devices frequently causes injury at the site of deployment/implantation. For example, balloon expandable stents injure the arterial wall when deployed resulting in inflammation that causes partial or complete restenosis of the artery. Similarly with orthopedic implants, trauma and inflammation from implantation results in long healing times. It would be desirable to provide an anti-inflammatory coating on portions of an implant.

Creating a stable bond between bone tissue and the surface of metallic bone implants is a research topic of considerable interest. Poor bonding with the interface between the metallic surface of the implant and the bone tissue leads to low mechanical strength of the bone-to-implant junction and the possibility of subsequent implant failure.

Titanium and titanium alloys are used extensively as dental and orthopedic implants. Currently, there is no effective way to obtain strong attachment of incipient bone with the implant material at the interface between the surfaces of the two materials in order to "stabilize" the implant.

An important goal for interface optimization is to use species which are biocompatible and which enable bone mineralization at the interface following implantation. Bone tissue is a combination of protein and mineral content, with the mineral content being in the form of hydroxyapatite.

The problem of interface synthesis is often approached from the prospective of high temperature methods, including using plasma or laser-induced coating techniques. However, these methods engender problems of implant heating and surface coverage. For example, calcium phosphate deposition at high temperatures can give rise to ion migration. Plasma-induced phosphate coating of a titanium substrate gives surface hydroxyapatite as well as surface calcium phosphate, titanates and zirconates. Therefore, control of surface stoichiometry can be problematic, and defects at the interface may translate into poor mechanical strength.

The use of intermediate layers, for example of zirconium dioxide, to enhance hydroxyapatite adhesion and interface mechanical strength has been explored with success. However, a practical limitation involving laser or plasma deposition is that it is hard to obtain comprehensive coverage on a titanium implant of complex 3-dimensional structure. The zirconium dioxide interface formed at high temperatures is of low surface area and maintains few, if any, reactive functional groups for further surface modification chemistry.

Solution-phase surface processing does not suffer from the practical limitations of surface coverage that can be attendant with plasma or laser-based deposition methods, and procedures involving formation of hydroxyapatite from solution, often using sol-gel type processing, have been accomplished. Elegant methodologies have been developed in which graded interfaces have been prepared, extending from the pure implant metal to the biomaterial at the outer extremity by way of silicates. However, while solution-based procedures are inexpensive and give rise to materials resistant to dissolution by bodily fluids, adhesion of the hydroxyapatite to the implant metal is less strong than is observed when deposition is accomplished by plasma spraying techniques.

The deficiency of these solution approaches may lie in the nature of the native oxide surface of titanium materials. Exposure of a clean surface of titanium materials to oxygen results in the spontaneous formation of surface titanium oxides (native oxide). The exact chemical stoichiometry and structure of these oxides varies from material to material, and with depth in the oxide layer, with environmental variables, and with the processing history of the material. The oxide layer may be stoichiometric, super-stoichiometric, or sub-stoichiometric with respect to $TiO_2$, a stable oxide of titanium. Generally, the uppermost layer of the native oxides comprises some form of $TiO_2$. It may be crystalline, but if crystalline, it is generally disordered. Typically, many different phases exist within the oxide layer between the metal and the ambient environment. Generally, the uppermost layer of oxide includes widely dispersed hydroxyl functional groups bonded to a titanium atom. The surface forms spontaneously by exposing the metal or alloy to the ambient environment, and is alternatively described as the "native oxide surface" of a titanium material.

As described in co-pending U.S. patent application Ser. No. 10/701,591, filed Nov. 4, 2003, Ser. No. 10/405,557, filed Apr. 1, 2003, and Ser. No. 10/179,743, filed Jun. 24, 2002, each of which is incorporated herein by reference in their entirety, and as described in U.S. Pat. No. 6,433,359 to Kelley et al., it is known that a phosphorous acid can be used to provide a layer on an oxide surface. For example, the use of phosphonic acid species on implantable materials has been disclosed by Descouts et al. (U.S. application Ser. No. 10/432,025), which is incorporated herein by reference in its entirety. But these phosphonic acid species fail to strongly adhere to the implant because they are not covalently bonded via heating. In addition, Descouts does not disclose the preparation of different surface treatments on the same implant.

The inventors have recognized the need for the provision of coated medical devices with different desirable surface properties and coatings which have an improved degree of organization and/or improved adhesion strength and/or which can be applied to surfaces over a large area, particularly when the coating is to be applied in a pattern.

SUMMARY OF INVENTION

In one aspect, the present invention provides a medical device or an implantable device with one or more surface coatings covalently bonded to an oxide surface of one or more regions of the device to create different desirable surface properties on each region of the device surface. The coated medical device may be produced from an implantable substrate.

In another aspect, the present invention provides a medical device or an implantable device comprising at least one surface to which is covalently bonded at least one species of phosphonic acid. The phosphonic acid may be terminated such that it may be further derivatized to provide clinically desirable functionality or the phosphonic acid species may itself provide the clinically desirable functionality. Clinically desirable functionality includes cell specific adhesion, cellular non-adhesion, osteoconduction, anti-thrombogenicity, anti-inflammation, anti-corrosion, anti-infection, infection prevention, wear resistance, lubrication, and ion blocking.

In one embodiment of the invention, an implantable device is provided wherein at least a portion of an oxide surface of the device is covalently bonded to a phosphorus-based coating comprising a plurality of phosphate moieties, a plurality of phosphonate moieties, or both. The coated regions of the implantable device can exhibit a surface phosphorus-containing group density of at least about $0.1$ $nmol/cm^2$; can exhibit a surface phosphorus-containing group density equal to or greater than the surface hydroxyl group density of the oxide surface of the implantable device; and the phosphorus-based coating can have a thickness of less than about 10 nm.

Still another aspect of the invention relates to a phosphorus-based coating comprising a plurality of phosphate moieties, a plurality of phosphonate moieties, or both, covalently bonded to an oxide surface of an implantable substrate. The coated regions of the implantable substrate can exhibit a surface phosphorus-containing group density of at least about $0.1$ $nmol/cm^2$; can exhibit a surface phosphorus-containing group density equal to or greater than the surface hydroxyl group density of the oxide surface of the implantable substrate; and the phosphorus-based coating can have a thickness of less than about 100 nm.

In one embodiment, the surface phosphorus-containing group density of the coated regions of the implantable substrate is at least about $0.1$ $nmol/cm^2$; the surface phosphorus-containing group density is equal to or greater than the surface hydroxyl group density of the oxide surface of the implantable substrate; and the phosphorus-based coating has a thickness of less than about 10 nm.

In another embodiment, the surface phosphorus-containing group density of the coated regions of the implantable substrate is at least about $0.25$ $nmol/cm^2$; the phosphorus-based coating comprises a surface phosphorus-containing group density of at least about 1.3 times the surface hydroxyl group density of the oxide surface of the implantable substrate; and the phosphorus-based coating has a thickness of less than about 5 nm.

In another embodiment, the phosphorus-based coating can have a first, inner surface and a second, outer surface, the first, inner surface being defined by the organophosphate moieties, the organophosphonate moieties, or both, being bonded to the oxide surface of the implantable substrate. Additionally or alternately, the second, outer surface can exhibit functional groups at a position remote to or omega to the organophosphate moieties, the organophosphonate moieties, or both, said functional groups comprising hydroxyl groups, phosphonate groups, phosphate groups, amino groups, thiol groups, or a combination thereof.

In another embodiment of the invention, the phosphorus-based coating can be bound to an oxide surface of an implantable substrate to attain a shear strength of at least about 20 MPa, or at least about 40 MPa or at least about 50 MPa, or at least about 60 MPa or at least about 70 MPa. Additionally, the phosphorus-based coating can be bound to the oxidize surface of the implantable substrate and/or a metallic implant to attain a tensile strength of at least about 60 MPa or at least about 80 MPa.

Other features of the present invention will be pointed out in the following description and claims, which disclose, by way of example, the principles of the invention and the best methods which have been presently contemplated for carrying them out.

DETAILED DESCRIPTION OF THE PREFERRED EMBODIMENTS

Figure 1:
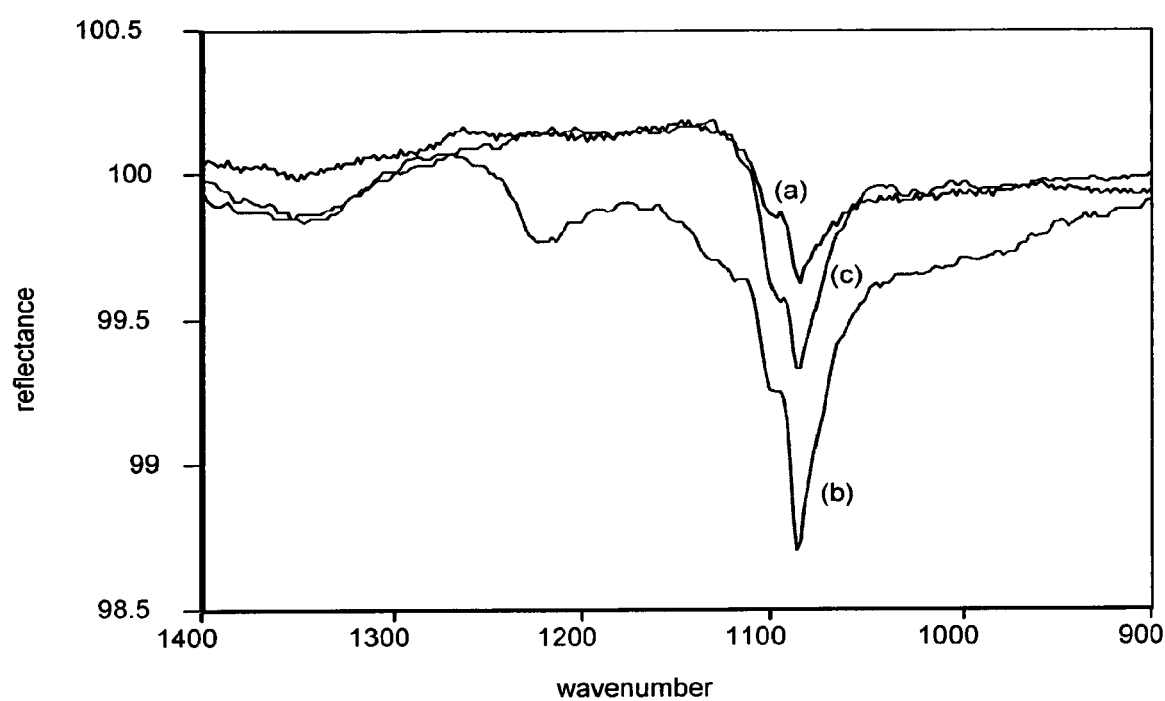
FIG. 1 shows IR spectra of (a) Titanium coated with 11-hydroxyundecylphosphonic acid; (b) Titanium coated with methyl-terminated poly(ethylene glycol), pre-treatment; and (c) Titanium coated with methyl-terminated poly(ethylene glycol), post-treatment with the Fenton like reagent.

According to one aspect of the present invention there is provided on the native oxide surface of a material a multi-segmented, phosphorous-based coating layer having a difunctional organo-phosphonic acid-based segment bonded to the native oxide surface of said material and a linking segment bonded to said organo-phosphonic acid-based segment. The present invention thus can provide a dense-coverage, adherent, phosphorous-based coating covalently bonded to the native oxide surface of a substrate.

Accordingly, the present invention also provides a phosphorous-based coating layer comprising a plurality of ω-functionalized organo-phosphonate moieties bonded to the native oxide surface of a substrate by a phosphonate bond and a plurality of one or more coating moieties selected from the group consisting of inorganic, organic, or bioactive moieties, each said coating moiety being bonded to the ω-functional group of at least one ω-functionalized organo-phosphonate moiety by means of a member of the group comprising a metal complex and an organic polymer, and when bonded by means of a metal complex, the metal complex further characterized by being derived from a metal reagent, preferably a metal alkoxide reagent, and when bonded by means of an organic polymer, the organic polymer further characterized by being derived from an ionic or step-reaction polymerization which incorporates one or more of said ω-functional groups into said polymer.

Preferred native oxide surfaces include, but are not limited to, the surfaces of titanium metal and its alloys, stainless steel and alloys, aluminum and its alloys, tantalum, silicon, cobalt-chromium and cobalt-chromium alloys consisting of mixtures of the elements cobalt, chromium, nickel molybdenum, and nitnol. Nevertheless, while many of the substrate surfaces are described herein as being titanium materials, other substrate materials may be used in compliance with the present invention, particularly those oxidized metals having low surface functional (e.g., hydroxyl) content. It is preferred for the organo-phosphonic acid-based segment to be derived from an ω-functionalized organo-phosphonic acid containing a hydrocarbon ligand having from about 2 to about 40 carbon atoms, wherein the hydrocarbon ligand is a linear or branched, saturated or unsaturated, substituted or unsubstituted, aliphatic or aromatic alkylene moiety.

Titanium metal from which medical implants are made typically has a purity such that the mass of the material is greater than about 98 wt % titanium, for example, the ALLVAC series of titanium metal available from Allegheny Technologies Company, for example, ALLVAC 70, which comprises about 98 wt % titanium, and ALLVAC 30 CP-1, which comprises 99.5 wt % titanium. Although the present invention is applicable to bulk titanium metal, which is of either lower or higher purity, and such material is not outside of the scope of the present invention, in general the lower purity material is not employed as medical implant material.

Typical titanium alloys from which medical implants are made contain at least about 80 wt % titanium, with the remainder comprising other metals and trace elements. Examples of titanium alloys (titanium materials containing more than trace amounts of other metals) which are used in the construction of medical implants are also found in the ALLVAC series of titanium alloys available from Allegheny Technologies Company, for example, ALLVAC Ti—15—Mo, which contains about 15 wt % Mo and in excess of about 84% titanium, ALLVAC 6-4, which contains about 4% vanadium, about 6 wt. % aluminum, and in excess of 89 wt % titanium (which alloy is also described herein as Ti-6Al—4V), and ALLVAC 6-2-4—Si, which contains about 6 wt % aluminum, about 2 wt % molybdenum, about 2 wt % tin, about 4 wt % zirconium, and in excess of 85 wt % titanium. Other purities and specifications of titanium alloys, whether used for the construction of medical implants or not, are known, and are also amenable to the present invention, and are therefore also contemplated in the term "titanium materials". It will be appreciated that materials which can be derivatized to have an oxide surface can also be employed.

For the application of phosphonate coatings using the general procedures described above, the phosphorous-based acid used is selected from the organic phosphonic acids. For purposes of the present invention, "phosphonic acid" refers to compounds having the formula $H_2RPO_3$, wherein R is an organic ligand with a carbon atom directly bonded to phosphorus.

Phosphonic acid species which are useful in the formation of coatings of the present invention may have, as the organic ligand of the molecule, a hydrocarbon which comprises an alkylene or arylene. Generally, useful alkylene and arylene hydrocarbon ligands will comprise between about 2 and about 40 carbon atoms, although the present invention contemplates organic portions outside of this range as the properties desired of the coating formed dictate larger or smaller organic portions.

An alkylene organic ligand of a phosphonic acid suitable for use in the present invention may be linear or branched, saturated or unsaturated, and unsubstituted or substituted with one or more substituents. An arylene organic ligand may comprise direct attachment of an aromatic moiety to the phosphorous atom of the phosphonic group, or it may be attached by an intervening alkylene moiety. Additionally, the arylene ligand may be incorporated into an alkylene chain (an arylene moiety having two or more alkyl substituents) or be a substituent depending from an alkylene chain. Substituent from arylene moieties may additionally be unsubstituted or may have one or more additional substituents.

Substituents on the hydrocarbon portion of phosphonic acids useful in the present invention may be appended to any carbon atom of the hydrocarbon ligand. Useful substituents are, for example, reactive functional groups, for example, a hydroxyl group, carboxylic group, an amino group, a thiol group, a phosphonate group, and chemical derivatives thereof. It will be appreciated that any functional group which can participate in a further derivatization reaction can be employed. Additionally, an alkylene hydrocarbon ligand may contain within the structure or appended to the structure, reactive moieties, for example sites of unsaturation, which may be further reacted in a polymerization reaction with reactive substituents on the hydrocarbon ligands appended to other phosphonate sites bound to the surface of the native oxide during a phosphonate derivatizing reaction. In this manner, a phosphonate-organo-polymeric layer may be formed on the oxide surface. An example of such a polymerization reaction is the preparation of a surface coating of acrylic phosphonic acid. Unexpectedly, when acrylic acid and methacrylic acid substituents are employed, the polymerization proceeds spontaneously upon exposure to air. For less reactive coatings, the polymerization can be performed by exposing the coating to conventional polymerization reagents and conditions.

In a particularly preferred embodiment, coatings are formed from phosphonic acids having an organic ligand functionalized at the ω-carbon of the ligand which is further reacted to form covalent bonds with chemical precursors of bone tissue protein, such as amino acids, or with the bone tissue protein itself. For ω-functionalized phosphonic acids, the application of the acid to oxide surface generally results in a self-assembled phosphonic acid film with the ω-carbon directed away from the substrate surface and available for covalent bonding or further chemical modification. Preferred ω-functional groups include hydroxyl, amino, carboxylate, thiol, and phosphonate groups.

It will also be appreciated that the reactive substituents pendant on the organic portion of a phosphonate bound to the oxide surface can be further reacted with reagents which are subject to hydrolysis reactions. Examples include metal alkoxides, examples of which are those having the structure M—(O—R)$_n$, where M is a metal, R is a linear or branched, saturated or unsaturated, aliphatic or aromatic, substituted or unsubstituted hydrocarbon moiety, and "n" is equal to a stable valance state of the metal. Examples of metal alkoxide compounds are zirconium-tetrakis-(t-butoxide), titanium-tetrakis-(t-butoxide), and silicon-tetrakis-(t-butoxide) where R is a t-butyl group, M is respectively Zr, Ti, and Si, and "n" is four. It will be appreciated that other hydrolytically reactive compounds which have two or more alkoxide ligands in addition to other ligands may also be utilized. For example, calcium alkoxides, for example, calcium bis(2-methoxy-ethoxide). In general, alkoxide ligated metals in groups 2 through 14 will find utility in these secondary functionalization reactions with phosphonate coatings of the present development.

When the reactive moieties appended to the free ends of the phosphonate coating layer are derivatized with a metal alkoxide (this is to say, a metal alkoxide "linking" segments is added) substituents having organic pi-electron delocalized moieties may be appended to the linking segment by reaction with the metal. Essentially any pi-electron delocalized compound capable of reacting with a transition metal alkoxide to covalently bond a ligand of the moiety to the transition metal is suitable for use with the present invention. Particularly useful compounds are pi-electron delocalized aromatic ring compounds. A particularly preferred aromatic ring compound is a phenol, which has a relatively acidic hydrogen that is readily transferred to the transition metal alkoxide to initiate a reaction that results in the formation of a transition metal phenolate. Five-membered heteroaromatic ring compounds having proton-donating ring substituents capable of reacting with the transition metal alkoxide are also desirable because of their high degree of pi-electron delocalization. Examples of such rings include furan, thiophene and pyrrole.

Adherent, dense-coverage, phosphate coatings bound to the native oxide surface of a titanium material (hereinafter, "a coating of Ti-phosphate") may be prepared by treatment of the surface under mild conditions with phosphoric acid according to the procedures described herein. For purposes of the present invention, "phosphoric acid" is defined according to its well-understood meaning, $H_3PO_4$. In the process of the present invention, treatment of a native oxide surface with phosphoric acid forms an inorganic phosphate coating that is rich in free hydroxyl groups. When the native oxide surface of a titanium material is coated with a phosphate coating of the present development and analyzed by XRD, two different titanium phosphate species were identified on its surface. One component, $Ti_4H_{11}(PO_4)_9*H_2O$, could be easily removed by rinsing with water, but the other, Ti-phosphate, remained on the surface. Indeed, XRD analysis of the rinsed foil, which had a dull purplish gray color, showed peaks only for Ti-phosphate, which were identical to those of powdered $H_2TiPO_4$. There is no long range order to the Ti-phosphate coating, and profilimetry of the surface (at 5 mm/s with 5 mg force) showed rough surfaces. The resistance of Ti-phosphate to removal from Ti by rinsing of "peeling" with Scotch™ tape was verified by XRD analysis; the change in relative intensities of XRD peaks for Ti-phosphate on the Ti substrate were measured before and after these tests was inconsequential. Since there is no preferred orientation for Ti-phosphate on the Ti substrate, phosphate group-derived hydroxyls of Ti-phosphate are likely also randomly oriented. The hydroxyl groups of the present invention phosphate coatings are available for further chemical modification (derivatizing), and may be reacted with, for example, hydrolytically reactive reagents, as described above for the phosphonate layers having reactive substituents. As with the phosphonate coating, further reaction of the phosphate hydroxyl moieties results in dense coverage of the surface by the derivatizing species. In this manner, species which would only provide a sparse coating on the native oxide if reacted directly can be used to provide a much denser coating on the phosphate derivatized surface.

Aqueous phosphoric acid solutions having a concentration up to about 3.0 M are preferred. For preparation of phosphate coatings of the present invention, phosphoric acid solutions having a pH more acidic than about pH 3.0 are preferred. Although these preferred ranges are convenient for providing coatings of the present invention, values outside of this range may be employed when reactivity and solubility considerations permit.

The concentration of phosphoric acid required to form an inorganic phosphate coating on an oxide surface is that concentration of phosphoric acid effective to form a stable film on the substrate surface without excessively dissolving the substrate. This can readily be determined by those of ordinary skill in the art without undue experimentation.

As with the coatings of phosphonate containing hydroxyl substituents, the hydroxyl groups of the Ti-phosphate coatings of the present invention can also serve as reactive sites for covalent attachment of hydrolytically reactive reagents, for example, Zr or Si alkoxides. It is observed, by comparison of infrared absorbance by a characteristic feature of a surface bound moiety, that surface loadings of these organometallics are 1-2 orders of magnitude higher on Ti-phosphate coatings than those obtained on the native oxide of Ti in which only about 15% of surface oxygen is derived form hydroxyl groups.

Alkyl amines and silanes are reagents commonly used to couple functionalized organics to a variety of hydroxylated surfaces, and bond readily to the phosphate surfaces of the present invention. For example, octadecyl(triethoxy)silane reacts irreversibly with Ti-phosphate but not with the Ti native oxide surface under comparable conditions. The phosphate surfaces of the present invention may be further derivatized by reagents typically used to react with hydroxylated oxide surfaces of non-titanium materials.

As described above, the native oxide surface of titanium materials is not amenable to profound alteration of the chemical properties of the surface using typical derivatizing reactions. In addition, as described above, the coverage of hydroxyl groups on a native oxide surface of titanium materials is sparse, thus, derivatizing reagents which react with hydroxyl groups (hydrolytically reactive reagents) typically yield a coverage by the derivatizing species which is too sparse to provide for a significant change in the behavior of the surface of the material. This is particularly problematic with respect to attempts to alter the native oxide surface of titanium materials with these reagents to promote adhesion when the materials are placed in contact with bone tissue.

The phosphate or phosphonate coatings of the present invention provide a layer which is sufficiently adherent and provides dense-coverage of a reactive surface directly bonded to sparsely-functionalized substrates, such as the native oxide surface of titanium materials. Studies indicate that coverage yielded by reacting phosphate coating hydroxyl groups of the present invention with derivatizing reagents yield coverage of the oxide surface that is about one to two orders of magnitude greater than that obtainable by direct reaction of the derivatizing reagent with the surface hydroxyl groups of the native oxide surface. These dense-coverage, adherent phosphate or phosphonate coatings also can promote the adhesion of bone tissue, and are amenable for further derivatization by chemical species which further promote adhesion of various coatings. For example, the surface can be provided with a linking segment which includes a bioactive moiety that promotes the adhesion and proliferation of osteoblasts. Owing to the increase in specific surface density of reactive sites afforded by the ω-functionalized phosphonic acid-based coating layer over the density of reactive sites available on the native metal oxide surface, increased interaction between the surface of the present development and tissue contacted to the surface is observed.

The use of ω-functionalized phosphonic acid, for example, 1,6-diphosphonohexane (a bis-phosphonic acid, with phosphonate groups terminating either end of a 6 carbon alkyl chain) and 1,12-diphosphonododecane (a bis-phosphonic acid with phosphonate groups terminating either end of a 12 carbon alkyl chain), to apply a coating adhered to the native oxide surface of a material provides a layer which can be the basis of a segmented coating described above. Such coatings can be formed by stepwise reaction of the ω-functional group with a linking moiety, for example, a metal alkoxide, for example the Zr, Si, Ti, and Ca alkoxides described above, to provide a segmented coating having a bisphosphonate segment bonded to a native oxide surface and a metal oxide linking segment bonded to the bisphosphonate segment.

When the metal alkoxide segment contains hydrolyzable ligands, for example, zirconium tetrakis(t-butoxide), one or more tert-butoxide ligands remain after surface attachment. These ligands can be hydrolyzed to provide metal hydroxyl sites, or which can be reacted with, for example, an organic acid, providing a bonded acid. The organic moiety thus attached can in turn be used to attach other moieties, for example, bioactive moieties.

An example of this synthetic scheme is bonding a difunctional acid to a metal alkoxide linking segment, for example, attachment of maleimidobutyric acid (which contains carboxylic acid functionality terminating one end of a four carbon chain and a maleimide nitrogen terminating the other end). Attachment of the maleimide functional group using this synthetic scheme proceeds rapidly, essentially upon contact, and the maleimide functional end can be employed to further bind bioactive proteins and peptides, for example, those which promote the attachment of osteoblasts to the surface, thus providing a surface which promotes bone tissue adhesion.

An example such a surface is the surface of an implant which has been functionalized with a peptide, for example, RGDC (the cysteine modified fibronectin cell attachment peptide argynine-glycine-aspartic acid). Although the reaction between the peptide and the maleimide linking segment goes to completion, the reaction rate for the coupling reaction is slow, taking several days to run to completion at room temperature.

Additional examples of the peptides which can be attached using this synthetic scheme include KRSR (lysine-arginine-serine-arginine, which is specific for osteoblast attachment) in the form of derivatives, for example KRSRGGE and KRSRGGC (the glycine-glycine-glutamic acid and glycine-glycine-cysteine modified derivatives respectively of KRSR).

Additional examples of bioactive moieties which can be attached to a surface using this scheme include biodegradable polymers, for example, polylactide ($-[-CH_2-C(O)-O-]-)_n$ and polyglycolic acid ($-[-CH(CH_3)-C(O)-O-]-)_n$ which can be attached through strong coordinate bonds of the acid terminal groups to the zirconium metal center in a surface layer having a zirconium alkoxide linking segment. It is known to incorporate bioactive molecules, for example lactam antibiotics and growth factor-releasing hormones into such polymers. An implantable surface containing polymers of this type would provide antibiotics or hormones at the site of implantation which might be advantageous in promoting healing of the surgical site about an implanted material. It will be appreciated that these polymers can also be used as a linking segment, the functional groups of the polymer coordinating by hydrogen bonding to the ω-functional group of the surface layer formed from an ω-functionalized phosphonic acid. In this sense, the biodegradable polymers provide the linking segment, attaching the bioactive material copolymerized with the degradable polymer to the surface. Additional reactions which can be carried out with an alkoxide linking segment include the stepwise provision of layers of new materials on a surface through sequential solution reactions. This synthetic scheme can be illustrated by growth of a hydroxyapatite ($Ca_{10}(PO_4)_6(OH)_2$) surface on the above-described coating layer which has been provided with a calcium alkoxide linking segment. A hydroxyapatite material can be formed by reacting the coating layer surface alternately with phosphoric acid ($H_3PO_4$) and then an aqueous calcium ion source, for example, $CaCl_2$, $CaNO_3$. It will be understood that there numerous other reactions are possible.

It will be appreciated that any of the ω-functionalized phosphonic acid moieties described above will provide a surface which can be reacted with numerous other polymers and oligomers, for example, those traditionally used to form a protective, decorative, or adhesive coating. When such linking segments are introduced into coatings of the present invention, it will be appreciated that adhesion to the underlying native oxide surface will be improved. For example, when an ω-hydroxy-organophosphonic acid moiety is used to form a coating layer with a native oxide surface of a material, the free hydroxyl ends can be reacted with, for example, an epoxy adhesive by, for example, condensation polymerization, thereby providing in epoxy adhesive coating which is attached to the coating layer through a specific surface area bond density that exceeds what is available by direct application of the epoxy adhesive to the underlying native oxide surface. As a result, the surface area specific bond strength between the adhesive layer and the coating layer of the present invention exceeds the surface area specific bond strength observed with direct application of the adhesive to the underlying native oxide surface. It will be appreciated that the ability of the surface of the coating layer of the present invention to provide for increased surface area specific reaction sites will improve the adhesion of numerous other coating materials, for example, acrylate polymer coating.

The phosphate coatings of the present invention are rich in free hydroxyl groups. The phosphonate coatings can be made to have hydroxyl groups by using precursor acids having hydroxyl group substituents. Each of these coating layers may be further functionalized to promote covalent attachment to bone tissue proteins, or precursors thereof, for example, by using thiol compounds of the type conventionally employed to promote adhesion between gold metal implants and bone tissue. The hydrocarbon ligands of the organopolyphosphonate coatings may likewise be functionalized at a substituent on the organic ligand portion as described above for phosphonate ligand coatings to form covalent bonds with chemical precursors of bone tissue protein or with the bone tissue protein itself.

The coatings of the present invention can be applied to essentially any implant intended for bone or dental tissue contact fabricated from a material having an oxide surface at the intended bone or dental tissue interface. Implants made of titanium and alloys thereof may be employed, as well as implants which are made of materials that can be provided with an adherent titanium or other material oxide surface. Additionally, the phosphorous-based coatings of the present invention may be applied to oxide surfaces of materials other than titanium-materials, for example, stainless steel and alloys, tantalum, cobalt-chromium and cobalt-chromium alloys consisting of mixtures of the elements cobalt, chromium, nickel, molybdenum, and nitnol and provide similar potential for bone and coating adhesion.

The methodology of the present invention enables strong adhesion between a dental or osteopathic implant and incipient bone tissue via a network of strong chemical bonds. An implant device can be fabricated and its surface processed ex-situ to provide a composite coating on the implant surfaces that will give rise to a strong, non-fracturable bone-to-implant seal following implantation. The methodology is amenable to vapor-phase or solution-phase (aerosol spray-on or "dip coating") chemistry and proceeds under mild conditions, especially compared to plasma or laser-induced deposition. Adhesion of the phosphorous-based surface coating has been found to exceed 40 MPa of shear stress and 80 MPa of tensile stress.

More complex species, for example, a protein or peptide, may also be bonded via the derivatized surface of the present invention to the underlying native oxide surface of an implant. For example, bonding the fibronectin cell attachment peptide arginine-glycine-aspartic acid (RGD), for example, in its RGDC derivative form, to a surface through an organic tether is thought to enhance the osteoconductivity of the surface by providing sites for cell attachment and spreading. As described above, conventional methods for such providing surface peptide attachment to implant materials, such as Ti, Ti alloys, stainless steel, cobalt-chromium and its alloys, are often problematic and only low yields of such attachment are possible. Using the surface bonded coating of the present development, for example, a carboxylate-functionalized phosphonate coating, a cysteine-modified fibronectin cell attachment peptide (RGDC), which is commercially available (American Peptide), affords the possibility of attachment of the peptide to a reactive site on a surface of the present invention via formation of a thiol-ether bond using the surface coating of the present invention treated with traditional organic derivatization reaction techniques. It will be appreciated that other derivatization reactions are also possible.

Examples of additional peptides which may be attached include those which show specificity for cell attachment, for example KRSR (lysine-arginine-serine-arginine). These peptides can be modified without affecting their specificity for osteoblast attachment, for example, by attaching GGE (glycerine-glycine-glutamic acid) or GGC (glycine-glycine-cysteine) sequences to improve attachment to the surface, thus KRSRGGE and KRSRGGC respectively.

Another aspect of the present invention is a process for the provision of an adherent, phosphorous-based coating layer having a difunctional organo-phosphonic acid-based segment bonded to the native oxide surface of said material and a coating bonded to said organo-phosphonic acid-based segment, the process comprising: (i) providing a native oxide surface bearing an ω-functionalized organo-phosphonic acid moiety bonded thereto; (ii) and bonding said ω-functional groups thereof, or derivatives of the functional groups thereof, with a bioactive, organic, or inorganic moiety comprising the coating. Preferred ω-functional groups are hydroxyl-, carboxylate-, amino-, thiol-, and phosphonato-functional groups, or these groups further derivatized by reaction with a metal or organo-metal reagent, for example an alkoxide. These groups participate in further bonding with moieties comprising the organic, inorganic, or bioactive coating layer, either through strong chemical bonding, for example, covalent bonding, or through weaker bonding interactions, for example, hydrogen bonding.

Preferred metal reagents for derivatizing ω-functional groups are, for example metal alkoxides, for example zirconium tetrakis(t-butoxide), silicon tetrakis(t-butoxide), titanium tetrakis(t-butoxide), and calcium bis(2-methoxy-ethoxide).

A preferred method of attaching a bioactive species to a native oxide surface comprises providing a phosphorous-based coating layer as described above wherein said ω-functionalized organo-phosphonate moieties are an alkyl-bisphosphonate which has been derivatized with a metal alkoxide, and further reacted with an organic moiety, said organic moiety comprising a peptide bonded by a thiol-ether bond to a malimido-carboxylic acid group, said reaction providing a carboxylate bond to said metal alkoxide derivatized ω-functional group.

Additionally, organic moieties that may be added to the ω-functional group of a phosphonic acid-based layer which comprise oligomers or polymers, for example, adhesive polymers, for example epoxides, polymers which form surface coatings, for example acrylates, and oligomers, for example, those which have bioactive properties or which can be used to attach compounds or precursors to compounds having bioactive properties, for example, a poly(lactide-co-glycolide) which has antibiotic activity.

Inorganic coating layers which may be bonded include, for example, hydroxyapatite.

The present invention thus includes the methods by which the coated substrates of the present invention are formed. Therefore, in accordance with another embodiment of the present invention there is provided a method of bonding a layer of a phosphorous-based acid moiety to a sparsely-functionalized (e.g., titanium) oxide surface comprising coating said oxide surface with a phosphorous-based acid moiety self-assembled layer and heating said coated oxide surface until said self-assembled layer is bonded thereto, the phosphorous-based acid moiety comprising the self-assembled layer being selected from the group consisting of phosphoric acid and organophosphonic acids.

Preferred coatings are those which have been formed from alkylene- and arylene-organophosphonic acids, including substituted alkylene and arylene phosphonic acids. More preferred are substituted alkylene phosphonic acids with a reactive substituent omega to the phosphonic acid functional group. In some embodiments, preferred oxide surfaces include, but are not limited to, the native oxide surfaces of titanium materials. It is preferred for the phosphonic acid to be in the form of an aqueous solution having a pH more acidic than about pH 3.0.

In some embodiments the adherent, multi-segmented, phosphorous-based coating layers of the present invention promote interaction between the coated substrate and the environment in which the coated substrate is placed by using the coating layer to improve the interaction of the two. An example of this is using a coating layer of the present invention to promote the adhesion of bone tissue to a titanium substrate on which a coating of the present invention is placed. In other embodiments, a segment of the adherent, multisegmented, phosphorous-based coating layer comprises a moiety which has surface active properties, and thus itself interacts with another surface. An example of this is the increase in adhesive force observed between an adhesive and a titanium native oxide surface when the adhesive is included as a linking moiety in the coating layer of the present invention.

The methods of the present invention provide an adherent, phosphorous acid-based coating layer bonded to an oxide surface of a material. These coating layers have utility in derivatizing the oxide surface to alter the properties of the surface. For example, the chemical properties of the surface, for example, the affinity of the surface for hydrophilic or lipophilic substances may be altered in this manner. In addition, the electrical properties, for example, the ability of the surface to carry out charge carrier injection processes can be altered in this manner. While the methods and coating layer of the present invention have broad utility in providing a chemically derivatized coating layer on oxide surfaces, it is anticipated that the present invention will be most useful in the provision of phosphorous acid-based coatings which act as interface between the oxide surface and overlayer adhered thereto, thereby improving or facilitating the adherence of said overlayer to the oxide surface. Examples of such uses include improvement in the adhesion of an adhesive for a metal oxide surface, for example, an epoxy adhesive layer bonded to the native oxide surface of a titanium alloy, and the provision of an osteoadhesive layer in a medical implant in living bone tissue. Although the method of the present invention has broad applicability in providing a phosphorous acid-based adherent coating layer to an oxide surface, it is anticipated that the method of the present invention will be most useful in the provision of an adherent phosphorous acid-based coating layer on the oxide surface of metals, semiconductors, and insulators. Examples of oxide surfaces include, but are not limited to, oxide surfaces which form spontaneously (native oxides) as well as those applied to a surface, for example by sputtering. In particular, it is anticipated that the method will find greatest utility in the provision of a phosphorous-based coating layer on oxides of traditionally low reactivity, for example, the native oxide surface of titanium alloys. Finally, although the method and coating layer of the present invention has broad applicability in providing an adherent phosphorous acid-based coating layer on oxide surfaces on a wide scale of sizes, it is anticipated that the present invention will find its greatest utility in the provision of coating layers in operations wherein coating is done in a continuous operation, for example, by lamination of a carrier furnished with a phosphorous acid and a carrier of material comprising the oxide surface to which the coating layer is applied.

Methods

Without wanting to be bound by or to any particular theory, as described in co-pending U.S. patent application Ser. No. 10/701,591, filed Nov. 4, 2003; Ser. No. 10/405,557, filed Apr. 1, 2003; and Ser. No. 10/179,743, filed Jun. 24, 2002, each of which is incorporated herein by reference in their entirety, it is believed that when a phosphorous acid is contacted to an oxide surface for a sufficient period of time under suitable temperature conditions, there is formed a bond between the acid functional group and the oxide surface. Surprisingly, the inventors have discovered that adherent phosphorous coating layers can be prepared utilizing a carrier to convey a coating composition comprising one or more phosphorous acids to the oxide surface to be coated.

Without being bound by or to any particular theory, it is believed that by selecting the hydrophilic properties of the carrier to be compatible with the phosphorous acid used to provide the coating the method of the present invention provides a coating layer with improved order and improved bonding of multi-layer character over methods utilizing "dip" coating, as described for example in the aforementioned co-pending U.S. patent application Ser. No. 10/179,743. This improvement in layer organization and bonding provides improved coverage of the surface, improved adhesion of the coating layer, and increases the chemical and electronic communication between the coating layer and the surface.

In addition, the method of the present invention is believed to provide improvement in the efficiency of applying a coating of the invention to a large surface area in comparison to dip-on or paint-on methods. It will be appreciated that the method of the present invention is readily adaptable to a continuous coating operation using a web or belt system to provide a coating of the invention to a continuous supply of oxide surface. The method of the present invention also provides a convenient method of placing a coating on an oxide surface in a pattern which has here-to-fore only been possible by masking portions of the surface to be coated prior to providing the coating. Accordingly the method of the present invention provides for a reduction in the unit operations necessary required to prepare a patterned phosphorous acid-based coating layer on an oxide surface.

The method of the present invention comprises contacting a carrier conveying a coating composition comprising a phosphorous acid to an oxide surface for a sufficient duration and under temperature conditions sufficient to form bonds between at least a portion of the furnished phosphorous acid and the contacted oxide surface. No particular environmental conditions are required to provide a coating layer on an oxide surface by the present invention method, although if it is desired the present invention can be carried out within environmental chambers or under inert atmospheres.

It will be appreciated that the carrier may be in many different forms, for example, a roller, pad, sheet, roll, web, or belt. Other forms will be apparent. It will also be appreciated that the method of contacting the carrier to the oxide surface will vary depending upon the phosphorous acid(s) comprising the coating solution, the concentration, the temperature conditions, and the nature and character of the oxide surface to be coated.

In keeping with the principles set forth herein, examples of the various methods which may be used to contact the carrier to the oxide surface include fashioning the carrier into a roller which is rolled across the oxide surface, fashioning it into a stamp or plate which is contacted to the oxide surface either manually or by mechanical means, furnishing a roll of the carrier with the coating solution which is unrolled onto the oxide surface, laminating a web or belt of carrier material which has been furnished with the coating solution to a supply of the oxide surface. It will be appreciated that when the oxide surface permits it to be presented as a web, belt, or sheet, for example, acrylic and poly(ethylene terephthalate) (PET) which has been coated with silicon dioxide, a continuous lamination process can be used. It will also be appreciated that when the oxide surface is in a more or less rigid form, for example, an indium tin oxide coating on glass, a feeding mechanism accompanying a belt, chain, or web-feed type of lamination equipment can be adapted to laminate sections of the oxide surface with a continuous belt or web of the carrier. It will be appreciated that many other modifications exist in the coating, printing and laminating arts which can be adapted to contact both flexible and rigid carrier materials with oxide surfaces residing on either flexible or rigid substrates.

The duration of the contact between the carrier and the oxide surface will depend upon the coating solution selected, the oxide surface, and the temperature conditions obtaining during contact. For example, for some oxide surfaces, for example, the native metal oxide on aluminum, and for some acids, for example, hydroxyundecylphosphonic acid, the coating layer will form spontaneously at any ambient temperatures, for example about 20° C., and above. Typically, for short contact times, for example, about 5 minutes or less, contact is made under temperature conditions of from at least about 100° C. up to about 200° C. If lower temperatures are employed, or for different oxide surfaces and phosphorous acids, longer contact times, for example several hours, may be required. One of ordinary skill can easily determine the duration of contact required at a particular temperature to form a satisfactory coating by placing a coupon of carrier which has been furnished with the intended coating solution in contact with a coupon containing a sample of the oxide surface to be coated into an oven maintaining the intended contact temperature for varying times and measuring the amount of phosphorous acid-based coating formed on the oxide surface. Other methods of determining the minimum necessary contact time at a particular temperature for a particular coating solution and oxide surface will be apparent.

Typically, contact times employed in the method of the present invention are typically from about 1 minute to about 20 minutes at temperatures from ambient, e.g., about 20° C., to about 200° C. More preferably, contact times from about 5 minutes to about 20 minutes are employed at temperatures from about 50° C. to about 200° C.

It will be appreciated that when heating is required to drive the coating reaction, numerous arrangements may be employed to provide the heat to the contacted carrier and oxide surface. These include, but are not limited to, applying a heated body to the distal side of the carrier while the proximal side of the carrier is in contact with the oxide surface, contacting the carrier and oxide surface within a heated zone, for example, within an oven, and contacting the carrier and oxide surface and transporting them in contact into a heated zone. In the latter example, the oxide surface and carrier can be in the form of a sheet which is transported through an oven or furnace on a belt or in a batch conveyance. Alternatively, the oxide surface and carrier can be in the form of a two webs which are contacted and passed in contact through a heated zone, as for example, will be familiar to those of skill in the laminating arts. In another non-limiting example, heat to drive the coating reaction can be provided by heating the oxide surface separately and bringing the carrier into contact with the heated oxide surface thereafter.

The process of conveying the coating composition to the oxide surface requires furnishing the coating composition to the carrier. This can be accomplished by contacting the carrier with a coating solution, removing the carrier from contact with the coating solution, and contacting the carrier with the oxide surface. The coating solution comprises the phosphorous acid to be used in forming the coating and a solvent, for example, an alcohol. In some preferred processes, between the step of removing the carrier from contact with the coating solution and the step of contacting the carrier conveying the coating to the oxide surface, an evaporation step is conducted during which a portion, preferably a substantial portion, of the solvent conveyed by the carrier from the coating solution is evaporated. In some preferred embodiments, after the drying step the carrier appears to be "dry" when visually inspected, and can be handled, transported, and packaged without exuding any solvent. In some embodiments the carrier provided with the coating composition in this manner will be employed to provide a coating on an oxide surface remote in time and/or location from the time and place in which the coating composition was provided to the carrier. It will be appreciated that other methods of providing the coating composition to the carrier can be employed.

The present invention further provides a method of constructing a medical device with multiple surface functionality, comprising the steps of 1) bonding an adherent, self-assembled phosphorous-based coating to the native oxide surface of an implantable device; 2) masking the regions of the device not to be reacted; 3) allowing unmasked regions of the device to react with additional reagents to achieve a desired property for the unmasked region; and 4) removing the masks. In Step 1, the coating layer may be formed as a self-assembled monolayer according to the method described in U.S. patent application Ser. No. 10/701,591. In addition, if more than one region receives a second coating, additional mask steps are necessary.

Without wanting to be bound by or to any particular theory, it is thought that the evaporation step improves the organization of the coating composition on the carrier prior to contacting the carrier to the oxide surface.

Carriers

As indicated above, the carrier of the present invention can comprise numerous flexible and rigid materials. In general the carrier is selected to have some affinity, for example, hydrogen bonding or Van der Waals interaction, for the phosphorous acid(s) comprising the coating solution, but not to react with them. Without being bound by or to any particular theory, it is believed that in selecting the carrier to exhibit an affinity for the phosphorous acid(s) comprising the coating solution the carrier imposes some order on the acid moieties therein prior to contacting the surface, and thereby presents the phosphorous acid from which the coating is derived to the oxide surface as a collection of moieties having at least short range ordering, and thereby providing a coating layer which has imparted to it at least localized ordering of the coating moieties. Again without wanting to be bound by or to any particular theory, it is believed that this is similar to the organizational effect in amphiphilic films at an air/water interface.

Accordingly in some embodiments, preferred carriers are those which have non-reactive surface hydroxyl groups with which the phosphorous acid(s) comprising the coating solution can form hydrogen bonding. Examples of this include cellulose materials, for example, cotton fiber. Guided by these general principles it will be apparent that materials having surfaces which have been derivatized to have greater or lesser hydrophilic nature can also be employed. It will be appreciated that this includes surfaces comprising materials which, for example, fibers have regions comprising various alcohol, ether, ester, amino, amido and like moieties. It will also be appreciated that this includes both materials in which this type of functionality is either naturally occurring or in which the functionality has been introduced by chemical derivatization of the materials. An example of one such naturally occurring material is cotton fiber and materials made therefrom. It will be appreciated that numerous surface modifications of numerous materials are possible to bond moieties containing functional groups which can "fine tune" the hydrophilic nature of the surface to maximize the organizational effect of the carrier for a particular coating solution.

It is contemplated that suitable carriers for the present method include those which have absorbent properties for the coating solution, adsorbent properties for the coating solution, or both. Thus, the carrier material can have, for example, the form of a reticulated or porous material which provides interstices into which a coating solution can be take up by absorption. The carrier can also be non-porous, utilizing adsorptive properties, for example, a material which has an affinity for the coating solution such that it is readily "wetted" by the coating solution. Suitable carrier materials will generally have a mixture of both types of properties. Thus, it will be appreciated that for some applications, a non-porous, smooth carrier will be employed which relies on adsorption of the phosphorous acid comprising the coating solution to convey it to the oxide surface to be coated. In other applications, the carrier will be porous or reticulate and have absorptive properties for the coating solution.

Preferred carriers include cellulose materials having a hydrophilic surface, for example woven and non-woven cotton and woven and non-woven polymers which have hydrophilic surfaces. Rigid materials having hydrophilic materials which are non-reactive toward phosphorous acids are also preferred. It will be appreciated that surfaces which have been derivatized with a phosphorous acid which contains hydrophilic functional groups may also be employed.

Coating Solutions and Compositions

As the term is used herein, the coating composition comprises the acid used in forming the coating layer of the invention organized on the carrier, some amount of the solvent retained from the coating solution, and optionally other constituents which may be added to improve the stability or handling characteristics of the coating solution, as are known in the art.

In general, coating compositions suitable for use in the present invention method comprise an acid selected from the group consisting of phosphoric, organo-phosphoric, and phosphonic acids and a solvent. In some preferred embodiments the solvent is water or an alcohol. Particularly preferred are phosphonic acids and alcohol solvents, particularly ethanol. In general, coating compositions employ dilute solutions of the acid, typically in the millimolar (mM) concentration range. In some embodiments the coating compositions are prepared from solutions having an acid concentration of from about 0.01 mM to about 5.0 mM, more preferably from about 0.1 mM to about 3.0 mM. However, in accordance with known principles and the chemical stability of the carrier materials and oxide surface used in the process the concentration of the solution may be adjusted to higher or lower values.

Acids

As used herein, the phrase "phosphorous acid" refers to phosphoric acid ($H_3PO_4$), organophosphoric ($R^1$—O—$PO_3H_2$), wherein $R^1$ is an organic moiety bonded to the phosphorous atom through an oxygen atom, and phosphonic acid compounds having the formula R—$PO_3H_2$, wherein R is an organic ligand, that is, wherein a carbon atom is directly bonded to phosphorus. In general, the organic moiety in organo-phosphoric acids can be selected from the same organic moieties described below for the phosphonic acid organic ligand, guided by general chemical principles regarding the stability of the phosphate/phosphonate species after bonding to an oxide surface. Any of the acid species which are disclosed for preparing coatings in any of co-pending U.S. patent application Ser. No. 10/701,591, filed Nov. 4, 2003; Ser. No. 10/405,557, filed Apr. 1, 2003; and Ser. No. 10/179,743, filed Jun. 24, 2002, each of which is incorporated herein by reference in their entirety, may be employed in the methods of the present invention to prepare the coatings of the present invention.

The preferred acids for use in the present invention are phosphonic acids. Preferred phosphonic acids have an organic ligand selected from the group of organic moieties consisting of aliphatic and aromatic hydrocarbon moieties having from about 2 to about 40 carbon atoms, and more preferably from about 2 to about 20 carbon atoms. However, the present invention contemplates organic moieties having an amount of carbon atoms lying outside of this range as the properties desired of the coating formed dictate larger or smaller organic moieties.

Suitable aliphatic organic moieties may be linear or branched, saturated or unsaturated, and may be optionally substituted with one or more functional groups, including aromatic substituents. Aromatic organic moieties may comprise arene structures, for example a monomeric, oligiomeric, or polymeric arene structure, for example anthracene and pentacene, which are directly bonded to a phosphate moiety. Alternatively, aromatic moieties may be bonded to a phosphate moiety through an intervening aliphatic moiety. Aromatic moieties may optionally be substituted on any carbon with one or more functional groups.

In some preferred embodiments the ligands are selected from organic moieties which are based on organic compounds having electron donor and acceptor properties, for example, moieties which are based on derivatives of the art recognized electron acceptor and donor molecules tetracyanoquinodimethane (hereinafter "TCNQ"), tetrathiofulvalene (hereinafter "TTF"), and quarterthiophene-phosphonate (hereinafter "4TP") the structures of which are well known. As is known, TCNQ, TTF and 4TP are typically used as building blocks in the provision of organic conductors. As described in detail in co-pending U.S. patent application Ser. No. 10/701,591, filed Nov. 4, 2003, which is incorporated herein by reference, substituted molecular derivatives of TCNQ with altered electron acceptor properties are also known and have been described, for example, by Yamashita et al., *J. Mater. Chem.*, 8(9), 1933-1944 (1998), which is incorporated herein in its entirety by reference. Moieties based on these TCNQ derivatives are also preferred as ligands in phosphorous acids employed in coating solutions for the present development.

Known also, and described in detail in co-pending U.S. patent application Ser. No. 10/701,591, filed Nov. 4, 2003, which is incorporated herein by reference, are TTF derivative compounds with altered electron donating properties. Such molecules have been described, for example, by Hasegawa et al., *Synth. Met.*, 86, 1801-02 (1997), which is incorporated herein in its entirety also by reference. As has been described, TTF can be substituted, with electron donating groups to enhance its electron-donor properties. Moieties based on these TTF derivatives are also preferred as ligands for phosphorous acids used in coating solutions for the present invention.

Substituents on the hydrocarbon ligand of phosphonic acids useful in the present invention may be appended to any carbon atom of the hydrocarbon ligand. Useful substituents are, for example, those which may influence the hydrophilicity and/or lipophilicity of a coating prepared therefrom, for example, alkyl groups, and reactive functional groups, for example hydroxyl, carboxylic acid, amino, thiol, sulfonic acid, phosphonic acid, and chemical derivatives thereof. It will be appreciated that any functional group which can participate in a further derivatization reaction can be employed. Additionally, suitable hydrocarbon ligands may contain within their structure or appended to their structure, reactive moieties, for example sites of unsaturation, which may be further reacted in a polymerization reaction with reactive substituents on the hydrocarbon ligands appended to other phosphonate sites bound to the surface of the oxide during a phosphonate derivatizing reaction. Additionally, reactive functional groups may be included on one or more carbon atoms of the organic ligand of the acid used to form the coating. These functional groups may be employed to further derivatize the coating layer formed, as explained in detail below and in each of co-pending U.S. patent application Ser. No. 10/701,591, filed Nov. 4, 2003; Ser. No. 10/405,557, filed Apr. 1, 2003; and Ser. No. 10/179,743, filed Jun. 24, 2002, each of which is incorporated herein by reference in their entirety.

In a particularly preferred embodiment, coatings are formed from phosphonic acids having an organic ligand functionalized at the ω-carbon of the ligand. In general, when ω-functionalized phosphonic acids are used to form the coating layers of the invention, after reaction of the acid to oxide surface resultant phosphonic acid film generally comprises phosphonate moieties bonded to the oxide surface with the ω-carbon directed away from the surface and available for covalent bonding or further chemical modification. Preferred ω-functional groups include hydroxyl, amino, carboxylate, and thiol groups.

Another class of substituents which may advantageously be bonded to a phosphonic acid organic ligand is pi-electron delocalized moieties. Particularly useful compounds are pi-electron delocalized aromatic ring compounds (oligo- and poly-arene ligands). Five-membered heteroaromatic ring compounds having phosphonic acid ring substituents are also desirable because of their high degree of pi-electron delocalization. Examples of such rings include furan, thiophene and pyrrole.

Oxidized Surfaces

As explained in detail in each of co-pending U.S. patent application Ser. No. 10/701,591, filed Nov. 4, 2003; Ser. No. 10/405,557, filed Apr. 1, 2003; and Ser. No. 10/179,743, filed Jun. 24, 2002, each of which is incorporated herein by reference in their entirety, a coating layer comprising a phosphorous acid in accordance with the present invention can be formed on both native oxide surfaces and oxide surfaces which are deposited on a substrate or formed on an existing oxide surface. Accordingly, non-limiting examples of native oxide surfaces upon which a phosphorous acid-based film can be formed include materials which have metallic, conducting, semiconducting, and insulating properties, as those terms are defined, for example, by A. West, *Basic Solid State Chemistry*, second edition, John Wiley & Sons, New York, pp. 110-120, which is incorporated herein in its entirety by reference. Examples of substrates suitable for use in the process of the invention include, but are not limited to materials which possess a native oxide surface, that is, they comprise an oxide or form a native oxide upon exposure to the ambient environment. Non-limiting examples of oxide materials include bulk metal oxides, for example silica and alumina, oxides deposited on a substrate, for example, conducting oxides, for example, indium doped tin oxide and zinc/indium doped tin oxide each deposited on a glass substrate, and oxide insulators, for example, low dielectric constant glass in gate insulator material of integrated circuits and metal oxide deposited on plastic substrates, for example "stacked" metal oxide on PET plastic (which has a top layer of silicon dioxide), for example anti reflective plastic obtained commercially from Bekaert Specialty Films. Though in one embodiment oxide surfaces are preferred surfaces, it is believed that other oxidized surfaces may be useful as well, e.g., nitrides, oxynitrides, carbides, oxycarbides, sulfides, oxysulfides, or the like. Also, it is believed that the present invention can be formed on the surface of bulk oxides.

Non-limiting examples of materials which form oxidized surfaces upon exposure to the ambient environment (oxygen) include steels, including stainless steels, iron, and metals which acquire a non-ablating oxide coating upon exposure to the ambient environment, for example, titanium, titanium alloys, aluminum, aluminum alloys, tantalum, cobalt-chromium and cobalt-chromium alloys consisting of mixtures of the elements cobalt, chromium, nickel and molybdenum. Additional examples of materials which acquire a native oxide layer upon exposure to the ambient environment are ceramic materials, for example, silicon nitride and semiconductors, for example silicon. Also suitable for application of a coating of the present invention are materials which have an oxide coating imparted to them intentionally, for example, thick film oxide insulators in semiconducting devices, and those which can be derivatized to have an oxidized surface, for example, gallium arsenide, gallium nitride, and silicon carbide. Also suitable for use in the provision of a coating layer of the present invention are naked surfaces which can undergo hydrolysis and which have an adsorption affinity for phosphonic acid functional groups, for example, silicon nitride.

Particularly preferred substrates are those which are useful in preparing electronic devices and those useful for mechanical devices for contact with biological tissue or fluids. An example of those useful for the preparation of electronic devices are thick oxide insulating layers on gate junctions for use in bio-electronic sensors which are suitable for in vivo and in vitro diagnosis and monitoring of conditions. An additional example is indium tin oxide conducting oxide deposited on glass. An example of a surface useful in the preparation of mechanical devices is an implantable material, for example, a titanium reinforcing member useful for in vivo implant in the repair of bone tissue.

As mentioned above, suitable surfaces include the surfaces of semiconductor substrates, for example silicon single crystal surfaces. They include also the surfaces of polycrystalline substrates, for example, metals, for example titanium and its alloys, aluminum and its alloys, and silicon. Also included are the surfaces of amorphous substrates, for example, the surface of an oxide conductor or oxide insulator. Examples of conductive oxides include $Fe_3O_4$, tin oxide doped to conduction, e.g., with indium and/or zinc, zinc oxide doped to conduction, e.g., with aluminum, zinc oxide, and sub-stoichiometric oxides, for example, of titanium and/or vanadium.

Also preferred are ceramic substrates, for example, silicon nitride and silicon carbide, and semiconductors, for example, germanium and semiconducting germanium-based compounds.

In general, an oxide surface is prepared prior to contact with the carrier by cleaning the surface to remove residual metals and organics, generally by an oxidation treatment followed by a water rinse. Oxide surfaces that are stable toward such treatment, for example, a single crystal or polycrystalline silicon wafer surface, the surface may be treated with the standard hydrogen peroxide/sulfuric acid "piranha" solution followed by a water rinse and a second treatment with a standard hydrogen peroxide/hydrochloric acid "buzzard" solution, in the manner typically followed for cleaning silicon wafers prior to fabricating integrated circuits on the wafer. In general, the process of the invention affords best results on oxide surfaces which are devoid of free base species, base (zero-valent) metals, and residual hydrocarbon species. However, even for surfaces which do not lend themselves to a rigorous cleaning to semiconductor standards, for example, conducting oxides, the process of the invention will still provide a coating layer which has good adhesion to the oxide surface upon which the coating layer is formed. Other cleaning methods applicable to particular surfaces for the removal of the unwanted species typical of those surfaces will be apparent to those of skill in the art.

Derivatizing the Phosphate-/Phosphonate-Based Coating Layer

As described above and in explained in detail in each of co-pending U.S. patent application Ser. No. 10/701,591, filed Nov. 4, 2003; Ser. No. 10/405,557, filed Apr. 1, 2003; and Ser. No. 10/179,743, filed Jun. 24, 2002, each of which is incorporated herein by reference in its entirety, when a phosphorous acid-based coating layer of the invention is prepared from a coating composition comprising a reactive or functionalized surface (e.g., a di- or polyfunctional phosphorous acid, such as an ω-functionalized phosphonic acid), the coating layer formed can be further derivatized with additional reagents. Non-limiting examples of such reagents include derivatizing the omega hydroxyl groups of a coating layer formed from an ω-hydroxy phosphonic acid with a protein coupling reagent and incorporating the hydroxyl groups of such a coating layer into an epoxy adhesive layer applied on top of the coating layer. Examples of protein coupling reagents include maleimido and succinimidyl coupling reagents. As described in the above-mentioned co-pending applications, and as will be appreciated, guided by the requirements for the coating layer and general chemical principals, numerous other derivatizing reactions can be carried out that utilize the reactive species available in the coating layer prepared using a phosphorous acids which includes one or more reactive substituents.

Such reactions can be employed to provide a pattern of the derivatized species on the surface of a coating layer provided by the present invention. For example, the above-described protein coupling reagent incorporated into a printing medium can be applied in a pattern to a coating layer prepared by the process of the invention utilizing a printing technique. Non-limiting examples of this include providing the coupling reagent in a medium suitable for delivery from an ink-jet printing device. When such patterns of derivatizing reagents are applied they can find utility in biosensor devices and in providing engineered biological structures for example, which can be utilized in implantable devices. It will be appreciated that other non-impact and impact printing techniques, for example, lithography, screen printing, stamping, and gravure printing can be adapted to provide patterns of derivatizing reagents on coating layers of the invention.

Patterning Oxide Surfaces

In accordance with the above described principles and methods, the coating process of the present invention can be used to provide a coating layer which is in a pattern on the oxide surface. Thus, a coating composition can be provided to the carrier in a pattern which will be transferred to the oxide surface when the carrier is contacted to an oxide surface under temperature conditions suitable to form a bond between the oxide surface and the coating composition. It will be appreciated that numerous means can be used to provide a pattern of coating composition on the carrier. Non-limiting examples include spraying a coating solution onto the carrier in only pre-determined areas, for example, by ink-jet printing and stenciling. Other methods may be found by adapting printing techniques, including stamping, lithographing, and gravure printing a coating solution onto the carrier in a pattern.

In the same manner, the carrier itself can be provided in the form of a pattern, for example, a stencil or a stamp. In this manner, when a coating composition is conveyed to an oxide surface the pattern of the carrier will transfer the coating composition to an oxide surface in a like pattern.

It will also be appreciated that when the carrier conveying a coating composition is in a form suitable for mechanical manipulation, e.g., in the form of a roller or ball, it can be mechanically directed in a pattern across an oxide surface to provide a coating layer having a pattern reflecting the path along which it was directed on the surface.

There follow many examples, e.g., one utilizing a carrier comprising a cotton pad to apply a coating of the present invention to the native oxide surface of a titanium coupon and to an oxide surface comprising silicon dioxide deposited on a flexible plastic sheet.

The following examples are intended to illustrate the process of the invention and the films formed thereby and are not meant to limit the scope of the invention. It will be appreciated that there are many modifications possible to the materials and process steps exemplified below which still fall within the scope of the inventive process and films.

Active Agents for Derivatized/Functionalized Surfaces

When desired, an active agent (or a combination of active agents) can be bound to the derivatized surface according to the invention in order to accomplish any of a variety of goals. The particular active agent(s) used, as well as the mechanism to chemically and/or physically attach the active agent(s) to the derivatized surface, will obviously depend upon the chemical and/or physical nature of the derivatization of the surface, e.g., its reactivity, its functionality, its surface roughness, etc. Nevertheless, the following list of active agents that are suitable for surface immobilization according to the invention is merely exemplary and should not be construed as being complete.

In one embodiment, the active agent can include antileukotrienes or leukotriene receptor antagonists (e.g., for B4, C4, D4, and/or E4 leukotriene receptors) including, but not limited to, zafirlukast, montelukast, pranlukast, iralukast, pobilukast, or the like, or sombinations thereof, and/or salts thereof (e.g., Montelukast sodium, which is commercially available under the tradename SINGULAIR®).

In another embodiment, the active agent can include antihistamines including, but not limited to, ethanolamines (e.g., diphenhydramine and/or salts including hydro-chloride, dimenhydrinate, carbinoxamine, clemastine and/or salts such as fumarate, bromodiphenhydramine and/or salts such as hydrochloride, phenyloloxamine, doxyl-amine, or the like, or other salts thereof, or combinations thereof), ethylenediamines (e.g., tripelennamine and/or salts such as hydrochloride, pyrilamine and/or salts such as maleate, antazoline and/or salts such as phosphate, methapyriline, or the like, or other salts thereof, or combinations thereof), alkylamines (e.g., chlorpheniramine and/or salts such as maleate, brompheniramine and/or salts such as maleate, dexchlorpheniramine and/or salts such as maleate, dimethindene and/or salts such as maleate, triprolidine and/or salts such as hydrochloride, pheniramine and/or salts such as maleate, or the like, or other salts thereof, or combinations thereof), piper-zines (e.g., cyclizine and/or salts such as hydrochloride and/or lactate, meclizine and/or salts such as hydrochloride, hydroxyzine and/or salts such as hydrochloride and/or pamoate, buclizine, chlorcyclizine, or the like, or other salts thereof, or combinations thereof), phenothiazines (e.g., promethazine and/or salts such as hydro-chloride, propiomazine, methdilazine, trimeprazine and/or salts such as tartrate, or the like, or other salts thereof, or combinations thereof), and/or miscellaneous others (e.g., cyproheptadine, ketotifen, azatadine and/or salts such as maleate, terfenadine, fexofenadine, astemizole, diphenylpyraline, phenindamine, or the like, or salts thereof, or combinations thereof).

In another embodiment, the active agent can include antiseptics including, but not limited to, iodine, chlorhexidine acetate, sodium hypochlorite, and calcium hydroxide.

In another embodiment, the active agent can include steroidal anti-inflammatory agents including, but not limited to, betamethasone, triamcinolone, dexamethasone, prednisone, mometasone, fluticasone, beclomethasone, flunisolide, budesonide, or the like, or salts thereof, or combinations thereof. In another embodiment, the active agent can include non-steroidal anti-inflammatory agents including, but not limited to, fenoprofen, flurbiprofen, ibuprofen, ketoprofen, naproxen, oxaprozin, diclofenac, etodolac, indomethacin, ketorolac, nabumetone, sulindac, tolmetin, meclofenamate, mefenamic acid, piroxicam, suprofen, or the like, or salts thereof, or combinations thereof.

In another embodiment, the active agent can include decongestants including, but not limited to, ephedrine, phenylpropanolamine, pseudoephedrine, phenylephrine, epinephrine, ephedrine, desoxyephedrine, naphazoline, oxymetazoline, tetrahydrozoline, xylometazoline, propylhexedrine, or the like, or salts thereof, or combinations thereof.

In another embodiment, the active agent can include mucolytics including, but not limited to, acetylcysteine, dornase alpha, or the like, or salts thereof, or combinations thereof.

In another embodiment, the active agent can include anticholinergics including, but not limited to, ipratropium, atropine, scopolamine, or the like, or salts thereof, or combinations thereof.

In another embodiment, the active agent can include non-antibiotic antimicrobials including, but not limited to, taurolidine or the like.

In another embodiment, the active agent can include mast cell stabilizers including, but not limited to, cromolyn, nedocromil, ketotifen, salts thereof (e.g., sodium), or combinations thereof.

In another embodiment, the active agent can include one or more active ingredients such as anti-infective agents, anti-inflammatory agents, mucolytic agents, antihistamines, anti-leukotrienes, decongestants, anticholinergics, antifungals, and combinations of these classes of agents. Anti-infective agents contemplated by the present invention include, but are not limited to antibiotics, anti-virals, non-antibiotic antimicrobials, and antiseptics. Anti-inflammatory agents contemplated by the present invention include, but are not limited to steroidal and non-steroidal anti-inflammatory agents, and mast cell inhibitors. Antifungal agents contemplated by the present invention include, but are not limited to amphotericin B, and azole antifungals. Examples of contemplated antibiotics include, but are not limited to cefuroxime, ciprofloxacin, tobramycin, cefoperazone, erythromycin, and gentamycin. Exemplary medications and doses that may be used in the methods according to the present invention are listed in Table 1.

TABLE 1

Active agents and dosages

| Generic Name | Brand Name | Class | Exemplary Range | Alternate Exemplary Range | Alternate Exemplary Range |
|---|---|---|---|---|---|
| Acetylcysteine | Mucomist Mucosil | Mucolytics | 125-500 mg | 150-450 mg | 200-400 mg |
| Amikacin | Amikin | Aminoglycoside | 50-500 mg | 75-300 mg | 100-200 mg |
| Amphotericin B | Fungizone | Antifungal | 2.5-45 mg | 4-30 mg | 7.5-15 mg |
| Atropine | | Anticolinergic | 10-700 mcg | 25-400 mcg | 75-300 mcg |
| Azelastine | Astelin | Antihistamine | 137-1096 mcg | 204-822 mcg | 382-616 mcg |
| Azithromycin | Zithromax | Macrolide | 50-400 mg | 75-300 mg | 150-200 mg |
| Aztreonam | Azactam | Monobactam | 250-1000 mg | 300-900 mg | 475-750 mg |
| Beclamethasone | Vanceril Beclovent | Steroidal Anti-inflammatory | 0.1-4 mg | 0.2-3 mg | 0.2-2 mg |
| Betamethasone | Celestone | Steroidal Anti-inflammatory | 0.1-4 mg | 0.2-3 mg | 0.2-2 mg |
| Cefazolin | Ancef, Kefzol | Cephlasporin (Gen I) | 250-1000 mg | 300-900 mg | 575-700 mg |

TABLE 1-continued

Active agents and dosages

| Generic Name | Brand Name | Class | Exemplary Range | Alternate Exemplary Range | Alternate Exemplary Range |
|---|---|---|---|---|---|
| Cefepime | Maxipime | Cephlasporin (Gen IV) | 125-1000 mg | 200-900 mg | 575-700 mg |
| Cefonicid | Moniacid | Cephlasporin (Gen II) | 250-1000 mg | 300-900 mg | 575-700 mg |
| Cefoperazone | Cefobid | Cephlasporin (Gen III) | 250-1000 mg | 300-900 mg | 575-700 mg |
| Cefotaxime | Claforan | Cephlasporin (Gen III) | 250-1000 mg | 300-900 mg | 575-700 mg |
| Cefotetan | Cefotan | Cephlasporin (Cephamycin) | 250-1000 mg | 300-900 mg | 575-700 mg |
| Cefoxitin | Mefoxin | Cephlasporin (Cephamycin) | 250-1000 mg | 300-900 mg | 575-700 mg |
| Ceftazidime | Fortaz, Ceptaz | Cephlasporin (Gen III) | 250-1000 mg | 300-900 mg | 475-750 mg |
| Ceftizoxime | Cefizox | Cephlasporin (Gen III) | 250-1000 mg | 300-900 mg | 575-700 mg |
| Ceftriaxone | Rocephin | Cephlasporin (Gen III) | 250-1000 mg | 300-900 mg | 575-700 mg |
| Cefuroxime | Ceftin | Cephlasporin (Gen II) | 100-600 mg | 200-520 mg | 250-400 mg |
| Cephapirin | Cefadyl | Cephlasporin (Gen I) | 250-1000 mg | 300-900 mg | 575-700 mg |
| Ciprofloxacin | Cipro | Quinolone | 25-200 mg | 50-175 mg | 75-110 mg |
| Clindamycin | Cleocin | Lincosamide | 50-600 mg | 75-500 mg | 125-300 mg |
| Cromolyn Sodium | Intal/Nasalcrom | Mast cell stabilizer | 5-100 mg | 7.5-75 mg | 10-50 mg |
| Dexamethasone | Decadron | Steroidal Anti-inflammatory | 0.1-4 mg | 0.2-3 mg | 0.2-2 mg |
| Dornase alpha | Pulmozyme | Mucolytic | 0.5-5 mg | 1-4 mg | 2-3 mg |
| Doxycycline | Vibramycin | Tetracycline | 10-100 mg | 15-80 mg | 25-65 mg |
| Erythromycin Lactobionate | Erythrocin | Macrolide | 50-600 mg | 60-350 mg | 100-300 mg |
| Fluconazole | Diflucan | Antifungal | 12.5-150 mg | 20-70 mg | 25-50 mg |
| Flunisolide | Aerobid Nasalide | Steroidal Anti-inflammatory | 0.1-4 mg | 0.2-3 mg | 0.2-2 mg |
| Flurbiprofen | Ocufen | Nonsteroidal Anti-inflammatory | 0.01-2 mg | 0.05-1 mg | 0.1-0.5 mg |
| Fluticasone | Flonase | Steroidal Anti-inflammatory | 10-700 mcg | 25-400 mcg | 75-300 mcg |
| Gentamycin | Garamycin | Aminoglycoside | 10-200 mg | 30-150 mg | 80-120 mg |
| Ibuprofen | Motrin | Nonsteroidal Anti-inflammatory | 25-400 mg | 30-300 mg | 50-150 mg |
| Ipratropium | Atrovent | Anticholinergic | 10-700 mcg | 25-400 mcg | 75-300 mcg |
| Itraconazole | Sporanox | Antifungal | 12.5-150 mg | 20-70 mg | 25-50 mg |
| Ketorolac | Acular | Nonsteroidal Anti-inflammatory | 0.05-4 mg | 0.1-2 mg | 0.3-1 mg |
| Levofloxacin | Levaquin | Quinolone | 40-200 mg | 50-150 mg | 60-80 mg |
| Linezolid | Zyvox | Miscellaneous anti-bacterial | 50-600 mg | 75-450 mg | 100-300 mg |
| Loratidine | Claritin | Antihistamine | 0.5-10 mg | 1-7.5 mg | 1-5 mg |
| Meropenem | Merrin | Carbapenem | 200-750 mg | 250-700 mg | 300-500 mg |
| Mezlocillin | Mezlin | Penicillin | 300-1500 mg | 375-1000 mg | 750-950 mg |
| Miconazole | Monistat | Antifungal | 12.5-300 mg | 30-200 mg | 50-100 mg |
| Montelukast | Singulair | Antileukotriene | 0.5-15 mg | 2-25 mg | 3-15 mg |
| Mupirocin | Bactroban | Antibacterial | 1-25 mg | 1.5-20 mg | 2-15 mg |
| Nafcillin | Unipen | Penicillin | 250-1000 mg | 300-900 mg | 575-700 mg |
| Nedocromil | Tilade | Mast cell stabilizer | 1-25 mg | 3-15 mg | 5-12 mg |
| Ofloxacin | Floxin | Quinolone | 25-200 mg | 50-175 mg | 75-110 mg |
| Oxacillin | Prostaphlin | Penicillin | 250-1000 mg | 300-900 mg | 575-700 mg |
| Oxymetazoline | Afrin | Decongestant | 0.05-0.5 mg | 0.075-0.4 mg | 0.1-0.3 mg |
| Phenylepherine | Neo-Synephrine | Decongestant | 5-50 mg | 10-35 mg | 15-20 mg |
| Piperacillin | Pipracil | Penicillin | 100-1000 mg | 125-750 mg | 250-600 mg |
| Potassium Iodide | — | Antiseptic | 30-200 mg | 40-150 mg | 50-80 mg |
| Rifampin | Rifadin | Miscellaneous | 500-5000 mg | 1000-4000 mg | 1500-3500 mg |
| Taurolin | Taurolidine | Non antibiotic antimicrobial | 5-200 mg | 20-150 mg | 40-120 mg |
| Tetrahydrozolidine | Tizine | Decongestant | 0.05-0.5 mg | 0.06-0.4 mg | 0.1-0.3 mg |
| Ticarcillin + Clavulanate | Timentin | Penicillin | 500-5000 mg | 1000-4000 mg | 1500-3500 mg |

TABLE 1-continued

Active agents and dosages

| Generic Name | Brand Name | Class | Exemplary Range | Alternate Exemplary Range | Alternate Exemplary Range |
|---|---|---|---|---|---|
| Tobramycin | Nebcin | Aminoglycoside | 10-200 mg | 30-150 mg | 80-120 mg |
| Triamcinalone | Asthmacor Aristocort | Steroidal Anti-inflammatory | 0.05-3 mg | 0.2-2.5 mg | 0.5-2 mg |
| Vancomycin | Vancocin | Antibiotic - miscellaneous | 50-400 mg | 75-325 mg | 125-250 mg |
| Xylometazoline | Otrivin | Decongestant | 0.05-0.4 mg | 0.075-0.3 mg | 0.1-0.2 mg |
| Zafirlukast | Accolate | Antileukotriene | 2-60 mg | 4-50 mg | 6-30 mg |

Exemplary anti-infective agents include, but are not limited to, penicillins, cephalosporins, macrolides, ketolides, sulfonamides, quinolones, aminoglycosides, beta lactam antibiotics, and linezolid. Exemplary non-antibiotic antimicrobials include taurolidine. Exemplary steroidal anti-inflammatory agents include glucocorticoids. Exemplary non-steroidal anti-inflammatory agents include diclofenac. Exemplary mast cell stabilizers include cromolyn and nedcromil sodium. Exemplary mucolytic agents are acetylcysteine and dornase alpha. Exemplary decongestants are phenyl-ephrine, naphazoline, oxymetazoline, tetrahydrozoline and xylometoazoline. Exemplary antihistamines include loratidine. Exemplary antibiotic combinations include cefuroxime and gentamicin. Exemplary anticholinergics include ipratropium, atropine and scopolamine. Exemplary antifungals include amphotericin B, itraconazole, fluconazole, and miconazole.

In another embodiment, the active agent can include, but are not limited to, anti-inflammatory agents (e.g., alclometasone, amcinonide, amlexanox, balsalazide, betamethasone, celecoxib, choline magnesium, trisalicylate, choline salicylate, chlobetasol, colchicine, cortisone acetate, curcumin, disunite, dexamethasone, diclofenac, diflunisal, etodolac, fenoprofen, fluocinolone, fluometholone, flurandrenolide, flurandrenolide, flurbiprofen, hydrocortisone, ibuprofen, indomethacin, ketoprofen, ketorolac, meclofenamate, mefenamic acid, meloxicam, mesalamine, Methylprednisolone, nabumetone, naproxen, olsalazine, oxaprozin, piroxicam, prednisone, rofecoxib, salsalate, sulfasalazine, sulindac, tolmetin, triamcinolone, valdecoxiband, analogs/derivatives thereof, salts thereof, or combinations thereof), immunosuppressants (e.g., azathioprine, basiliximab, cyclosporine, daclizumab, leflunomide, lymphocyte immune globulin, methotrexate, muromonab-CD3, mycophenolate, sirolimus, tacrolimus, thalidomideand, analogs/derivatives thereof, salts thereof, or combinations thereof), anti-cell proliferation agents (e.g., alkylating agents such as busulfan, cisplatin, cyclophosphamide, oxaliplatin, or the like; nitrosourea compounds such as in carmustine, lomustine, or the like; anthracycline compounds such as epirubicin, mitoxantrone, or the like; anti-androgen compounds such as bicalutamide, flutamide, nilutamide, or the like; antibiotics such as bleomycin, dactinomycin, mitomycin, or the like; anti-metabolite compounds such as cladribine, fluorouracil, gemcitabine, hydroxyurea, methotrexate, or the like; anti-microtubular compounds such as docetaxel, paclitaxel, or the like; aromatase inactivators such as anastrozole, exemestane, or the like; hormones such as estramumustine, megestrol, or the like; monoclonal antibody compounds such as alemtuzumab, rituximab, or the like; protein synthesis inhibitors such as asparaginase, pegaspargase, or the like; other compounds such as carboplatin, dipyridamole, doxorubin, doxorubicin, etopo-side, ima- tinib, misonidazole, mercaptopurine, testolactone, trimetrexate, glucuronate, tiripazamine, topotecan, vindesine, vincristine, analogs/derivatives thereof, salts thereof, or combinations thereof), anti-thromosis, anti-platelet, and/or fibrinolysis agents (e.g., abcimab, antithrombin III, argatroban, aspirin, clopidogrel, dipyridamole, eptifibatide, fondaparinux, heparin, low molecular weight heparin, recombinant hirudin such as bivalirudin, lepirudin, or the like, ticlopidine, tissue recombinant plasminogen activators such as alteplase, reteplase, streptokinase, tenecteplase, urokinase, or the like, tirofibanand, analogs/derivatives thereof, salts thereof, or combinations thereof), extracellular matrix mediators (e.g., calprotectin, catechins, sulfonylated amino acid hydroxamates, tetracycline compounds such as demeclo-cycline, doxycycline, minocycline, oxytetracycline, tetracycline, or the like, analogs or derivatives thereof, salts thereof, or combinations thereof), and the like, and combinations thereof.

In another embodiment, the active agent can include, but are not limited to, anti-thrombotic agents such as heparin, heparin derivatives, urokinase, PPack (dextro-phenylalanine proline arginine chloromethylketone), or the like, analogs/derivatives thereof, salts thereof, or combinations thereof; steroidal and non-steroidal anti-inflammatory agents (NSAIDs) such as dexamethasone, prednisolone, cortico-sterone, hydrocortisone and budesonide estrogen, sulfasalazine and mesalamine, salicylic acid, salicylates, ibuprofen, naproxen, sulindac, diclofenac, piroxicam, ketoprofen, diflunisal, nabumetone, etodolac, oxaprozin, indomethacin, or the like, analogs/derivatives thereof, salts thereof, or combinations thereof; anti-neoplastic or anti-proliferative or anti-mitotic agents such as paclitaxel, 5-fluorouracil, cisplatin, vinblastine, vincristine, epothilones, endostatin, angiostatin, doxorubicin, metho-trexate, angiopeptin or the like, analogs/derivatives thereof, salts thereof, or combinations thereof, monoclonal antibodies capable of blocking smooth muscle cell proliferation, thymidine kinase inhibitors, or the like, analogs/derivatives thereof, salts thereof, or combinations thereof; anesthetic agents such as lidocaine, bupivacaine, ropivacaine, or the like, analogs/derivatives thereof, salts thereof, or combinations thereof; anti-coagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors, tick antiplatelet peptides, or the like, analogs/derivatives thereof, salts thereof, or combinations thereof; vascular cell growth promoters such as growth factors, transcriptional activators, translational promoters, or the like, analogs/derivatives thereof, salts thereof, or combinations thereof; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, or the like, analogs/derivatives thereof, salts thereof, or combinations thereof; protein kinase and tyrosine kinase inhibitors such as tyrphostins, genistein, quinoxalines, or the like, analogs/derivatives thereof, salts thereof, or combinations thereof; prostacyclin analogs; cholesterol-lowering agents; angiopoietins; antimicrobial agents such as triclosan, cephalosporins, β-lactams, aminoglycosides, nitrofurantoin, or the like, analogs/derivatives thereof, salts thereof, or combinations thereof; cytotoxic agents; cytostatic agents; cell proliferation affectors; vasodilating agents; agents that interfere with endogenous vascoactive mechanisms; analogs/derivatives thereof; salts thereof; metabolites thereof; or combinations thereof.

Exemplary genetic active agents include, but are not limited to, anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Such molecules include any of the "hedgehog" proteins, or the DNA's encoding them.

Vectors of interest for delivery of genetic active agents include, but are not limited to, (a) plasmids, (b) viral vectors such as adenovirus, adeno-associated virus, lentivirus, or the like, and (c) non-viral vectors such as lipids, liposomes, cationic lipids, or the like.

Cells include cells of human origin (autologous or allogenic), including stem cells, or from an animal source (xenogenic), which can be genetically engineered if desired to deliver proteins of interest.

Non-limiting examples of useful antimicrobial agents include: Antiamebics, e.g., Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Diphetarsone, Emetine, Fumagillin, Glaucarubin, Glycobiarsol, 8-Hydroxy-7-iodo-5-quinoline-sulfonic Acid, Iodochlorhydroxyquin, Iodoquinol, Paromomycin, Phanqui-none, Polybenzarsol, Propamidine, Quinfamide, Scenidazole, Sulfarside, Teclozan, Tetracycline, Thiocarbamizine, Thiocarbarsone, Timidazole; Antibiotics, e.g. Amino-glycosides (such as Amikacin, Apramycin, Arbekacin, Bambermycins, Butirosin, Dibekacin, Dihydrostreptomycin, Fortimicin(s), Gentamicin, Isepamicin, Kaniamycin, Micronomicin, Neomycin, Neomycin Undecylenate, Netilmicin, Paromomycin, Ribostamycin, Sisomicin, Spectinomycin, Streptomycin, Tobramycin, Trospectomycin, and the like), Amphenicols (such as Azidamfenicol, Chloramphenicol, Florfenicol, Thiamphenicol, and the like), Ansamycins (such as Rifamide, Rifampin, Rifamycin, Rifapentine, Rifaximin, and the like), β-Lactams (e.g., Carbacephems, Loracarbef, Carbapenems (such as Biapenem, Imipenem, Meropenem, Panipenem, and the like), Cephalosporins (such as Cefaclor, Cefadroxil, Cefamandole, Cefatrizine, Cefazedone, Cefazolin, Cefcapene Povoxil, Cefclidin, Cefdinir, Cefditoren, Cefe-pime, Cefetamet, Cefixime, Cefinenoxine, Cefodizime, Cefonicid, Cefoperazone, Ceforanide, Cefotaxime, Cefotiam, Cefozopran, Cefpimizole, Cefpiramide, Cefpirome, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin, and the like), Cepha-mycins (such as Cefbuperazone, Cefinetazole, Cefminox, Cefotetan, Cefoxitin, and the like), Monobactams (such as Aztreonam, Carumonam, Tigemonam, and the like), Oxacephens (such as Flomoxef, Moxalactam, and the like), Penicillins (such as Amdinocillin, Amdinocillin Pivoxil, Amoxicillin, Ampicillin, Apalcillin, Aspoxicillin, Azidocillin, Azlocillin, Bacampicillin, Benzylpenicillic Acid, Benzylpenicillin Sodium, Carbenicillin, Carindacillin, Clometocillin, Cloxacillin, Cyclacillin, Dicloxacillin, Epi-cillin, Fenbenicillin, Floxacillin, Hetacillin, Lenampicillin, Metampicillin, Methicillin Sodium, Mezlocillin, Naacillin Sodium, Oxacillin, Penamecillin, Penethamate Hydro-iodide, Penicillin G Benethamine, Penicillin G Benzathine, Penicillin G Benzhydryl-amine, Penicillin G Calcium, Penicillin G Hydrabamine, Penicillin G Potassium, Penicillin G Procaine, Penicillin N, Penicillin 0, Penicillin V, Penicillin V Benzathine, Penicillin V Hydrabamine, Penimepicycline, Phenethicillin Potassium, Piperacillin, Pivampicillin, Propicillin, Quinacillin, Sulbenicillin, Sultamicillin, Talampicillin, Temo-cillin, Ticarcillin, and the like), Ritipenem, Lincosamides (such as Clindamycin, Linco-mycin, and the like), Macrolides (such as Azithromycin, Capbomycin, Clarithromycin, Dirithromycin, Erythromycin, Erythromycin Acistrate, Erythromycin Estolate, Erythro-mycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin, and the like), Polypeptides (such as Amphomycin, Bacitracin, Capreomycin, Colistin, Enduracidin, Enviomycin, Fusafungine, Gramicidin S, Gramicidin(s), Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin, and the like), Tetracyclines (such as Apicycline, Chlortetracycline, Clomocycline, Demeclocycline, Doxycycline, Guamecycline, Lymecycline, Meclocycline, Methacycline, Minocycline, Oxytetracycline, Penimepi-cycline, Pipacycline, Rolitetracycline, Sancycline, Tetracycline, and the like), Cycloserine, Mupirocin, Tuberin; synthetic antibacterial agents, e.g. 2,4-Diaminopyrimi-dines (such as Brodimoprim, Textroxoprim, Trimethoprim, and the like), Nitrofurans (such as Furaltadone, Furazolium Chloride, Nifuradene, Nifuratel, Nifurfoline, Nifur-pirinol, Nifurprazine, Nifurtoinol, Nitrofurantoin, and the like), Quinolones and Analogs (such as Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nadilixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin, and the like), Sulfonamides (such as Acetyl Sulfamethoxpyrazine, Benzylsulfamide, Chloramine-B, Chloramine-T, Dichloramine T, N2-Formylsulfi-somidine, N4-ÿ-D-Glucosylsulfanil-amide, Mafenide, 4'-(Methylsulfamoyl)sulfanil-anilide, Noprylsulfamide, Phthalylsulfacetamide, Phthalylsulfathiazole, Salazo-sulfadimidine, Succinylsulfathiazole, Sulfabenzamide, Sulfacetamide, Sulfachlor-pyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfa-methomidine, Sulfamethoxazole, Sulfamethoxypyridazine, Sulfametrole, Sulfamido-chrysoidine, Sulfamoxole, Sulfanilamide, 4-Sulfanilamidosalicylic Acid, N4-Sulfanilyl-sulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfa-symazine, Sulfathiazole, Sulfathiourea, Sulfatolamide, Sulfisomidine, Sulfisoxazole, and the like), Sulfones (such as Acedapsone, Acediasulfone, Acetosulfone Sodium, Dapsone, Diathymosulfone, Glucosulfone Sodium, Solasulfone, Succisulfone, Sulf-anilic Acid, p-Sulfanilylbenzylamine, Sulfoxone Sodium, Thiazolsulfone, and the like), Clofoctol, Hexedine, Methenamine, Methenamine Anhydromethylenecitrate, Methen-amine Hippurate, Methenamine Mandelate, Methenamine Sulfosalicylate, Nitroxo-line, Taurolidine, Xibomol, and the like; leprostatic antibacterial agents, such as Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium, and the like, antifungal agents such as Allylamines Butenafine, Naftifine, Terbinafine, Imidazoles (e.g., Bifonazole, Butoconazole, Cholordantoin, Chlormid-azole, Cloconazole, Clotrimazole, Econazole, Enilconazole, Fenticonazole, Flutrim-azole, Isoconazole, Ketoconazole, Lanoconazole, Miconazole, Omoconazole, Oxiconazole Nitrate, Sertaconazole, Sulconazole, Tioconazole, and the like), Thiocarbamates (e.g., Tolcilate, Tolindate, Tolnaftate, and the like), Triazoles (e.g., Fluconazole, Itraconazole, Saperconazole, Terconazole, and the like), Acrisorcin, Amorolfine, Biphenamine, Bromosalicylchloranilide, Buclosamide, Calcium Propio-nate, Chlorphenesin, Ciclopirox, Cloxyquin, Coparaffinate, Diamthazole Dihydro-chloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, Zinc Propionate, etc.; or the like; analogs/derivatives thereof; salts thereof; or combinations thereof.

Other antimicrobial agents useful in the present invention include, but are not limited to, Q-lactamase inhibitors (e.g. Clavulanic Acid, Sulbactam, Tazobactam, and the like); Chldramphenicols (e.g. Azidamphenicol, Chloramphenicol, Thiaphenicol, and the like); Fusidic Acid; synthetic agents such as Trimethoprim, (optionally in combination with sulfonamides) Nitroimidazoles (e.g., Metronidazole, Timidazole, Nimor-azole, and the like), and the like; Antimycobacterial agents (e.g., Capreomycin, Clofazimine, Dapsone, Ethambutol, Isoniazid, Pyrazinamide, Rifabutin, Rifampicin, Streptomycin, Thioamides, and the like); Antiviral agents (e.g., Acryclovir, Amanta-dine, Azidothymidine, Ganciclovir, Idoxuridine, Tribavirin, Trifluridine, Vidarabine, and the like); Interferons; antiseptic agents (e.g., Chlorhexidine, Gentian violet, Octenidine, Povidone Iodine, Quaternary ammonium compounds, Silver sulfadi-azine, Triclosan, and the like); or the like; analogs/derivatives thereof; salts thereof; or combinations thereof.

In some embodiments, the active agent may include, but is not limited to, collagen (e.g., Type 1), osteonectin, bone sialoproteins (Bsp), alpha-2HS-glycoproteins, bone Gla-protein (Bgp), matrix Gla-protein, bone phosphoglycoprotein, bone phosphor-protein, bone proteoglycan, protolipids, bone morphogenic proteins (e.g., BMP-1, -2A, -2B, -3, -3b, -4, -5, -6, -7, -8, -8b, -9, -10, -11, -12, -13, -14, -15), cartilage induc-tion factor, platelet derived growth factor (PDGF-1, -2), endothelial cell growth factors (ECGF-1, -2a, -2b), skeletal growth factor (SKF=IGF-2), insulin-like growth factors (IGF-1, IGF-2), fibroblast growth factor (ODGF-I, -2, -3, -4, -5, -6, -7, -8, -9, -10, -11, -12, -13, -14, -15, -16, -17, -18, -19, -20, -21, -22, -23), colony stimulating factor, transforming growth factor (e.g., TGF-α, TGF-β, or the like), vascular endothelial growth factors (VEGF), growth/differentiation factors (GDF-1, -3, -5, -6, -7, -8, -9, -9B, -10, -11, -15, -16), osteogenic proteins (OP-1=BMP-7, OP-2=BMP-8, OP-3=BMP-8b), bone growth hormone, parathyroid hormone (PTH), insulin, calcitonin, and the like, and combinations thereof. Additionally or alternately, the active agents may include proteins associated with cartilage, such as chondrocalcining protein; proteins associated with dentin, such as phosphophoryn, glycoproteins and Gla proteins; proteins associated with enamel such as amelognin and enamelin; structural proteins such as fibrin, fibrinogen, keratin, tubulin, elastin, and the like; blood proteins, whether in plasma or serum, e.g., serum albumin; non-protein growth factors such as prostaglandins and statins (e.g., Simvastatin, Lovastatin, or the like); or the like; analogs/derivatives thereof; salts thereof; or combinations thereof.

In another embodiment, the active agent can include amino acids, anabolics, analgesics and antagonists, anesthetics, angiogenesis agents, anti-angiogenetic agents, antihelmintics, anti-adrenergic agents, anti-asthmatics, anti-atherosclerotics, antibacterials, anticholesterolics, anticholinergics, anti-coagulants, antidepressants, antidotes, anti-emetics, anti-epileptic drugs, anti-fibrinolytics, antihistamines, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media and radio-isotopes), drugs for treatment of chronic alcoholism, drugs targeting dopaminergic pathways, electrolytes, enzymes, enzyme inhibitors, ferments, ferment inhibitors, gangliosides and ganglioside derivatives, hemostatics, hormones, hormone antagonists, hypnotics, immunomodulators, immunostimulants, immuno-suppressants, minerals, muscle relaxants, neuromodulators, neurotransmitters and neurotropics, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vaso-protectives, vectors for gene therapy, viral vaccines, viruses, vitamins, oligonucleotides and derivatives, or the like, or analogs/derivatives thereof, salts thereof, and/or combinations thereof.

In another embodiment, the active agent can include antimicrobial agents, analgesics, antiinflammatory agents, counter irritants coagulation modifying agents, diuretics, sympathomimetics, anorexics, antacids and other gastrointestinal agents, antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhytmics, contrast materials, radiopharmaceuticals, antiallergic agents, tranquilizers, vasodilators, antiviral agents, and antineoplastic or cytostatic agents or other agents with anticancer properties, vitamins (including micro- and macro-nutrients), or a combination thereof.

In another embodiment, the active agent includes an anti-muscle spasm agent, anti-spasmodic, bone resorption inhibitor, smooth muscle contractile agent, calcium absorption enhancer, muscle relaxant, or a mixture thereof. Suitable anti-muscle spasm agents include, but are not limited to, baclofen, botulinum toxin, carisoprodol, chlorphenesin, chlorzoxazone, cyclobenzaprine, dantrolene, diazepam, metaxalone, methocarbamol, orphenadrine, tizanidine, and mixtures thereof. Suitable anti-spasmodics include, but are not limited to, atropine, baclofen, dicyclomine, hyoscine, propatheline, oxybutynin, S-oxybutynin, tizanidine, cevimeline, chlordiazepoxide, hydrochloride, dicyclomine, hyoscine, hyoscyamine, glycopyrrolate, and mixtures thereof. Suitable bone resorption inhibitors include, but are not limited to alendron-ate, ibandronate, minodronate, risedronate, etidronate, tiludronate, and mixtures thereof. A suitable smooth muscle contractile agent includes, but is not limited to, hyoscine, and mixtures thereof. Suitable calcium absorption enhancers include, but are not limited to, alfacalcidol, calcitriol, and mixtures thereof. Suitable muscle relax-ants include, but are not limited to, baclofen, carisoprodol, chlorphenesin, chlorzoxa-zone, cyclobenzaprine, dantrolene, diazepam, metaxalone, methocarbamol, orphenadrine, and mixtures thereof.

In another embodiment, the active agent includes an anti-diuretic, anti-muscle spasm agent, anti-spasmodic, agent for treating urinary incontinence, anti-diarrheal agent, agent for treating nausea and/or vomiting, smooth muscle contractile agent, anti-secretory agent, enzyme, anti-ulcerant, bile acid replacement and/or gallstone solubilizing drug, or a mixture thereof. Suitable anti-diuretics include, but are not limited to, acetazolamide, benzthiazide, bendroflumethazide, bumetanide, chlorthali-done, chlorothiazide, ethacrynic acid, furosemide, hydrochlorothiazide, hydroflume-thiazide, methyclothiazide, polythiazide, quinethazone, spironolactone, triamterene, torsemide, trichlomethiazide, desmopressin, oxytocin, and mixtures thereof. Suitable anti-muscle spasm agents include, but are not limited to, baclofen, botulinum toxin, carisoprodol, chlorphenesin, chlorzoxazone, cyclobenzaprine, dantrolene, diazepam, metaxalone, methocarbamol, orphenadrine, tizanidine, and mixtures thereof. Suitable anti-spasmodics include, but are not limited to, atropine, baclofen, dicyclo-mine, hyoscine, propatheline, oxybutynin, S-oxybutynin, tizanidine, and mixtures thereof. Suitable agents for treating urinary incontinence include, but are not limited to, darifenacin, vamicamide, detrol, ditropan, imipramine, and mixtures thereof. Suitable anti-diarrheal agents include, but are not limited to, ondansetron, palno-setron, tropisetron, attapulgite, atropine, bismuth, diphenoxylate, loperamide, and mixtures thereof. Suitable agents for treating nausea and/or vomiting include, but are not limited to, alosetron, dolasetron, granisetron, meclizine, metoclopramide, ondansetron, palnosetron, prochloperazine, promethazine, trimethobenzamiode, tropisetron, and mixtures thereof. A suitable smooth muscle contractile agent includes, but is not limited to, hyoscine. Suitable anti-secretory agents include, but are not limited to, esomeprazole, lansoprazole, omeprazole, pantoprazole, rabepra-zole, tenetoprazole, ecabet, misoprostol, teprenone, and mixtures thereof. Suitable enzymes include, but are not limited to, alpha-galactosidase, alpha-L-iduronidase, imiglucerase/alglucerase, amylase, lipase, protease, pancreatin, olsalazine, and mixtures thereof. Suitable anti-ulcerants include, but are not limited to, cimetidine, ranitidine, famotidine, misoprostol, sucralfate, pantoprazole, lansoprazole, omepra-zole, and mixtures thereof. A suitable bile acid replacement and/or gallstone solubilizing drug includes, but is not limited to, ursodiol.

In another embodiment, the active agent includes an endocrine modulator, glucose production inhibitor, agent for treatment of type II diabetes, anti-secretory agent, glycolipid, glycoprotein, anti-hyperthyroid agent, thyroid hormone, or a mixture thereof. Suitable endocrine modulators include, but are not limited to, methimazole, voglibose, finasteride, GI198745, liothyronine, glyburide, metformin, nateglinide, ioglitazone, pegvisomant, minoxidil, and mixtures thereof. Suitable glucose production inhibitors include, but are not limited to, acarbose, acetohexamide, chlorpropamide, glipizide, glyburide, metformin, miglitol, nateglinide, pioglitazone, rosiglitazone, tolbutamide, tolazamide, and mixtures thereof. Suitable agents for treatment of type II diabetes include, but are not limited to, acarbose, acetohex-amide, chlorpropamide, glipizide, glyburide, metformin, miglitol, nateglinide, pioglit-azone, rosiglitazone, tolbutamide, tolazamide, and mixtures thereof. Suitable anti-secretory agents include, but are not limited to, esomeprazole, lansoprazole, omep-razole, pantoprazole, rabeprazole, tenetoprazole, ecabet, misoprostol, teprenone, and mixtures thereof. Suitable glycolipids include, but are not limited to imigulcer-ase, vancomycin, vevesca (OGT 918), GMK vaccine, and mixtures thereof. Suitable glycoproteins include, but are not limited to, staphvax, bimosiamose (TBC1269), GCS-100, heparin, and mixtures thereof. Suitable anti-hyperthyroid agents include, but are not limited to, methimazol, propylthiouracil, and mixtures thereof.

In another embodiment, the active agent includes a cholesterol-lowering agent, aldosterone antagonist, triglyceride-lowering agent, leukotriene receptor antagonist, immuno-modulator or immunogen, glucose production inhibitor, agent for treatment of type II diabetes, bone resorption inhibitor, calcium absorption enhancer, insulin enhancing agent, insulin sensitizer, cytokine, metabolic regulator, mast cell mediator, eosinophil and/or mast cell antagonist, glycolipid, glycoprotein, anti-inflammatory drug, anti-obesity drug, COX (cyclooxygenase) and/or LO (lipoxygenase) inhibitor, or a mixture thereof. Suitable cholesterol-lowering agents include, but are not limited to, atorvastatin, benzofibrate, bezafibrate, cerivastatin, cholestyramine, ciprofibrate, clofibrate, colesevelam, colestipol, ezetimibe, fluvastatin, gemfibrozil, lovastatin, niacin/lovastatin, pravastatin, probucol, rosuvastatin, and simvastatin. A suitable aldosterone antagonist includes, but is not limited to, spironolactone. A suitable triglyceride-lowering agent includes, but is not limited to, fenofibrate. Suitable immunomodulators or immunogens include, but are not limited to, interferon beta 1A, interferon beta 1B. Suitable glucose production inhibitors include, but are not limited to, acarbose, acetohexamide, chlorpropamide, glipizide, glyburide, metformin, miglitol, nateglinide, pioglitazone, rosiglitazone, tolbutamide, and tolazamide. Suitable insulin enhancing agents include, but are not limited to, acamprosate, miglitol, troglitazone, chlorpropamide, glimepiride, glipizide, glyburide, and repagli-nide. A suitable insulin sensitizer includes, but is not limited to, is BRL 49653. Suitable cytokines include, but are not limited to, darbepoetin alfa, epoetin alpha, erythropoietin, and NESP. Suitable metabolic regulators include, but are not limited to, allopurinol and oxypurinol. A suitable eosinophil and/or mast cell antagonists includes, but is not limited to, nedocromil. Suitable anti-inflammatory drugs include, but are not limited to, alosetron, anakinra, beclomethasone, betamethasone, budesonide, clobetasol, celecoxib, cromolyn, desoximetasone, dexamethasone, epinastic, etanercept, etoricoxib, flunisolide, fluocinonide, fluticasone, formoterol, hydrocortisone, hydroxychloroquine, ibudilast, ketotifen, meloxicam, mesalamine, methotrexate, methylprednisolone, mometasone, montelukast, nedocromil, olsala-zine, prednisone, ramatroban, rofecoxib, salsalate, terbutaline, triamcinolone, valde-coxib, and zafirlukast. Suitable anti-obesity drugs include, but are not limited to, dexedrine, diethylpropion, mazindol, oleoyl-estrone, phentermine, phendimetrazine, and sibutramine. A suitable COX and/or LO inhibitor includes, but is not limited to, is ML-3000.

In another embodiment, the active agent includes an anti-arrhythmic, anti-hypertensive, heart regulator, cardiovascular agent, plaque stabilization agent, vasodilator, anti-anginal, anti-coagulant, anti-hypotensive, anti-thrombotic, drug for treating congestive heart failure, p-FOX (fatty acid oxidation) inhibitor, or a mixture thereof. Suitable antiarrhythmics include, but are not limited to, adenosine, amioda-rone, bepridil, bretylium, digitoxin, digoxin, diltiazem, disopyramide, dofetilide, D-sotolol, flecamide, lidocaine, mexiletine, milrinone, phenyloin, pilsicamide, procain-amide, propafenone, propranolol, quinidine, tocamide, dofetilide, and mixtures thereof. Suitable anti-hypertensives include, but are not limited to, acebutolol, alfuzosin, amlodipine, atenolol, amlodipine/benazepril, barnidipine benazepril, bepridil, betaxolol, bisoprolol, bosentan, candesartan, captopril, cariporide, carvedilol, celiprolol, cilazapril, clonidine, diltiazem, doxazosin, enalapril, eplerenone, eprosartan, esmolol, felodipine, fenoldopam, fosinopril, guanfacine, imidapril, irbesartan, isradipine, labetalol, lercanidipine, lisinopril, losartan, manidipine, methyldopa, metoprolol, moxonidine, nadolol, nicardipine, nicorandal, nifedipine, nitrendipine, nosoldipine, omapatrilat, perindopril erbumine, pindolol, prazosin, propranolol, quinapril, ramipri, sotalol, spirapril, tamsulosin, telmisartan, terazosin, torsemide, trandolapril, valsartan, vatanidipine, midodrine, and mixtures thereof. Suitable heart regulators include, but are not limited to, digoxin, digitoxin, dobut-amine, and mixtures thereof. Suitable cardiovascular agents include, but are not limited to, edaravone, iloprost, levosimendan, molsidomine, tezosentan, tirilazad, YM087, adenosine, avasimibe, fenofibrate, and mixtures thereof. A suitable plaque stabilization agent includes, but is not limited to, avasimibe. Suitable vasodilators include, but are not limited to, buflomedil, cilostazol, dipyridamole, diazoxide, hydral-azine, minoxidil, naftidrofuryl, nicorandil, nitroprusside, alprostadil, apomorphine, phentolamine mesylate, sildenafil, tadalafil, vardenifil, and mixtures thereof. Suitable anti-anginals include, but are not limited to, amilodipine, amyl nitrite, atenolol, bepridil, diltiazem, erythrityl tetranitrate, felodipine, isosorbide dinitrate, isradipine, metoprolol, nadolol, nicardipine, nifedipine, nimodipine, pentaerythritol tetranitrate, propranolol, and mixtures thereof. Suitable anti-coagulants include, but are not limited to, abciximab, ardeparin, argatroban, bivalirudin, clopidogrel, dalteparin, danaparoid, desirudin, dipyridamole, enoxaparin, eptifibatide, fondaparinux, H376/95, lepirudin, melagatran, nadroparine, nafamostat mesilate, pentosan, pentoxifylline, reviparin, sarpogrelate, SNAC/SNAD-heparin, ticlopidine, tinzaparin, tirofiban, warfarin, and mixtures thereof. Suitable anti-hypotensives include, but are not limited to, midodrine, dobutamine, fludrocortisone, and mixtures thereof. Suitable anti-thrombotics include, but are not limited to, aspirin, abciximab, enoxaparin, integrelin, ticlopidine, and mixtures thereof. Suitable drugs for treating congestive heart failure include, but are not limited to, aminone, benazepril, bumetanide, captopril, digitoxin, digoxin, dobutamine, dopamine, enalapril, ethacrynic acid, fosino-pril, furosemide, hydralazine, lisinopril, milrinone, minoxidil, moexipril, quinapril, ramipril, torsemide, and mixtures thereof. A suitable p-FOX inhibitor includes, but is not limited to, ranolazine.

In another embodiment, the active agent includes an aldosterone antagonist, immunomodulator or immunogen, immunosuppressant, cytokine, leukotriene receptor antagonist, mast cell mediator, eosinophil and/or mast cell antagonist, mucolytic, glucocorticoid, glycolipid, or a mixture thereof. A suitable aldosterone antagonist includes, but is not limited to, spironolactone. Suitable immuno-suppressants include, but are not limited to, azathioprine, cyclophosphamide, cyclosporine, ERL 080, enlimomab, methotrexate, mitoxantrone, mycophenolate, mofetil, sirolimus, tacrolimus (FK-506), and mixtures thereof. Suitable mucolytics for use in the buccal sprays of the invention include, but are not limited to, ambroxol, bromhexin, fudostein, acetylcestine, and mixtures thereof.

In another embodiment, the active compound is a p-FOX (fatty acid oxidation) inhibitor, acetylcholinesterase inhibitor, nerve impulse inhibitor, anti-cholinergic, anti-convulsant, anti-psychotic, anxiolytic agent, dopamine metabolism inhibitor, agent to treat post stroke sequelae, neuroprotectant, agent to treat Alzheimer's disease, neurotransmitter, neurotransmitter agonist, sedative, agent for treating attention deficit disorder, agent for treating narcolepsy, central adregenic antagonist, anti-depression agent, agent for treating Parkinson's disease, benzodiazepine antagonist, stimulant, neurotransmitter antagonist, tranquilizer, or a mixture thereof. Suitable acetylcholinesterase inhibitors include, but are not limited to, galantamine, neostig-mine, physostigmine, and edrophonium. Suitable nerve impulse inhibitors include, but are not limited to, levobupivacaine, lidocaine, prilocalne, mepivacaine, propofol, rapacuronium bromide, ropivacaine, tubocurarine, atracurium, doxaurium, miva-curium, pancuronium, vercuronium, pipecuronium, and rocuronium. Suitable anti-cholinergics for use in the buccal sprays of the invention include, but are not limited to, amantadine, ipratropium, oxitropium, and dicycloverine. Suitable anti-convulsants include, but are not limited to, acetazolamide, carbamazepine, clonazepam, diazepam, divalproex (valproic acid), ethosuximide, lamotrignine acid, levetriacetam, oxcarbazepine, phenobarbital, phenyloin, pregabalin, primidone, remacemide, trimethadione, topiramate, vigabatrin, and zonisamide. Suitable anti-psychotics include, but are not limited to, amisulpride, aripiprazole bifemelane, bromperidol, clozapine, chlorpromazine, haloperidol, iloperidone loperidone, olanzapine, quetiapine, fluphenazine, fumarate, risperidone, thiothixene, thioridazine, sulpride, and ziprasidone. Suitable anxiolytic agents include, but are not limited to, amitrypti-line, atracurium, buspirone, chlorzoxazone, clorazepate, cisatracurium, cyclobenza-prine, eperisone, esopiclone, hydroxyzine, mirtazapine, mivacurium, pagoclone, sulperide, zaleplon, and zopiclone. Suitable dopamine metabolism inhibitors include, but are not limited to, entacapone, lazebemide, selegiline, and tolcapone. Suitable agents to treat post stroke sequelae include, but are not limited to, glatiramer, interferon beta 1A, interferon beta 1B, estradiol, and progesterone. Suitable neuron-protectants include, but are not limited to, donepezil, memanine, nimodipine, riluzole, rivastigmine, tacrine, TAK147, and xaliproden. Suitable agents to treat Alzheimer's disease include, but are not limited to, carbidopa, levodopa, tacrine, donezepil, rivastigmine, and galantamine. Suitable neurotransmitters include, but are not limited to, acetylcholine, serotonin, 5-hydroxytryptamine (5-HT), GABA, glutamate, aspartate, glycine, histamine, epinephrine, norpinephrine, dopamine, adenosine, ATP, and nitric oxide. Suitable neurotransmitter agonists include, but are not limited to, almotriptan, aniracetam, atomoxetine, benserazide, bromocriptine, bupropion, cabergoline, citalopram, clomipramine, desipramine, diazepam, dihydroergotamine, doxepin duloxetine, eletriptan, escitalopram, fluvoxamine, gabapentin, imipramine, moclobemide, naratriptan, nefazodone, nefiracetam acamprosate, nicergoline, nortryptiline, paroxetine, pergolide, pramipexole, rizatriptan, ropinirole, sertraline, sibutramine, sumatriptan, tiagabine, trazodone, venlafaxine, and zolmitriptan. Suitable sedatives include, but are not limited to, dexmedetomidine, eszopiclone, indiplon, zolpidem, and zaleplon. Suitable agents for treating attention deficit disorder include, but are not limited to, amphetamine, dextroamphetamine, methyl-phenidate, and pemoline. Suitable agents for treating narcolepsy include, but are not limited to, modafinil and mazindol. A suitable central adregenic antagonist includes, but is not limited to, mesoridazine. Suitable anti-depression agents include, but are not limited to, amitriptyline, amoxapine, bupropion, clomipramine, clomipramine, clorgyline, desipramine, doxepin, fluoxetine, imipramine, isocarboxazid, maprotiline, mirtazapine, nefazodone, nortriptyline, paroxetine, phenelzine, protriptyline, sertraline, tranylcypromine, trazodone, and venlafaxine. Suitable agents for treating Parkinson's disease include, but are not limited to, amantadine, bromocriptine, carvidopa, levodopa, pergolide, and selegiline. A suitable benzo-diazepine antagonist includes, but is not limited to, flumazenil. A suitable neurontransmitter antagonist includes, but is not limited, to deramciclane. Suitable stimulants include, but are not limited to, amphetamine, dextroamphetamine, dinoprostone, methylphenidate, methylphenidate, modafinil, and pemoline. A suitable tranquilizer includes, but is not limited to, mesoridazine.

In another embodiment, the active agent includes a nerve impulse inhibitor. Suitable nerve impulse inhibitors include, but are not limited to levobupivacaine, lidocaine, prilocalne, mepivacaine, propofol, rapacuronium bromide, ropivacaine, tubocurarine, atracurium, doxacurium, mivacurium, pancuronium, vecuronium, pipecuronium, rocuronium, and mixtures thereof.

In another embodiment, the active agent includes an anti-opioid agent. Suitable anti-opioid agents for use in the buccal sprays of the invention include, but are not limited to, naloxone, nalmefene, naltrexone, cholecystokinin, nociceptin, neuropeptide FF, oxytocin, vasopressin, and mixtures thereof.

In another embodiment, the active agent includes an anti-migraine agent. Suitable anti-migraine agents for use in the buccal sprays of the invention include, but are not limited to, frovatriptan, zolmitriptan, rizatriptan, almotriptan, eletriptan, naratriptan, almotriptan, ergotamine, diethylergotamine, sumatriptan, and mixtures thereof.

In another embodiment, the active agent includes a pain control agent. Suitable pain control agents for use in the buccal sprays of the invention include, but are not limited to, non-steroidal anti-inflammatory drugs, alfentanil, butorphanol, codeine, dezocine, fentanyl, hydrocodone, hydromorphone, levorphanol, meperidine, methadone, morphine, nalbuphine, oxycodone, oxymorphone, propoxyphene, pentazocine, sufentanil, tramadol, and mixtures thereof.

In another embodiment, the active agent includes an anesthetic. Suitable anesthetics for use in the buccal sprays of the invention include, but are not limited to, benzo-natate, bupivacaine, desflurane, enflurane, isoflurane, levobupivacaine, lidocaine, mepivacaine, prilocalne, propofol, rapacuronium bromide, ropivacaine, sevoflurane, ketamine, and mixtures thereof.

In another embodiment, the active agent can include, but is not limited to, cyclo-sporine, sermorelin, octreotide acetate, calcitonin-salmon, insulin lispro, sumatriptan succinate, clozepine, cyclobenzaprine, dexfenfluramine hydrochloride, glyburide, zidovudine, erythromycin, ciprofloxacin, ondansetron hydrochloride, dimenhydrinate, cimetidine hydrochloride, famotidine, phenyloin sodium, phenyloin, carboprost thro-methamine, carboprost, diphenhydramine hydrochloride, isoproterenol hydrochloride, terbutaline sulfate, terbutaline, theophylline, albuterol sulfate, neutraceuticals (i.e., nutrients with pharmacological action, e.g., carnitine, valerian, echinacea, and the like), or the like; analogs/derivatives thereof; salts/alternate salts thereof; or combinations thereof.

Any opioid or non-μ-opioid, a pharmaceutically acceptable salt thereof, a base form thereof, or mixture of any combination of such opioids and/or their derivatives that are known in the art can be included. Opioids believed to have at least some μ-opioid receptor agonist activity (and optionally at least some agonist activity also at one or more of the K-opioid receptor, the δ-opioid receptor, and the ORL-1 receptor) include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydro-codeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorpho-done, hydroxypethidine, isomethadone, ketobemidone, levorphanol, levophenacyl-morphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymor-phone, pantopon, papavereturn, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, and mixtures thereof. Non-μ-opioids include, but are not limited to, ORL-1-specific opioid agonists, such as nociceptin, deltorphin, and the like, and mixtures thereof. In a preferred embodiment, the opioid includes buprenor-phine, pharmaceutically acceptable salts thereof, base forms thereof, fentanyl, pharmaceutically acceptable salts thereof, base forms thereof, oxycodone, pharmaceutically acceptable salts thereof, base forms thereof, and any combination of such opioids and/or their derivatives.

In certain embodiments, the opioid agonist includes hydrocodone, morphine, hydromorphone, oxycodone, codeine, levorphanol, meperidine, methadone, oxymor-phone, buprenorphine, fentanyl, dipipanone, heroin, tramadol, etorphine, dihydro-etorphine, butorphanol, levorphanol, pharmaceutically acceptable salts thereof, base forms thereof, and any and all mixtures thereof. The opioid agonist can, in some embodiments, include oxycodone, hydrocodone, fentanyl, buprenorphine, pharmaceutically acceptable salts thereof, base forms thereof, and any and all mixtures thereof. The opioid agonist can, in other embodiments, include buprenorphine, pharmaceutically acceptable salts thereof, base forms thereof, fentanyl, pharmaceutically acceptable salts thereof, base forms thereof, and any combination of such opioids and/or their derivatives.

General categories of active agents can, in one embodiment, include, but are not limited to: ACE inhibitors; adenohypophyseal hormones; adrenergic neuron blocking agents; adrenocortical steroids; inhibitors of the biosynthesis of adrenocortical steroids; alpha-adrenergic agonists; alpha-adrenergic antagonists; selective alpha-two-adrenergic agonists; androgens; anti-addictive agents; antiandrogens; anti-infectives, such as antibiotics, antimicrobials, and antiviral agents; analgesics and analgesic combinations; anorexics; antihelmintics; antiarthritics; antiasthmatic agents; anticonvulsants; antidepressants; antidiabetic agents; antidiarrheals; antiemetic and prokinetic agents; antiepileptic agents; antiestrogens; antifungal agents; antihistamines; antiinflammatory agents; antimigraine preparations; anti-muscarinic agents; antinauseants; antineoplastics; antiparasitic agents; anti-parkinsonism drugs; antiplatelet agents; antiprogestins; antipruritics; antipsychotics; antipyretics; antispasmodics; anticholinergics; antithyroid agents; antitussives; azaspirodecanediones; sympathomimetics; xanthine derivatives; cardiovascular preparations, including potassium and calcium channel blockers, alpha blockers, beta blockers, and antiarrhythmics; antihypertensives; diuretics and antidiuretics; vasodilators, including general coronary, peripheral, and cerebral; central nervous system stimulants; vasoconstrictors; cough and cold preparations, including decongestants; hormones, such as estradiol and other steroids, including cortico-steroids; hypnotics; immunosuppressives; muscle relaxants; parasympatholytics; psychostimulants; sedatives; tranquilizers; nicotine and acid addition salts thereof; benzodiazepines; barbituates; benzothiadiazides; beta-adrenergic agonists; beta-adrenergic antagonists; selective beta-one-adrenergic antagonists; selective beta-two-adrenergic antagonists; bile salts; agents affecting volume and composition of body fluids; butyrophenones; agents affecting calcification; catecholamines; cholin-ergic agonists; cholinesterase reactivators; dermatological agents; diphenylbutyl-piperidines; ergot alkaloids; ganglionic blocking agents; hydantoins; agents for control of gastric acidity and treatment of peptic ulcers; hematopoietic agents; histamines; 5-hydroxytryptamine antagonists; drugs for the treatment of hyperlipiproteinemia; laxatives; methylxanthines; moncamine oxidase inhibitors; neuron-muscular blocking agents; organic nitrates; pancreatic enzymes; phenothiazines; prostaglandins; retinoids; agents for spasticity and acute muscle spasms; succin-imides; thioxanthines; thrombolytic agents; thyroid agents; inhibitors of tubular transport of organic compounds; drugs affecting uterine motility; vitamins; and the like; or a combination thereof.

Alternately or in addition to an opioid agonist, another active compound may be added including, but not limited to, fluorogestone acetate, hydroxyprogesterone, hydroxyprogesterone acetate, hydroxyprogesterone caproate, medroxyprogester-one acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betametha-sone acetate, cortisone, hydrocortisone, hydrocortisone acetate, corticosterone, fluocinolone acetonide, prednisolone, prednisone, triamcinolone, aldosterone, androsterone, testosterone, methyl testosterone, or a combination thereof.

Alternately or in addition to an opioid agonist, another active compound may be added including, but not limited to: a) corticosteroids, e.g., cortisone, hydrocortisone, prednisolone, beclomethasone propionate, dexamethasone, betamethasone, flumethasone, triamcinolone, triamcinolone acetonide, fluocinolone, fluocinolone acetonide, fluocinolone acetate, clobetasol propionate, or the like, or a combination thereof; b) analgesic anti-inflammatory agents, e.g., acetaminophen, mefenamic acid, flufenamic acid, indomethacin, diclofenac, diclofenac sodium, alclofenac, ibufenac, oxyphenbutazone, phenylbutazone, ibuprofen, flurbiprofen, ketoprofen, salicylic acid, methylsalicylate, acetylsalicylic acid, 1-menthol, camphor, slindac, tolmetin sodium, naproxen, fenbufen, or the like, or a combination thereof; c) hypnotic sedatives, e.g., phenobarbital, amobarbital, cyclobarbital, lorazepam, haloperidol, or the like, or a combination thereof; d) tranquilizers, e.g., fulphenazine, thioridazine, diazepam, flurazepam, chlorpromazine, or the like, or a combination thereof; e) antihypertensives, e.g., clonidine, clonidine hydrochloride, bopinidol, timolol, pindolol, propranolol, propranolol hydrochloride, bupranolol, indenolol, bucumolol, nifedipine, bunitrolol, or the like, or a combination thereof; f) hypotensive diuretics, e.g., bendroflumethiazide, polythiazide, methylchlorthiazide, trichlor-methiazide, cyclopenthiazide, benzyl hydrochlorothiazide, hydrochlorothiazide, bumetanide, or the like, or a combination thereof; g) antibiotics, e.g., penicillin, tetracycline, oxytetracycline, metacycline, doxycycline, minocycline, fradiomycin sulfate, erythromycin, chloramphenicol, or the like, or a combination thereof; h) anesthetics, e.g., lidocaine, benzocaine, ethylaminobenzoate, or the like, or a combination thereof; i) antimicrobial agents, e.g., benzalkonium chloride, nitrofurazone, nystatin, sulfacetamide, clotriamazole, or the like, or a combination thereof; j) anti-fungal agents, e.g., pentamycin, amphotericin B, pyrrol nitrin, clotrimazole, or the like, or a combination thereof; k) vitamins, e.g., vitamin A, ergocalciferol, cholecalcif-erol, octotriamine, riboflavin butyric acid ester, or the like, or a combination thereof; l) antiepileptics, e.g., nitrazepam, meprobamate, clonazepam, or the like, or a combination thereof; m) antihistamines, e.g., diphenhydramine hydrochloride, chlorphen-iramine, diphenylimidazole, or the like, or a combination thereof; n) antitussives, e.g., dextromethorphan, terbutaline, ephedrine, ephedrine hydrochloride, or the like, or a combination thereof; o) sex hormones, e.g., progesterone, estradiol, estriol, estrone, or the like, or a combination thereof; p) antidepressants, e.g., doxepin; q) vaso-dilators, e.g., nitroglycerin, isosorbide nitrate, nitroglycol, pentaerythritol tetranitrate, dipyridamole, or the like, or a combination thereof; r) other drugs, e.g., 5-fluorouracil, dihydroergotamine, desmopressin, digoxin, methoclopramide, domperidone, scopol-amine, scopolamine hydrochloride, or the like, or a combination thereof; or the like; or a combination thereof.

In another embodiment, the active agent can include, but is not limited to, anti-staphylococcal agents (e.g., YSPXTNF, YSPWTNF, YSPWTNF-NH$_2$, GENBANK/AF202641, GENBANK/AF205220, GENBANK/AAG03056, or the like, or combinations thereof). Other agents that modulate the production or secretion of bacterial or microbial toxins or virulence factors may also be used as active agents. For instance, thiolactones and bacterial toxin regulatory proteins such as RNAIII-inhibiting peptides (RIPs) are classes of active agents. See, e.g., Balaban, N., et al., "Regulation of *Staphylococcus aureus* pathogenesis via target of RNAIII-activating Protein (TRAP)," *J. Biol. Chem.*, 2001 Jan. 26; 276(4): 2658-67, which is incorporated by reference herein in its entirety.

When an active agent of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. In one embodiment, the salt includes ammonium, calcium, magnesium, potassium, or a sodium salt. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropyl-amine, lysine, methyl-glucosamine, morpholine, piperazine, piperidine, polyamine resins, procaine, purine, theobromine, triethylamine, trimethylamine, tripropylamine, etc.

When an active agent of the present invention is basic, salts may be prepared from pharmaceutically acceptable non-toxic acids. Such acids include acetic, benzene-sulfonic, benzoic, camphorsulfonic, citric, ethane-sulfonic, fumaric, gluconic, glutamic, hydrobromic, hydrochloric, isethionic, lactic, maleic, mandelic, methane-sulfonic, mucic, nitric, pamoic, pantothenic, phosphoric, succinic, sulfuric, tartaric, p-toluenesulfonic, etc. In one embodiment, the acid includes citric, hydrobromic, maleic, phosphoric, sulfuric, and/or tartaric acids.

Although some active agents can be attached directly to the coating/derivatized surface, most active agents according to the present invention can often be attached to the coatings/derivatized surfaces of the invention via α,ω-difunctional linkers or spacers, which will often be tailored to the particular active agent(s) used. It is noted that the α- and ω-functional groups of the linkers/spacers can be similar or different, and often are different particularly where release of the active agent(s) is (are) intended (e.g., in vivo). Such attachment (and release) of active agents can be effected by covalent bonding (cleaving), ionic bonding (dissociation), physical transitions of state such as crystallization (melting) or liquid crystalline-type ordering (disordering), hydrogen bonding (dissociation), van der Waals interactions (repulsions), or the like, or any combination thereof. The linkers/spacers can be of relatively small molecular weight (e.g., less than about 200 g/mol), relatively intermediate molecular weight (e.g., from about 200 to about 2000 g/mol), relatively large molecular weight (e.g., more than about 2000 g/mol), or some combination thereof. Particularly when the linkers/spacers are of relatively intermediate and/or relatively large molecular weight, they can include, but are not limited to, oligomers, polymers, and/or copolymers described above as bioactive moieties or biodegrade-able polymers; additionally or alternately, the linkers/spacers can include, but are not limited to, oligomers, polymers, and/or copolymers having one or more of the following types of repeat units: urethanes, ureas, ethers, ketones, esters, amines, carbonates, amides, saccharides, or the like, or combinations thereof.

In other embodiments, polyfunctional linkers/spacers can be used to attach active agents to the coatings/derivatized surfaces according to the invention. Such poly-functional linkers/spacers can include, but are not limited to, oligomers, polymers, and/or copolymers that are branched, hyperbranched, dendritic, star-shaped, brushes, combs, block, multiblock, gels, hydrogels, or the like, or any combination thereof.

Characteristics of Coatings and Derivatized Surfaces

The coatings and derivatized surfaces according to the invention are typically present on synthesized, native and/or passivated oxide surfaces. In some cases, these surfaces have relatively low surface —OH content. For example, as mentioned above, titanium, silicon, and titanium alloys (such as Ti—6Al—4V) typically exhibit a surface —OH content of ~0.15-0.25 nmol/cm$^2$ —OH groups. The surface —OH content of titanium, silicon, titanium alloys and other implantable materials may be significantly lower, for example, ~0.10 nmol/cm$^2$ —OH groups, or for example ~0.05 nmol/cm$^2$ —OH groups depending upon the manufacturing environment or manufacturing process. Such manufacturing processes are known to one of skill in the art and include heating, anoxic heating or acid etching. In some cases, substantially all surface —OH groups can be removed. However, in some embodiments, it may be useful to use synthesized, native and/or passivated oxides that exhibit surface —OH contents of ≤0.5 nmol/cm$^2$ —OH groups, for example of ≤0.4 nmol/cm$^2$ —OH groups, for example of ≤0.3 nmol/cm$^2$ —OH groups, before coating and/or derivatization.

The phosphorous based coatings and derivatized surfaces according to the invention may be "functionalized" or "unfunctionalized." As used herein, the term "functionalized" means that the portion of the molecules remote to the end covalently bonded to an oxide surface has a terminal group that contains a usually chemically reactive moiety (e.g., an —OH group, an ω-phosphate group, an ω-phosphonate group, a —COON group, an amino group, a mercapto group, or the like, an unsaturated hydrocarbon group such as —CH═CH$_2$ or the like). As used herein, the term "unfunctionalized" means that the portion of the molecules remote to the end covalently bonded to an oxide surface has a terminal group that contains a usually-non-reactive moiety (e.g., a halocarbon group such as —CF$_2$CF$_3$ or —CH$_2$CF$_3$ or the like; a saturated hydrocarbon group such as —CH$_2$CH$_3$ or the like; or the like). The term "remote to" includes the functional groups being at any position removed from the phosphate or phosphonate moieties, including functional groups at a position omega to said moieties.

With respect to a layer, the term "functionalized" refers to the external surface of that layer, or the portion of that layer not being covalently bonded to an oxide surface, that exhibits a surface-containing, chemically reactive group. With respect to a layer, the term "unfunctionalized" refers to the external surface of that layer, or the portion of that layer not covalently bonded to an oxide surface, that exhibits a surface-containing, usually-non-reactive group.

In some embodiments where the phosphorus-based coating is functionalized, the surface functional group density (e.g., the surface density of hydroxyl groups, phosphate groups, phosphonate groups, thiol groups, carboxylic acid groups, carboxylate groups, etc.) can be more than about 0.1 nmol/cm$^2$, alternatively more than about 0.25 nmol/cm$^2$, also more than 0.3 nmol/cm$^2$, also more than about 0.4 nmol/cm$^2$, for example more than about 0.5 nmol/cm$^2$, alternately more than about 0.8 nmol/cm$^2$ or for example more than about 1.0 nmol/cm$^2$. Additionally or alternately, also in embodiments where the phosphorus-based coating is functionalized, the surface functional group density can be at least great than or equal to, at least about 1.3 times, at least about 1.5 times, for example at least about 2 times, or for example at least about 3 times the surface hydroxyl group density of an oxide surface of an implantable substrate. In other embodiments where the surface hydroxyl group density of an oxide surface of an implantable substrate is reduced by manufacturing or processing, the surface functional group density can be at least about 5 times, for example at least about 10 times, for example at least about 25 times, or for example at least about 100 times the surface hydroxyl group density of an oxide surface of an implantable substrate.

In some embodiments where the phosphorus-based coating is unfunctionalized, the surface graft/packing density can be more than about 0.1 nmol/cm$^2$, alternatively more than about 0.25 nmol/cm$^2$, for example more than about 0.3 nmol/cm$^2$, or for example more than about 0.5 nmol/cm$^2$, alternatively more than about 0.8 nmol/cm$^2$, at least about 1 nmol/cm$^2$, for example at least about 1.2 nmol/cm$^2$, alternately at least about 1.5 nmol/cm$^2$. Also in embodiments where the phosphorus-based coating is unfunctionalized, the surface graft/packing density can be at least great than or equal, or for example about 1.3 times, or for example about 1.5 times, at least about 2 times, for example at least about 2.5 times, the surface hydroxyl group density of an oxide surface of an implantable substrate. In other embodiments where the surface hydroxyl group density of an oxide surface of an implantable substrate is reduced by manufacturing or processing, the surface functional group density can be at least about 5 times, for example at least about 10 times, or for example at least about 25 times, or for example at least about 100 times the surface hydroxyl group density of an oxide surface of an implantable substrate.

In some embodiments where the phosphorus-based coating is functionalized, the surface phosphorus-containing group density (e.g., the surface density of phosphate and/or phosphonate groups) can be more than about 0.1 nmol/cm$^2$, for example more than about 0.25 nmol/cm$^2$, more than 0.3 nmol/cm$^2$, also more than about 0.4 nmol/cm$^2$, for example more than about 0.5 nmol/cm$^2$, alternately more than about 0.8 nmol/cm$^2$, at least about 1 nmol/cm$^2$, or about 1.5 nmol/cm$^2$. Additionally or alternately, also in embodiments where the phosphorus-based coating is functionalized, the surface functional group density can be greater than or equal to, or at least about 1.3 times, at least about 1.5 times, for example at least about 2 times, alternately at least about 2.5 times, the surface hydroxyl group density of an oxide surface of the substrate.

The phosphorus-based coating and/or derivatized layer can have a thickness of less than about 10 nm, less than about 5 nm, for example not more than about 3 nm, alternately not more than about 2.5 nm or not more than about 1.5 nm or not more than about 1 nm. In other embodiments, the phosphorus-based coating and/or derivatized layer can have a thickness of less than about 100 nm, or for example, less than about 50 nm, alternatively less than about 25 nm or less than about 15 nm.

In some embodiments, when the phosphorus-based coating and/or derivatized layer is bound to an oxide surface of an implantable substrate, the coating-oxide surface bond exhibits a Mode I (shear) strength of at least about 20 MPa, at least about 40 MPa, for example at least about 50 MPa, alternately at least about 60 Mpa or for example at least about 70 MPa.

In some embodiments, when the phosphorus-based coating and/or derivatized layer is bound to an oxide surface of an implantable substrate, the coating-oxide surface bond exhibits a tensile strength of at least about 60 MPa, or at least about 80 Mpa.

In one embodiment, the phosphorus-based coating is covalently bonded to an oxide surface of an implantable substrate and the phosphorus-based coating exhibits a surface phosphorus-containing group density of at least about 0.1 nmol/cm$^2$ and a thickness of less than about 10 nm.

As used herein, the term "implantable substrate" means any material with an oxide surface that may be totally or partially implanted into a human or animal body including, but not limited to titanium and its alloys, cobalt chromium and its alloys, stainless steel, alloys of stainless steel and nitinol. As used herein, the term "an oxide surface of an implantable substrate" means the entire oxide surface of an implantable substrate or one or more oxide surfaces of an implantable substrate. As used herein, the term "an oxide surface of an implantable device" means the entire oxide surface of an implantable device, or one or more oxide surfaces of an implantable device or one or more oxide surfaces of one or more implantable devices.

In another embodiment, the phosphorus-based coating and/or derivatized layer is covalently bonded to an oxide surface of an implantable substrate exhibiting a surface hydroxyl group density of not more than about 0.4 nmol/cm$^2$, and the phosphorus-based coating exhibits a surface phosphorus-containing group density of at least about 0.5 nmol/cm$^2$, a surface phosphorus-containing group density of at least about 1.3 times the surface hydroxyl group density of an oxide surface of an implantable substrate, and a thickness of less than about 5 nm.

In one embodiment, the phosphorus-based coating and/or derivatized layer is covalently bonded to an oxide surface of an implantable substrate exhibiting a surface hydroxyl group density of not more than about 0.3 nmol/cm$^2$, and the phosphorus-based coating exhibits a surface phosphorus-containing group density of at least about 1 nmol/cm$^2$, a surface phosphorus-containing group density of at least about 2 times the surface hydroxyl group density of an oxide surface of an implantable substrate, and a thickness of not more than about 2 nm.

In some embodiments where the phosphorus-based coating is functionalized, particularly when the functionality is a hydroxyl functionality (e.g., when 11-hydroxy-undecylphosphonic acid is covalently bonded to a metal/metal oxide substrate such as titanium), the coating and/or derivatized layer may exhibit cell non-attraction or cell resistance. As used herein, the terms "cell resistance" and "cell resistant," with respect to surfaces, should be understood to indicate the substantial absence of human fetal osteoblasts adherent to the surface and/or of actin filaments in human fetal osteoblasts that are adherent to the surface, when human fetal osteoblasts are exposed to surface for not more than 3 days, for example not more than 2 days, for example at least 90 minutes, also more than at least 12 hours, for example at least 24 hours.

In some embodiments where the phosphorus-based coating is functionalized, particularly when the functionality is a hydroxyl functionality (e.g., when 11-hydroxy-undecylphosphonic acid is bonded to a metal/metal oxide substrate such as titanium), the phosphorus-based coating and/or functionalized coating may be oxidatively stable. As used herein, the terms "oxidatively stable" and "oxidative stability," with respect to surfaces, should be understood to indicate that the surfaces exhibit any one or more of the following: (1) a surface content/functionality/loading after exposure for about 3 hours to 14/14/80 milliMolar TiCl$_3$/EDTA/H$_2$O$_2$ oxidant of at least 80%, for example at least 90%, for example at least 95% of the surface content/functionality/loading before exposure; (2) a normalized FTIR peak area from about 3000 cm$^{-1}$ to about 2750 cm$^{-1}$ and having a peak at about 2920-2910 cm$^{-1}$ after exposure for about 3 hours to 14/14/80 milliMolar TiCl$_3$/EDTA/H$_2$O$_2$ oxidant that differs by not more than about 20%, also not more than about 15%, for example not more than about 10% or not more than about 5%, as compared to the normalized FTIR peak area in the same region before exposure; (3) a normalized FTIR peak area from about 1110 cm$^{-1}$ to about 1050 cm$^{-1}$ and having a peak at about 1090 cm$^{-1}$ after exposure for about 3 hours to 14/14/80 milliMolar TiCl$_3$/EDTA/H$_2$O$_2$ oxidant that differs by not more than about 15%, not more than about 10%, for example not more than about 5% or not more than about 2%, as compared to the normalized FTIR peak area in the same region before exposure; (4) an average (of at least five values)

advancing and/or receding contact angle after exposure for about 3 hours to 14/14/80 milliMolar $TiCl_3/EDTA/H_2O_2$ oxidant that differs by not more than about 15%, not more than about 10°, for example not more than about 5°, as compared to the average advancing and/or receding contact angle before exposure (the advancing or receding contact angle may be measured with deionized water; however, other liquids may be used, e.g., 11-hydroxyundecylphosphonic acid, 1,6-diphosphonato-hexane, 1,12-diphosphonatododecane, octadecylphosphonic acid, or hexafluoro-isopropanol)

Cyclic RGD peptides can interact with integrins more effectively than their linear analogues possibly due to an increase in conformational stability which leads to an enhancement in the preferred three-dimensional structure for receptor interactions. For instance, cyclic (RGDFV-) exhibits over 100 times greater specificity towards $\alpha_v\beta_3$ integrins than linear GRGDSPK.

Additionally, it has been established that RGD peptide containing sequences are susceptible to chemical degradation at the aspartic acid residue which leads to loss of biological activity. It is believed that the rate of degradation is dependent upon the flexibility of the peptide sequence, which has generated interest in more rigid conformations, such as cyclic species. It has been shown in solution by HPLC that (cyclo)-1,6 acetyl-CRGDF-penicillamine-$NH_2$ was 30 times more stable than linear RGDF at pH 7.

Therefore, it would be of interest to use cyclic RGD containing species to both enhance integrin binding as well as to increase enzymatic stability in vivo.

While the cyclic conformation of RGD does increase the specific binding to $\alpha_v\beta_3$ integrins, there remains an affinity for other integrins which limits overall selectivity. It may be of interest to circumvent the selectivity issue by speeding the colonization of the implant surface which fosters the proper environment for osteoprogenitor cells. This could be achieved by creating mixed films of cyclic RGD (integrins) and saccharides that would create an environment that mimics the ECM of the cells. A polysaccharide-modified surface has been shown to attract roughly 200-fold more osteoblasts than untreated glass at an immersion time of 15 minutes. It could be of great benefit to couple the integrin-binding peptide sequence cyclic-RGD with the polysaccharide films in order to achieve fast colonization of the implant surface which could facilitate and speed healing.

In order to create these mixed-film systems, phosphonic acids films could be made on the oxide of interest through standard procedures. Then standard coupling techniques could be employed to bind mixed films of cyclic RGD and heparin saccharide derivatives. For example, examples of and methods for peptide coupling to implant surfaces can be found, e.g., in U.S. Pat. No. 6,280,760, the contents of which are hereby incorporated by reference.

Surprisingly, it has been found that linear RGD peptide containing sequences have higher than expected specificity, binding strength and enzymatic stability when attached to the coatings of the present invention.

In some embodiments where the phosphorus-based coating is functionalized (e.g., when hydroxyundecylphosphonic acid is bonded to an oxide surface of silicon), the coating and/or derivatized layer can demonstrate excellent current blockage properties.

Implantable Devices

The coatings and derivatized surfaces according to the invention can further be applied to a variety of implantable devices. Although any device with at least one oxide surface may comprise a coating of the invention, general classes of suitable implantable devices include, but are not limited to, vascular devices such as grafts, stents, stent grafts, catheters, valves, artificial hearts, and heart assist devices such as pacemakers; orthopedic devices such as joint implants, fracture repair devices, and artificial tendons; dental devices such as dental implants and fracture repair devices; drug delivery devices including drug infusion devices; ophthalmic devices and glaucoma drain shunts; urological devices such as penile, sphincter, urethral, bladder, and renal devices; and other catheters, synthetic prostheses such as breast prostheses and artificial organs; neurostimulation, electrostimulation and electrosensing devices including electrical stimulation leads, brain tissue stimulators, central nerve stimulators, peripheral nerve stimulators, spinal cord nerve stimulators and sacral nerve stimulators. Other suitable biomedical devices include dialysis tubing and membranes, blood oxygenator tubing and membranes, blood bags, sutures, membranes, cell culture devices, chromatographic support materials, biosensors, anastomotic connector, surgical instrument, angioplasty balloon, wound drain, shunt, tubing, urethral insert, pellet, blood oxygenator, pump, and the like.

Exemplary implantable devices that may comprise one or more coated surfaces of the invention are listed in Table 2 below (all references as set forth below are herein incorporated by reference in their entirety for all purposes). For instance, any device classified within any of the following statutory classifications may comprise one or more coated surfaces of the invention and is herein incorporated by reference for all purposes.

TABLE 2

Exemplary Implantable Orthopedic and Dental Devices

| Device(s) | Subtype | Examples References |
|---|---|---|
| Implantable, artificial hip joint prosthesis | All types | See, e.g. 21 CFR § 888.3300 (2005) |
| Implantable, artificial hip joint prosthesis | Constrained or semi-constrained | See 21 CFR § 888.3300, 3330, 3353, 3358 (2005) |
| Implantable, artificial hip joint prosthesis | Uncemented femoral stem and/or uncemented acetabular cup | 21 CFR § 888.3300 (2005) Hip joint metal/metal semi-constrained, with an uncemented acetabular component, prosthesis 21 CFR § 888.3353 (2005) Hip joint metal/ceramic/polymer semi-constrained cemented or nonporous uncemented prosthesis. 21 CFR § 888.3358 (2005) Hip joint metal/polymer/metal semi- |

TABLE 2-continued

Exemplary Implantable Orthopedic and Dental Devices

| Device(s) | Subtype | Examples References |
|---|---|---|
| Implantable, artificial hip joint prosthesis | Metal ball on femoral stem to metal acetabular cup | constrained porous-coated uncemented prosthesis<br>21 CFR § 888.3300 (2005) Hip joint metal/metal semi-constrained, with an uncemented acetabular component, prosthesis<br>21 CFR § 888.3358 (2005) "Hip joint metal/polymer/metal semi-constrained porous-coated uncemented prosthesis." |
| Implantable, artificial hip joint prosthesis | Metal ball on femoral stem to polymer lined acetabular cup | 21 CFR § 888.3390 (2005) "Hip joint femoral (hemi-hip) metal/polymer cemented or uncemented prosthesis."<br>21 CFR § 888.3358 (2005) "Hip joint metal/polymer/metal semi-constrained porous-coated uncemented prosthesis." |
| Implantable, artificial hip joint prosthesis | Metal ball on femoral stem to ceramic lined acetabular cup | See, e.g. 21 CFR § 888.3353 (2005) Hip joint metal/ceramic/polymer semi-constrained cemented or nonporous uncemented prosthesis. |
| Implantable, artificial hip joint prosthesis | Ceramic ball on femoral stem to ceramic or polymer lined acetabular cup | See, e.g. 21 CFR § 888.3353 (2005) Hip joint metal/ceramic/polymer semi-constrained cemented or nonporous uncemented prosthesis. |
| Implantable, artificial hip joint prosthesis | Hemi-hip | 21 CFR § 888.3360 (2005) Hip joint femoral (hemi-hip) metallic cemented or uncemented prosthesis.<br>21 CFR § 888.3390 (2005) Hip joint femoral (hemi-hip) metal/polymer cemented or uncemented prosthesis. |
| Implantable hip resurfacing prosthesis | | 21 CFR § 888.3400 (2005) Hip joint femoral (hemi-hip) metallic resurfacing prosthesis |
| An acetabular component of an implantable, artificial hip joint | Acetabular cup, acetabular ring or acetabular cage | |
| An acetabular component of an implantable, artificial hip joint | Uncemented. Interior surface comprising metal, polymer, ceramic. | See e.g., 21 CFR § 888.3300 (2005) Hip joint metal/metal semi-constrained, with an uncemented acetabular component, prosthesis |
| Implantable, artificial knee joint prosthesis | All types | |
| Implantable, artificial knee joint prosthesis | Uncemented, metal/polymer or metal/metal. | 21 CFR § 888.3535 (2005) Knee joint femorotibial (uni-compartmental) metal/polymer porous-coated uncemented prosthesis<br>21 CFR § 888.3550 (2005) Knee joint patellofemorotibial polymer/metal/metal constrained cemented prosthesis<br>21 CFR § 888.3565 (2005) Knee joint patellofemorotibial metal/polymer porous-coated uncemented prosthesis |
| Implantable, artificial knee joint prosthesis | Uncemented femoral component | 21 CFR § 888.3570 (2005) Knee joint femoral (hemi-knee) metallic uncemented prosthesis |
| Implantable, artificial knee joint prosthesis | Uncemented patellar component | 21 CFR § 888.3580 (2005) Knee joint patellar (hemi-knee) metallic resurfacing uncemented prosthesis |
| Implantable, artificial knee joint prosthesis | Uncemented tibial component | 21 CFR § 888.3590 (2005) Knee joint tibial (hemi-knee) metallic resurfacing uncemented prosthesis |

TABLE 2-continued

Exemplary Implantable Orthopedic and Dental Devices

| Device(s) | Subtype | Examples References |
|---|---|---|
| Implantable, artificial shoulder joint prosthesis | All types | 21 CFR § 888.3670 (2005) Shoulder joint metal/polymer/metal nonconstrained or semi-constrained |
| Implantable, artificial shoulder joint prosthesis | Uncemented | 21 CFR § 888.3670 (2005) Shoulder joint metal/polymer/metal nonconstrained or semi-constrained |
| Implantable, artificial shoulder joint prosthesis | Glenoid component (hemi-shoulder) | |
| Implantable, artificial shoulder joint prosthesis | Humeral component (hemi-shoulder) | 21 CFR § 888.3690 (2005) Shoulder joint humeral (hemi-shoulder) metallic uncemented prosthesis |
| Implantable artificial spine prostheses | Pedicle screw system | 21 CFR § 888.3070 (2005) Pedicle screw system |
| Implantable artificial spine prostheses | Spinal interlaminal fixation orthosis | 21 CFR § 888.3050 (2005) Spinal interlaminal fixation orthosis |
| Implantable artificial spine prostheses | Spinal intervertebral body fixation orthosis | 21 CFR § 888.3060 (2005) Spinal intervertebral body fixation orthosis |
| Implantable artificial elbow joint prosthesis | All types | 21 CFR § 888.3150 (2005) Elbow joint metal/polymer constrained cemented prosthesis 21 CFR § 888.3160 (2005) Elbow joint metal/polymer semi-constrained cemented prosthesis |
| Implantable artificial elbow joint prosthesis | Humeral Stem, uncemented | 21 CFR § 888.3180 (2005) Elbow joint humeral (hemi-elbow) metallic uncemented prosthesis |
| Implantable artificial elbow joint prosthesis | Ulnar Stem, uncemented | |
| Implantable artificial wrist joint prosthesis | All types | |
| Implantable artificial wrist joint prosthesis | Uncemented | 21 CFR § 888.3790 (2005) Wrist joint metal constrained cemented prosthesis |
| Implantable artificial ankle joint prosthesis | All types | |
| Implantable artificial ankle joint prosthesis | Uncemented, metal/metal or metal/composite or metal/polymer | No FDA definition for uncemented ankle joints. See 21 CFR § 888.3100-3120 (2005). |
| Implantable artificial ankle joint prosthesis | Semi-constrained, metal/composite or metal/polymer | 21 CFR § 888.3100 (2005) Ankle joint metal/composite semi-constrained cemented prosthesis 21 CFR § 888.3110 (2005) Ankle joint metal/polymer semi-constrained cemented prosthesis |
| Implantable artificial ankle joint prosthesis | Uncemented, semi-constrained or non-constrained | No FDA definition for uncemented ankle joints. See 21 CFR § 888.3100-3120 (2005). |
| Implantable artificial ankle joint prosthesis | Non-constrained | 21 CFR § 888.3120 (2005). Ankle joint metal/polymer non-constrained cemented prosthesis. |
| Implantable artificial finger joint prosthesis | All types | |
| Implantable artificial finger joint prosthesis | Uncemented, constrained or unconstrained | 21 CFR § 888.3300 (2005) Finger joint metal/metal constrained uncemented prosthesis. |
| Implantable artificial toe prosthesis | All types | |
| Implantable artificial toe prosthesis | Uncemented | 21 CFR § 888.3720 (2005) Toe joint polymer constrained prosthesis 21 CFR § 888.3730 (2005) Toe joint phalangeal (hemi-toe) polymer prosthesis |
| Orthopedic devices for fracture repair, bone fusion, fixation | Rods and pins | 21 CFR § 888.3720 (2005) Intramedullary fixation rod |
| Orthopedic devices for fracture repair, | Pins, nails, screws, staples, hooks, cable grip | 21 CFR § 888.3730 (2005) Single/Multiple component metallic |

TABLE 2-continued

Exemplary Implantable Orthopedic and Dental Devices

| Device(s) | Subtype | Examples References |
|---|---|---|
| bone fusion, fixation | | bone fixation appliances and accessories |
| Orthopedic devices for fracture repair, bone fusion, fixation | Smooth or threaded metallic bone fixation fastener | 21 CFR § 888.3740 (2005) Smooth or threaded metallic bone fixation fastener |
| Orthopedic devices for fracture repair, bone fusion, fixation and trauma treatment | Bone plate | |
| Orthopedic devices for fracture repair, bone fusion, fixation and trauma treatment | Metal external fixator pin; metal external fixator screw | |
| Orthopedic devices for fracture repair, bone fusion, fixation and trauma treatment | Bone screw, canulated or uncanulated | |
| Orthopedic devices for fracture repair, bone fusion, fixation and trauma treatment Orthopedic devices for limb lengthening | Bone nails, straight or curved | |
| Dental implant | Endosseous dental implant | 21 CFR § 888.3640 (2005) Endosseous dental implant |
| Dental implant | Endosseous dental implant abutment | 21 CFR § 888.3630 (2005) Endosseous dental implant abutment |
| Dental implant | Subperiosteal implant material | 21 CFR § 888.3645 (2005) Subperiosteal implant material |

EXAMPLES

Examples 1-3

For the following Examples 1-3, ethanol (reagent grade) was obtained from Aldrich Chemical and used as received. 11-Hydroxyundecylphosphonic acid (a linear, 11-carbon-atom difunctional phosphonic acid having an ω-hydroxyl functional group to the phosphonic acid) was synthesized according to published procedures. Disks were cut from titanium Ti—6Al—4V rod (1" in diameter, obtained from Goodfellow, Inc.) and prepared for use by sanding, followed by cleaning with methanol. The disks were dried for at least an hour before use, and stored in an oven at 200° C.

Samples were analyzed using either a Nicolet 730 FT-IR equipped with a Spectra Tech diffuse reflectance (DRIFT) attachment or a MIDAC Illuminator equipped with a Surface Optics specular reflectance head. When the Nicolet was used for analysis, infrared experiments were performed using a glancing angle attachment, a Variable Angle Specular Reflectance Model 500, obtained from Spectra Tech. The angle between the surface normal and the incident beam was approximately 87°. For both instruments, samples were purged with nitrogen for half an hour to reduce the amount of water on the surface, and 1,000 scans were collected to obtain a reasonable signal to noise ratio. All spectra obtained were as a ratio against a spectrum of a clean native oxide surface.

Example 1

Application of a Coating Layer

A white cotton swatch of commercial textile measuring 2" square was prepared as a carrier by rinsing in distilled water and drying in air. A 1.0 millimolar coating solution of 11-Hydroxyundecylphosphonic acid was prepared by dissolving 0.1 mM of the acid in 100 ml of ethanol. About 50 ml of the solution was placed in a shallow dish and the carrier was placed into the solution and saturated with it. The carrier was then removed from the solution and permitted to remain in air until it was visibly dry (overnight). Thus prepared, the carrier with containing a coating composition comprising 11-Hydroxyundecylphosphonic acid was placed over a titanium disk prepared as described above. A consumer cloth iron with a Teflon™-coated heating platen (Black & Decker) set for cotton cloth (no steam) was placed on top of the assembly for a period of 5 minutes. At the end of the heating period the iron was removed and the oxide substrate (titanium disk) was allowed to cool in the ambient air. The disks were sonicated in ethanol and rinsed with copious amounts of ethanol and dried in air.

Infrared examination of the area covered by the carrier by the procedure described above showed the presence of a coating layer comprising bound 11-hydroxyundecylphosphonate. Integration of the signal strength indicated that the films comprised about 10 times the amount of material typically observed by treating similar surfaces directly with a similar coating solution. Repeated rinising and sonication did not result in a diminution of the signal, indicating that the coating layer was well bound to the surface.

Visual inspection of the coupon shows that a coating layer is applied to the coupon only where contact was made with the carrier.

Example 2

Deposition of a Coating Layer on a Metal Oxide Coated Plastic

A sheet of antireflective coated polyethylene oxide terephthalate (PET) which has a top layer of silicon dioxide will be obtained from Bekaert Specialty Films. Application of a cotton carrier prepared with a coating composition, as described above for Example 1, in accordance with the treatment procedure described above for Example 1 will be found to provide an 11-hydroxyundecylphosphonate coating to the antireflective coated plastic.

Example 3

Derivatization of the Surface with an Adhesive Layer

It will be found that the coating layer prepared in Example 1 above (a phosphonate coating derived from 11-hydroxyundecylphosphonic acid) can be further derivatized with an epoxy linking group by applying a film of Cytec Fiberite FM 1000™ epoxy adhesive to the surface. Before the adhesive cured, a second titanium coupon prepared according to Example 1 can be placed in contact with the epoxy such that a lap joint is formed. When the epoxy is cured under ambient conditions, it will be found that the strength of the lap joint, when compared with substantially similar assemblies prepared from equivalent titanium coupons which have not received a coating layer by the process of the invention, is considerably lower. It will be found if these samples are compared according to ASTM testing standard F1044-99, that on average, the joint between the uncoated coupons failed at ⅔ the pressure which must be applied to fail the joint between the coated coupons.

Examples 4-33 and Comparative Examples 1-5

Example films of phosphonates and phosphates were prepared on coupons of metal foil or on disks of metal cut from billet. As noted, samples were prepared in some cases by dip coating the coupon in a bulk solution of the coating moiety and in others by aerosol application of the solution to a surface of the coupon. Aerosol application of monofunctional phosphonic acids was carried out by dissolving the acid in tetrahydrofuran (THF) or methanol, spraying the acid solution onto the target oxide surface. As noted, aerosol application was carried out either in the ambient environment by spraying a solution of the acid from a pump-spray bottle, or with the target surface residing in a standard nitrogen charged glove box.

The solvent was allowed to evaporate from the sample either with gentle heating and/or a gas current, for example, nitrogen flowing over the surface, or left to evaporate to the ambient environment by spraying in a solution of the acid from a pump-spray bottle. Where noted, solvent evaporation was carried out in the ambient environment or in an inert atmosphere glove box. For application of difunctional phosphonic acids, two procedures were followed. In the first procedure, a THF solution of the phosphonic acid was applied to the target oxide surface while its substrate rested in the ambient atmosphere on a hot plate to aid evaporation of the solvent. The treated oxide surface and substrate were then transferred to a 120° C. oven and annealed at oven temperature for up to 48 hours. Following removal from the oven and cooling, the derivatized surface was rinsed with dry, distilled THF to ensure only bound species remained. The residue of rinsing solvent remaining on the coupon was evaporated and the coupon surface was subjected to analysis.

In the second procedure, the substrate was placed in a vessel containing a quantity of acid solution, the solvent was evaporated with the substrate in place and the substrate was annealed in an oven to react the phosphoric acid solvent to the surface with the native oxide.

In the formation of phosphate coatings, spray or dip procedures, described above, were employed to pre-coat the native oxide surface with phosphoric acid solution. Where noted, phosphoric acid was used as either a THF or aqueous solution.

Films were analyzed using a quartz microbalance and by FTIR spectroscopy, X-ray powder diffraction spectroscopy, contact angle measurement and "peel testing". The following procedures were used.

Quartz Crystal Microbalance (QCM)

The QCM technique allows accurate, gravimetric determination of mass changes on an electrode which is deposited on a piezoelectric quartz crystal. It is, thus, ideal to monitor surface reactions of target metals when they are used as such electrodes: the QCM oscillates at a resonant frequency which is determined by the cut and mass of the crystal, and, just as for a classical oscillator, changes in electrode mass result in changes in crystal resonant frequency. Since our experiments necessitated detaching active crystals from the QCM oscillator for extended periods of time followed by reattachment, control measurements had to be made of reference crystals which were subjected to similar handling, but without surface treatment. Up to three different reference crystals (prepared in different batches) were used as received to calibrate the QCM. Careful handling of the active and reference crystals was observed to prevent unacceptably large (>10 Hz) frequency change from the initial value, during an experimental run. To ensure that monolayer coverage (at most) occurred on Ti surface, phosphonic acid-based films were subjected to copious rinsing followed by evacuation ($\leq 10^{-2}$ Torr) until a constant crystal frequency was established (within experimental noise levels of ±2 Hz).

Piezoelectric quarts crystals (International Crystal Manufacturers [ICM]; AT-cut, 1000 Å Ti electrodes, 10 MHz, overtone polished, 0.201 in. electrode diameter) were used for film deposition and as references. The QCM circuitry was allowed to stabilize for 30 min. after start-up, before experimental measurements were made. In each experimental run, the fundamental frequency ($f_o$) of an unreacted crystal was measured. The crystal was then removed from its holder, aerosol sprayed (on both electrodes) with a solution of the phosphorous-based acid and heated at 120° C. for 3 days. A new frequency ($f_c$) was then measured. The crystal was then subjected to rinsing followed by evacuation ($\leq 10^{-2}$ Torr) until a constant frequency was measured (±2 Hz), assumed to be a monolayer coverage of the Ti electrodes. The difference between the monolayer-loaded and the unreacted crystal was then related to the amount of material chemisorbed on the Ti electrode active area.

The quartz crystal microbalance (QCM) was driven by a home-built Clapp oscillator and powered by a Hewlett Packard 6234A Dual Output Power Supply. The frequency of the crystal was measured using a Hewlett Packard 5334B Universal Counter and a record of the frequencies was tracked using a laboratory computer. A change in the observed frequency indicated a change in the mass of the crystal. To ensure that all the frequency changes were attributable to the deposition of the reactants, the frequency of the crystal was monitored before and after exposure to reactants. See, e.g., U.S. Provisional Application No. 60/684,159.

X-ray Powder Diffraction

Samples were analyzed by X-ray diffraction using a Rigaku Miniflex spectrometer with CuK~ radiation and a Zn filter. Samples were scanned for $2\theta=8$-$55°$ ($0.04°/2$ sec). Data were analyzed and refined and matched with that of known species using Jade 3.0 Pattern Processing for Windows. Samples were placed on glass microscope slides using Dow Corning Vacuum Grease, and were placed in an appropriate holder.

Infrared Spectroscopy

Samples were analyzed using either a Nicolet 730 FT-IR equipped with a Spectra Tech diffuse reflectance (DRIFT) attachment or a MIDAC Illuminator equipped with a Surface Optics specular reflectance head. When the Nicolet was used for analysis, infrared experiments were performed using a glancing angle attachment, a Variable Angle Specular Reflectance Model 500, obtained from Spectra Tech. The angle between the surface normal and the incident beam was approximately $87°$. For both instruments, samples were purged with nitrogen for half an hour to reduce the amount of water on the surface, and 1,000 scans were collected to obtain a reasonable signal to noise ratio. All spectra obtained were ratioed against a spectrum of a clean native oxide surface.

"Peel-Testing"

Coupons which had been treated were rinsed several times with deposition solvent and, where appropriate, ethanol and/or water, to remove soluble residues. A piece of tape (e.g., 3M red Scotch™ "650" tape or Scotch Masking Tape #234; 37 oz./in. adhesion to steel) was adhered to the derivatized surface of the solvent washed foil sample and quickly removed. The freshly "peeled" coupon was then analyzed again by DRIFT spectroscopy.

Contact Angle Measurement

Contact angles were measured at room temperature and ambient conditions on a Tantec Contact Angle Meter CAM-F1.

All reagents were obtained from Aldrich Chemical unless otherwise noted. Propionic acid (99+ percent), octanoic acid (99.5+ percent), and stearic acid (99.5+ percent) were used as received, 11-phosphonoundecanoic acid (an 11 carbon atom, linear difunctional phosphonic acid with an ω-carboxylic acid functional group to the phosphonic acid) 11-hydroxy-undecylphosphonic acid (a linear, 11 carbon atom difunctional phosphonic acid having an ω-hydroxyl functional group to the phosphornic acid) were synthesized by a published procedure. Tetrakis(tert-butoxy)-zirconium (TBZ) was distilled at $10^{-1}$ torr and $80°$ C. The distilled product was stored in a nitrogen dry box, in the dark, and at $-40°$ C. until needed. Otherwise, solvents were used as purchased. Titanium (0.25 mm; 99.6%), aluminum (0.25 mm; 99.0%); and iron (0.125 mm; 99.5%) foils and titanium Ti—6Al—4V billet (all obtained from Goodfellow, Inc.) were prepared for use by sanding, followed by cleaning with methanol, and cut into ~1 cm*1 cm coupons (foils) or 1 inch diameter disks (billet). The coupons were dried for at least an hour before use, and stored in an oven at $200°$ C.

The first set of comparative examples demonstrate the films which can be formed on various native metal oxide surfaces using ambient temperature contact of the surface with a carboxylic and a phosphonic acid, both of which represent classes of art-recognized oxide surface derivatizing agents.

Comparative Example 1

Carboxylic Acid Treatment of Aluminum Native Oxide

A coupon of aluminum was prepared as described above. A 1.0 mM solution of stearic acid in iso-octane was prepared for deposition on the aluminum coupon. Deposition was carried out by immersing the aluminum coupon into the stearic acid solution for 24 hours, then washed with fresh iso-octane. The presence of a stearic acid film was confirmed by IR spectroscopy. The self-assembled monolayer alignments were confirmed by contact angle measurements. Washing the substrates after they were immersed in the carboxylic acid solutions aided in the removal of molecules that were not bound to the aluminum, but were merely sitting on the surface.

The films formed in solution were stable. The stearic acid film, which formed in 24 hours, was removed by anhydrous ethyl ether under mild conditions in the same amount of time. The monolayer-coated aluminum substrate was placed in ether at room temperature without using any stirring device. Removal of a significant portion of the film within 90 minutes was confirmed by IR spectroscopy. After removing the monolayer, it was possible to establish another monolayer on the aluminum surface by repeating the same technique. This could be done repeatedly, but there was a gradual erosion of the aluminum substrate.

From the IR information, it was apparent that the interaction between the carboxylic acid and the metal oxide substrate surface was weak, as illustrated by the ability to produce and remove the monolayer under mild conditions. The nature of the interaction is apparently hydrogen bonding between the acid and the hydroxyls on the surface of the metal. Apparently, covalent bonds are not formed because, if they were, much more vigorous conditions would be required to remove the carboxylic acid from the surface of the metal oxide.

Comparative Examples 2-4

Ambient Phosphonic Acid Treatment of Aluminum, Iron, and Titanium Native Oxide Surfaces Samples of coupons of aluminum, iron, and titanium, prepared as described above, were treated with an aerosol of n-octadecanephosphonic acid in tetrahydrofuron (THF) at room temperature in the ambient environment. Following the spray application of the acid solution the solvent was allowed to evaporate at ambient temperature and the derivatized surfaces of the coupons were analyzed by FTIR. The surfaces where then washed with THF and analyzed both before and after a peel test using red Scotch™ "650" tape. The analysis shows that on iron, the phosphonic acid forms a layer on the native surface oxide that, while of sparse coverage, survives both washing and peel testing. In the case of the aluminum samples, a weakly bound phosphonic acid layer is formed that survives washing, but not peel testing. For the titanium sample, any phosphonic acid which absorbed to the surface was readily removed by washing with the deposition solvent.

Comparative Examples 5

Vacuum-Annealing of Phosphonic Acid Coating Applied to Titanium Native Oxide Surfaces A titanium coupon, prepared as described above was treated with a 0.8 mM THF solution of octadecanephosphonic acid in the form of an aerosol spray under dry $N_2$. The treated coupon was placed under vacuum ($10^{-1}$ torr), and sealed off. The coupon remained in the evacuated vessel for six hours. DRIFT analysis before and after rinsing of the sample demonstrated that none of the phosphonic acid remained on the surface after rinsing in THF.

The next group of examples demonstrates derivatization of titanium oxide surfaces according to the present invention using a phosphonic acid and phosphonic acid derivatives.

Example 4

Formation of Bound Phosphonic Acid Film on a Titanium Native Oxide Surface

A titanium coupon, prepared as described above was treated with a 0.6 mM THF solution of octadecanephosphonic acid in the form of an aerosol spray under dry $N_2$. The treated coupon was left under a current of dry nitrogen until the solvent evaporated. Following solvent evaporation the sample was heated for 18 hours at 110° C. in air. The coupon was cooled to ambient temperature and rinsed twice with THF. This cycle of application, heat annealing, and rinsing was repeated five times. DRIFT analysis of the resulting coating on the coupon demonstrated that a phosphonate surface coating was bonded to the surface and remained after rinsing and peel testing. The coupons thus prepared were stored in an oven at 200° C. there being no upper limit on annealing time.

Example 5

Formation of a Difunctional, Bound Phosphonic Acid Film on a Titanium Native Oxide Surface A 5 mM solution of 11-phosphonoundecanoic acid in dry, distilled THF was aerosol sprayed onto a titanium coupon prepared as described above using the procedure described above for preparation of films using difunctional phosphonic acids. Analysis by infrared spectroscopy (IR) of the resulting surface films produced show the characteristic IR stretches observed for alkyl chains and for bound phosphonic acids, indicating that the phosphonate group was bound to the surface of the coupon and the ω-carboxylic acid groups were oriented away from the surface and hydrogen bonded.

Example 6

Formation of a Difunctional, Bound Hydroxyphosphonic Acid Film on a Titanium Native Oxide Surface A 10 mM THF solution of 11-hydroxyundecylphosphonic acid was applied to a titanium coupon, prepared as described above, as an aerosol using the procedure described for Example 5, except that baking of the sample was limited to 18 hours post application. Infrared analysis indicated that the phosphonic acid portion of the coating precursor was bound to the native oxide and showed a broad peak between 3300 and 3600 $cm^{-1}$ indicative of hydrogen-bonded hydroxyl groups as well as characteristic peaks for the aliphatic chain.

Example 7

Formation of Bound, Mixed-Difunctional Phosphonic Acid Coating on a Titanium Native Oxide Surface Using the procedure described for Example 5, above, coatings comprising mixtures of 11-phosphonoundecanate acid and either 4-phosphonobutyrate, decanephosphonate or a mixture of these species in any ratio will be prepared by aerosol applications of a solution containing a mixture of these species. The ratio of surface bound materials will be found to be close to that of the ratio of acid constituents of the solution applied. Subsequent coupling chemistry (with, for example, a phenol or an amino acid) can be accomplished to optimize yields of elaborated surface films by controlling the microenvironments of the ω-carboxlic acid termini in this manner. Similar experiments can be done for mixtures containing ω-hydroxyalkylphosphonate as well.

In the second and third groups of examples, following, films formed on titanium metal coupons using difunctional phosphonic acids (both the ω-carboxylic acid and ω-hydroxyl functional films) are further reacted with moieties useful in demonstrating the reactivity of the layer and with other moieties which are useful in the promotion of bone adhesion.

Examples 8-9

Further Derivatization of Titanium Oxide Surface Bound Difunctional Phosphonic Acid In this second group of examples, the free carboxylic acid portion of the difunctional phosphonate layer applied to the surface of a titanium coupon prepared according to Example 5 is further reacted at the carboxylic acid site by esterification of the acid with a phenol, an amino-acid, and with a peptide.

Example 10

Formation of Amino Acid Amides of Bound Difunctional Phosphonic Acid Coating on a Titanium Native Oxide Surface Coupons were derivatized with a carbodiimide/hydroxysuccinimide coupling reagent. Coupons prepared according to Example 5 were stirred in an aqueous solution (75 mM) of 1-ethyl-3-(3-dimethyl-aminopropyl)-carbodiimide and 20 mM N-hydroxysuccinimide to form the imido-adduct of the acid. The coupons thus treated were then transferred to a beaker of a 75 mM solution of lysine in water. The coupons were then extensively rinsed with water and dried under vacuum. FTIR analysis indicates the presence of an amide (coupling of the carboxylic acid of the phosphonate and the amine functional group of the lysine amino acid).

Example 11

Formation of Peptide Thio-esters of Bound Difunctional Phosphonic Acid Coating on a Titanium Native Oxide Surface The use of a surface of the present invention to bind short peptides to a Ti or alloy surface is demonstrated next. A cysteine-modified peptide, RGDC (Arg-Gly-Asp-Cys), described above which occurs in fibronectin cell-adhesive protein, is selected for attachment to the carboxylic acid ends of surface layers on titanium coupons prepared according to Example 5, above. The coupons are first treated with a solution of dicyclohexylcarbodiimide and N-(6-hydroxyhexyl)-maleimide in dichloromethane to provide the ω-carboxylic acid groups of the derivatized surface of the coupon with a maleimide ester group that will react with thiol functionality in the cysteine of the modified peptide. Foils are then bathed in an aqueous solution of RGDC (Arg-Gly-Asp-Cys) to couple the thiol group of cysteine to the immobilized maleimide group, leading to the attachment of RGDC to the ω-carboxylic acid-maleimide, yielding a bioactivated Ti surface.

In this second group of examples, the free hydroxide portion of the difunctional phosphonate layer applied to the surface of a titanium coupon prepared according to Example 6 using 11-hydroxy-undecylphosphonic acid is further reacted at the hydroxy functional group by conventional organic chemistry with dansyl chloride, an amino acid, and with a peptide.

Example 12

Reaction of Titanium Oxide Surface Bound ω-Difunctional 11-Hydroxy-Undecylphosphonic Acid With Dansyl Chloride Titanium coupons prepared according to Example 6 above were placed in a solution of approximately 10 mg of dansyl chloride and 0.1 mL of triethylamine in 10 mL of acetonitrile. The solution was stirred for 18 hours under $N_2$. Coupons were removed from the solution, blotted dry and rinsed with acetonitrile. The coupons were then subjected to FTIR analysis which indicates, by the presence of new peaks at 1600 cm$^{-1}$ and at 1200-1100 cm$^{-1}$, that a sulfonate ester formed. The dansyl adduct has a characteristic fluorescence spectrum, and fluorescence microscopic analysis of the coupons confirms the formation of the surface-bound dansyl ester product. The fluorescence spectroscopy also indicates that the coating is dense-coverage and uniform over the entire surface of the coupon.

For the next two examples, the surface bound hydroxy-phosphonate is converted into the maleimide adduct according to the following procedure. A coupon prepared according to Example 3, above, is placed into a solution of about 15 mg of 3-maleimido-(propionic-acid-N-hydroxysuccinimide) ester in 10 mL of acetonitrile. The coupon is then transferred into a nitrogen glove box and placed into an ambient temperature maleimide solution for 24-72 hours, after which, coupons are removed from the solution and blotted dry, and rinsed with acetonitrile. FTIR analysis indicates peaks corresponding to 11-hydroxyundecylphosphonate bound to the surface of the coupon through the phosphonate functional group, with additional peaks at ~1731 and ~1707 cm$^{-1}$ corresponding to the carbonyl stretches of the maleimide adduct.

Example 13

Reaction of Titanium Oxide Surface Bound ω-Difunctional 11-Hydroxy-Undecylphosphonic Acid With Cysteine Coupons having the phosphonate-maleimide adduct, prepared as described above on titanium coupons prepared according to Example 6, were placed in a stirred solution of 15 mg of cysteine dissolved in 10 mL of doubly distilled, Millipore™-filtered water for 8-24 hrs. The foils were removed from solution, dried, and rinsed in doubly distilled water. FTIR analysis of the coupons showed changes in the maleimide carbonyl region and a new peak at ~1700 cm$^{-1}$, indicative of the presence of cysteine bound to the coupon.

Example 14

Reaction of Titanium Oxide Surface Bound ω-Difunctional 11-Hydroxy-Undecylphosphonic Acid With a Peptide Coupons containing the phosphoric coated-maleimide adduct, prepared as described above from titanium coupons prepared according to Example 6, are placed in a solution of the peptide RGDC (Arg-Gly-Asp-Cys) used to prepare coupons of Example 12, above. The RGDC solution comprises about 10 mg of the peptide in 10 mL of doubly distilled, Millipore™-filtered water. Coupons are stirred at ambient temperature for about 8 to about 48 hours. The coupons are removed from solution, dried, and rinsed in doubly distilled water. FTIR, analysis before and after peptide treatment demonstrates changes in the maleimide carbonyl region and broadening in the carboxylate region (~1700 cm$^{-1}$) which persists after two solvent rinses, indicating the presence of the RGDC tetrapeptide bound to the coupons.

It will be appreciated that peptides and amino acids can be "tagged" with a fluorescent marker by covalent bonding a small fluorescent species, such as dansyl chloride as an ester or thioester to the parent compound. It will be appreciated that amino acids and peptides which are bound to phosphonate species bonded to oxide surfaces, such as are described above can be tagged before or after such bonding reactions. When the surface species amino acid and peptide adducts are "tagged" in this manner, examination of the coupons by fluorescence microscopy after derivitization indicates the coatings of the peptide bounded to the coupon are dense and uniform over the entire coupon.

The next group of examples demonstrates the dense-coverage of a titanium native oxide surface that can be achieved with the coating of the present invention.

Examples 15-16

Formations of a Phosphonate Coating on a Titanium Quartz Microbalance Electrode

As described above, quartz microbalance electrodes were treated with octylphosphonic acid and 11-hydroxyundecylphosphonic acid to form octylphosphonate and 11-hydroxyundecylphosphonate coatings on the native oxide layer on the electrodes. The 11-hydroxyundecylphosphonate was further derivatized with maleimide and RGDC as described in example 11 above. The results of microbalance measurement of the density of surface coverage for the two species is presented below in Table 3.

TABLE 3

Surface coverage of Ti by phosphonates.

| Phosphonate | Δf (Hz) | Coverage (nmol/cm$^2$)* |
|---|---|---|
| Octylphosphonate | 109 | 1.49 (1.15) |
|  | 115 | 1.58 (1.21) |
| Average |  | (1.18) |
| 11-Hydroxyundecylphosphonate | 141 | 1.42 (1.09) |
|  | 115 | 1.15 (0.89) |
|  | 140 | 1.42 (1.08) |
|  | 135 | 1.36 (1.05) |
|  | 106 | 1.07 (0.82) |
|  | 135 | 1.36 (1.05) |
| Average |  | (1.00) |
| 11-Hydroxyundecylphosphonate - maleimide | 37 | 0.54 (0.42) |
|  | 31 | 0.45 (0.35) |
|  | 27 | 0.40 (0.31) |
| Average |  | (0.36) |
| 11-Hydroxyundecylphosphonate - maleimide-RGDC | 60 | 0.38 (0.26) |
|  | 47 | 0.23 (0.18) |
| Average |  | (0.22) |

*As measured by QCM; corrected value for surface roughness factor measured to be 1.3 by AFM analysis of the sputtered Ti electrode given in parentheses.

Example 17

Atomic Force Microscopy of an Octadecylphosphonate Coating

A coating of octadecylphosphonate on the native oxide surface of a polished titanium coupon was prepared by the aerosol method described above using a 0.75 mM THF solution of octadecylphosphonic acid. The acid solution was applied under nitrogen and evaporated using the ambient method. The spray-heat-rinse cycle was repeated 6 times. The resultant coating was studied by atomic force microscopy (AFM) using a Dimension 3000 (Digital Instruments) operated in "soft" TappingMode. An AFM micrograph of the polished Ti foil surface shows it to have grooves (resulting from the polishing process), but regions between these grooves are appreciably flat (mean roughness approximately equal to 0.7 nm). Section analyses examined surface roughness in more detail. The morphology of the surface changed dramatically on formation of the octadecylphosphonic acid film. On coated coupons, AFM micrograph and section analysis showed islands (typical diameter≈50 nm) of similar height ($\approx$2.2 nm), consistent with monolayer formation on the surface, and the mean roughness of the surface increased to 1.5 nm on monolayer attachment. With reference to film height data obtained for a self-assembled monolayer of this same phosphonic acid on mica ($\approx$1.8 nm), an alkyl chain tilt angle of about 33° was estimated. The AFM analysis indicates the coating is of dense-coverage. Correction of the microbalance results of Examples 15 and 16 by the AFM data indicate a surface coverage in excess of 20 times of that observed for reactions of the native oxide hydroxyl sites, described above.

The next example demonstrates the use of a functionalized alkylphosphonate coating of the present invention to bond a bone-growth promoting peptide RGDC (described above) to the surface of a titanium alloy (Ti—6Al—4V), and the use of this derivatized surface in adhering and proliferating osteoblasts.

Example 18

Application of a Phosphonate Coating to a Titanium Alloy and Subsequent Peptide Derivatization to Provide an Osteoblast Adhesion Promoting Surface Disks of Titanium Alloy Ti—6Al—4V prepared as described above were coated with a layer of 11-hydroxyundecylphosphonate by placing them in a vessel filled with a 10 mM THF solution of 11-hydroxyundecylphosphonic acid. The THF was allowed to evaporate and the disks were then baked in an oven at 120° C. for 48 hours and were rinsed in dry THF. Thus prepare the titanium alloy disks were further derivatized with the cysteine modified fibronectin cell attachment peptide Arginine Glycine Aspartic acid (RGDC) which has been described above.

The RGDC peptide [American Peptide] was bonded to the phosphonate coating using a maleimide coupling procedure. The maleimide derivative of the hydroxy functionalized phosphonate coating was prepared by placing the coated disk into a 5 mM acetonitrile solution of 3-maleimidopropionic acid-N-hydroxysuccinimide ester for a period of 24 hours at room temperature. Thus prepared the maleimide adduct was rinsed with a fresh acetonitrile solution. The disks were transferred into an acetonitrile solution of the peptide described above, RGDC, with stirring for 24 hours, yielding the peptide bound via a thiol-ether linkage through the cysteine residue to the hydroxy end of the phosphonate coating.

These modified titanium alloy disks were examined for their interaction with human osteoblasts. Human fetal osteoblasts (HFOB 1.19; ATCC) were maintained in a 1:1 mixture of Ham's F12 and Dulbecco's modified Eagle's medium (DMEM), without phenol red (GIBCO, BRL), 10% fetal bovine serum (Hyclone Laboratories) and 0.3 mg/ml G418 (GIBCO, BRL). Cells were labeled with 10 μM Cell Tracker Orange (Molecular Probes, OR) for 30 minutes at 34° C. After this time, the medium was removed and replaced with fresh medium and serum for an additional 30 minutes at 34° C. Cells were released from tissue culture dishes using 0.2 mg/ml EDTA in PBS, washed with PBS, re-suspended in serum-free medium at $1*10^5$/ml, and 500 μl of the cell suspension was added to wells containing the metal disk substrates which had been blocked with 1% BSA in PBS for 30 minutes before cell addition. Cells were allowed to spread on the substrates for 90 minutes, after which time they are washed with PBS and visualized using a Nikon Optiphot-2 microscope. Images were captured using a Photometrics Coolsnap camera and analyzed using Coolsnap and IP labs software.

The results of this study indicate that human osteoblasts can adhere and propagate on surfaces prepared according to the present invention.

Examples 4-17 were duplicated by treating coupons made from titanium alloy Ti—6Al—4V (Goodfellow) under the same conditions and with the same reagents used for the titanium coupons used in Examples 4-17. Results were the same, demonstrating that the coatings of the present invention can be applied equally well to the native oxide of titanium alloys using the methods of the present invention.

The next group of examples demonstrates the use of phosphoric acid to form an intermediate layer on titanium metal native oxide surfaces which may be further derivatized with other moieties, and a derivatized surface which can promote osteoblast adhesion and spreading.

Examples 19-24

Dip-Treatment of Titanium Native Oxide Surfaces in Phosphoric Acid Solution

In Example 19, a coupon of Titanium foil (99.6+% annealed), prepared as described above, was immersed in 1.4M aqueous $H_3PO_4$ (pH=1.5) at room temperature for one hour, then heated at 110° C. for greater than 16 hours. After two rinsings with THF, examination by DRIFT showed that it had a coating of $Ti(H_2PO_4)_3$ (Ti-phosphate) remained that could not be rinsed away.

In Example 20, titanium coupons prepared and described above were dipped in an aqueous solution of phosphoric acid (1.45 m; pH 1.5) for 1 hr at ambient temperature and pressure. The coupons were then removed from solution and warmed in an oven at 120° C. for 18 hours, then cooled, rinsed with water, and "peeled" with masking tape to remove any weakly adsorbed material. X-ray powder diffraction analysis and Diffuse Reflectance Fourier Transform Infrared analysis (DRIFT) confirmed the presence of phosphate coating (Ti-phosphate).

Coated coupons were prepared in accordance with Example 20 and further derivatized using the spray/heat/rinse procedure described above using the reagents indicated below in Table 4.

TABLE 4

| Example | Derivatizing Species | Solute conc./solvent | Baking temp./time |
|---|---|---|---|
| 16 | octadecyl(triethoxy)silane | 1.8 mM/THF | 120° C./24 hours |
| 17 | octadecanethiol | 1.0 mM/THF | 60° C./24 hours |
| 18 | octadecylamine | 1.0 mM/THF | 60° C./18 hours |
| 19 | octadecyl(triethoxy)silane | 0.8 mM/THF | 120° C./16 hours |

In each case, adherent, dense-coverage coatings of the reactant found on the surface of the phosphate coated coupon by IR analysis.

Example 25

Treatment of Phosphate Coatings With Hydrolytically Reactive Metal Alkoxides

Coupons prepared according to Example 20 were put in a horizontal tube which could be externally cooled and which was equipped with two stopcocks for exposure to vacuum ($10^{-3}$ Torr) or to vapor phase tetra-(tert-butoxy)zirconium (Zr(—O-t-butyl)$_4$). Coupons were subjected to three cycles each consisting of alternating exposure to vapor of Zr(—O-t-butyl)$_4$ with external evacuation for 15 minutes, followed by 30 minutes exposure to the organometallic reagent vapor without external evacuation. The first cycle was done at room temperature, and the latter two with external cooling by dry ice. Coupons were then subjected to room temperature vacuum ($10^3$ Torr) for 16 hours to remove any physisorbed Zr(—O-t-butyl)$_4$. DRIFT analysis confirmed formation of dense-coverage surface zirconium alkoxide.

Example 26

Derivatization of a Dense-Coverage Zirconium Alkoxide Bound to Titanium

Coupons prepared according to Example 25 were sprayed with 1.75 mM solution of octadecylphosphonic acid in dry tetrahydrofuran (THF). Samples were evacuated overnight (0.1 Torr), rinsed with THF, "peeled," tested and analyzed by DRIFT. The analysis demonstrated an adherent alkylphosphonate coating bonded to the zirconated surface.

The derivatization reactions of Examples 19-26 were repeated, using the same reagents and conditions on coupons of Ti—6Al—4V (Goodfellow) prepared according to the procedure described for Example 20 above. Analysis of the coatings prepared showed that titanium alloy can be derivatized in the same manner with the same results seen from the titanium.

The next group of examples demonstrates the use of a phosphate coating of the present development to provide a derivatized surface on a titanium material which promotes the adhesion and proliferation of osteoblasts.

Examples 27-28

Adhesion of Osteoblasts to a Titanium Material Phosphate Coated Peptide Derivatized Surface Disks cut from titanium billet and from titanium alloy Ti—6Al—4V billet were prepared and coated with a phosphate coating according to Example 20.

A phosphate coated disk of each material was placed in a Teflon™ well, and they were each treated with a solution of amino propyl(triethoxy)silane (10 mM in THF), and then solvent rinsed, with sonication, to give surface-bound 3-amino-propyl siloxanes. These disks were then further derivatized by placing each in a 5 mM acetonitrile solution of 3maleimidopropionic acid N-hydroxysuccinimide ester for 18 hours at room temperature to give the maleimide adduct. The disks were removed from solution, solvent evaporated, and analyzed by IR. They were then rinsed in acetonitrile, with sonication, and dried in vacuo (0.1 Torr). The disks were further derivatized by placing them into a solution of the RGDC peptide used in Example 18 above, (5 mM), prepared in 5 ml of purified water (Millipore), with the pH adjusted to 6.5 using 0.1M NaOH. The disks remained in the peptide solution stirring at room temperature for 24 hours. Formation of the surface bound RGDC was verified by IR. The disks were then rinsed with water, dried, subjected to tape peel testing, and reanalyzed by IR. The peptide coating was found to be adherent.

The peptide coated disks were subjected to the human osteoblast test described above in Example 18. The results showed that the surface promoted the adhesion and proliferation of osteoblasts.

Example 29

Derivitazation of Phosphate Coating with 11-Mercaptoundecanoic Acid

Mercaptoundecanoic acid was recrystallized from ethanol at room temperature. A solution of mercaptoundecanoic acid (1.0 mM in THF) was applied by aerosol deposit onto coupons of titanium and of titanium alloy Ti—6Al—4V. The coupons were placed under $N_2$ for 6-12 hours in a horizontal tube equipped with a stopcock to regulate $N_2$ flow and pressure, then evacuated at 0.1 Torr for at least 4 hours, and analyzed by DRIFT. A dense coating of the mercaptan was found adhered to the surface of both the metal and alloy.

Next is presented an example of using a bisphosphonic acid to provide an adherent coating layer which is further derivatized to form a coating having a phosphonate segment and a linking segment. Additional examples are presented in which this segmented coating layer is further derivatized to provide a peptide-bearing surface, a calcium apatite surface and a mixture of peptide and calcium apatite.

Example 30

Derivatization of the Native Oxide Surface of Ti—6—Al—4—V Titanium Alloy by Formation of a Surface Coating Layer Having a 1,6-Diphosphonohexane Segment and a Linking Segment A coupon of Ti—6—Al—4—V titanium alloy (extra low interstitial grade ⅜" diameter rod, from Titanium Industries, Morristown, N.J.) was prepared by cutting 1 mm sections from the rod stock using an art recognized wire electric discharge cutting technique. The surface of the coupon was prepared by sanding and then successively washed with methylene chloride, 2-butanone, and then methanol. After a methanol rinse, the coupons were stored under air in an oven at 200° C.

The bisphosphonic acid was synthesized and purified according to published procedures; all other reagents were used as received. A coating layer was applied to the coupon by dropwise application of a 1.0 mM aqueous solution of the 1,6-hexane-bis(phosphonic acid) onto the surface of the coupon under ambient conditions and transferring the sample into a 120° C. oven in air for 48 hours. At the end of the baking period, the samples were rinsed with distilled water, sonicated in distilled water for 20 minutes (Branson 2610 Sonic Cleaner), and dried in vacuo at ambient temperature (about 0.01 mm Hg for 5 hours). The presence of a bisphonate layer was verified by infrared (IR) analysis as described above.

Preparation of a Coating Layer Having a Bisphosphonate Segment and an Alkoxide Linking Segment The surface of the bisphosphonate coating layer on coupons, prepared as described above, was further derivatized by reaction with a zirconium alkoxide. Thus, a coupon coated as described above was placed into a vacuum deposition chamber which was fitted with a bulb containing freshly vacuum distilled zirconium tetrakis(tert-butoxide). The chamber was closed and evacuated to 5.5 millitorr. The chamber was sealed from the vacuum source and the bulb was opened, admitting zirconium alkoxide vapor to a pressure of about 3 millitorr for 30 minutes at ambient temperature. The chamber was again evacuated to 5.5 millitorr and the cycle repeated twice more. At the end of the third exposure to zirconium alkoxide, the sample was subjected to a vacuum of 3 millitorr for two hours. The presence of the zirconium linking segment bound to the surface coating layer was verified by IR analysis, as described above. Coupons having a segmented coating layer prepared according to this procedure were further handled in a nitrogen glove box.

Preparation of a Coating Layer Having Bound Peptide

The coupons having a coating layer comprising a bisphosphonate segment and an alkoxide segment (segmented coating layer), prepared as described above, were subjected to further derivitization reactions to bind a peptide to the zirconium alkoxide linking segment. This was accomplished by reacting the residual alkoxide moieties with a difunctional organic acid (6-maleimido-hexanoic acid, Sigma, used as received), bonding the carboxylate functional group to the zirconium. The surface bound acid was then reacted at the maleimide functional group with a peptide derivative. Thus, an anhydrous 1.0 mM tetrahydrofuran (THF) solution of the carboxylic acid was aerosol sprayed in a dry box onto the coupon prepared as described above, according to the aerosol procedure described above. The samples were subjected to a vacuum of about 0.01 torr for 12 hours, then rinsed and sonicated in THF and dried again in vacuo. The binding of the carboxylic acid species to the zirconium segment of the coating layer was verified by IR analysis, as described above. A 2 mM aqueous solution of the cysteine modified RGD peptide (RGDC) described above was adjusted to pH 6.5 with NaOH. Coupons which had been previously derivatized with 4-maleimidobutyric acid were stirred in the RGDC peptide solution at 25° C. for 24 hours.

The coupons which were derivatized with RGDC peptide were incubated with human fetal osteoblasts, as described above. These surfaces were found to promote cell attachment and proliferation.

Example 31

Preparation of a Coating Layer Having a "Patterned" Alkoxide Linking Segment Surface It will be found that application of a small droplet of a solution of zirconium tetrakis(tert-butoxide) (prepared as described above in Example 30) to the surface of a coating layer prepared from 1,6-hexanediphosphonic acid in accordance with the process described in Example 30 will provide a zirconium alkoxide linking segment confined to the area of the surface contacted by the droplet. By applying small droplets to the surface in selected areas it will be found that subsequent treatment of the surface with 6-maleimido-hexanoic acid in accordance with the procedure described for Example 30 will provide bonding of the carboxylic acid to the surface only in those areas which were contacted by the zirconium alkoxide. It will be found that subsequent treatment of the surface with RGDC peptide according to the procedure described above in Example 30 will yield a surface which has a "pattern" of the peptide bound to the surface only in those areas of the surface having the zirconium alkoxide linking segment.

It will be appreciated that the surface can be provided with a "pattern" using the process described in Example 31 by contacting the surface with a solution of the zirconium alkoxide through a "mask", or by direct application of a solution to the surface in a pattern, or by any of the known techniques for application of a pattern, for example, by "inkjet" printing or by "screen" printing.

Example 32

Formation of Calcium Hydroxyapatite Surface

It will be found that when the bisphonate coating layer prepared as described in Example 30 is subsequently reacted with a calcium alkoxide instead of a zirconium alkoxide, there is provided a segmented coating layer having a bisphosphonate segment bonded to the native surface oxide layer and a calcium alkoxide linking segment bonded to the bisphosphonate segment (hereafter, calcium-functionalized coating layer). It will also be found that a calcium-functionalized coating layer provides a surface upon which a synthetic calcium apatite surface can be formed by sequentially reacting the calcium-functionalized coating layer with phosphoric acid and a calcium alkoxide reagent. Thus, by substituting calcium-bis(2-methoxy ethoxide) for zirconium tetrakis(tert-butoxide) in the procedure described above for the preparation of a coating layer having a zirconium alkoxide linking segment (Example 30), a segmented coating layer having bisphosphonate segment bonded to the native oxide layer of a titanium coupon and a calcium alkoxide segment bonded to the bisphosphonate segment will be prepared.

It will be found that by reacting the calcium alkoxide functionalized coating thus prepared with an aqueous solution of phosphoric acid, a calcium hydroxy-phosphate surface is prepared. It will be found that by alternatively reacting the surface thus prepared with additional amounts of calcium bis(2-methoxy ethoxide) and phosphoric acid, a calcium hydroxy-phosphate surface layer of suitable thickness to permit growth of an adherent layer of hydroxyapatite on the surface using known sol-gel processing techniques is provided.

Example 33

Preparation of "Mixed" Pattern Surfaces

It will be found that a coating layer prepared from treatment of a titanium coupon with a solution of 1,6-hexanediphosphonic acid according to the process described in Example 30 can be provided with a pattern comprising interspersed regions of osteoblast adhesion-promoting peptides and hydroxyapatite by patterning the surface first with a peptide that promotes osteoblast adhesion using the process described in Example 31 to pattern the surface with zirconium linking segments, attaching to the zirconium linking segments (6-maleimido) hexanoic acid according to the process described in Example 30, and then further derivatizing the surface of the coating layer with a calcium alkoxide linking segment in the areas not receiving a zirconium alkoxide linking segment by reacting the surface with a solution of calcium bis(2-methoxy ethoxide) according to the procedure described in Example 32. It will be found that such a surface will promote osteoblast adhesion and bone tissue infiltration into the surface when the surface is placed into contact with living bone tissue.

Example 34

A Phosphonate/Epoxide Segmented Coating Layer

Titanium coupons having a coating prepared according to Example 3 above (a phosphonate coating derived from 11-hydroxyundecylphosphonic acid) were further derivatized with an epoxy linking group by applying a film of Cytec Fiberite FM 1000™ epoxy adhesive to the surface. Before the adhesive cured, a second titanium coupon prepared according to Example 3 was placed in contact with the epoxy such that a lap joint was formed having a 284 mm² area. The epoxy was permitted to dry under ambient conditions. Additional examples were prepared from titanium metal coupons having a sanded, washed, and baked surface, as described above, but without a phosphonate coating. The strength of the joint between the coupons for the coated and uncoated samples was tested according to ASTM testing standard F1044-99. It was found that on average, the joint between the uncoated coupons failed at 40 MPa and between the coated coupons, the joint failed on average at about 60 MPa of applied pressure.

Example 35

Shear Testing of Phosphonate Coatings

Figure 11:
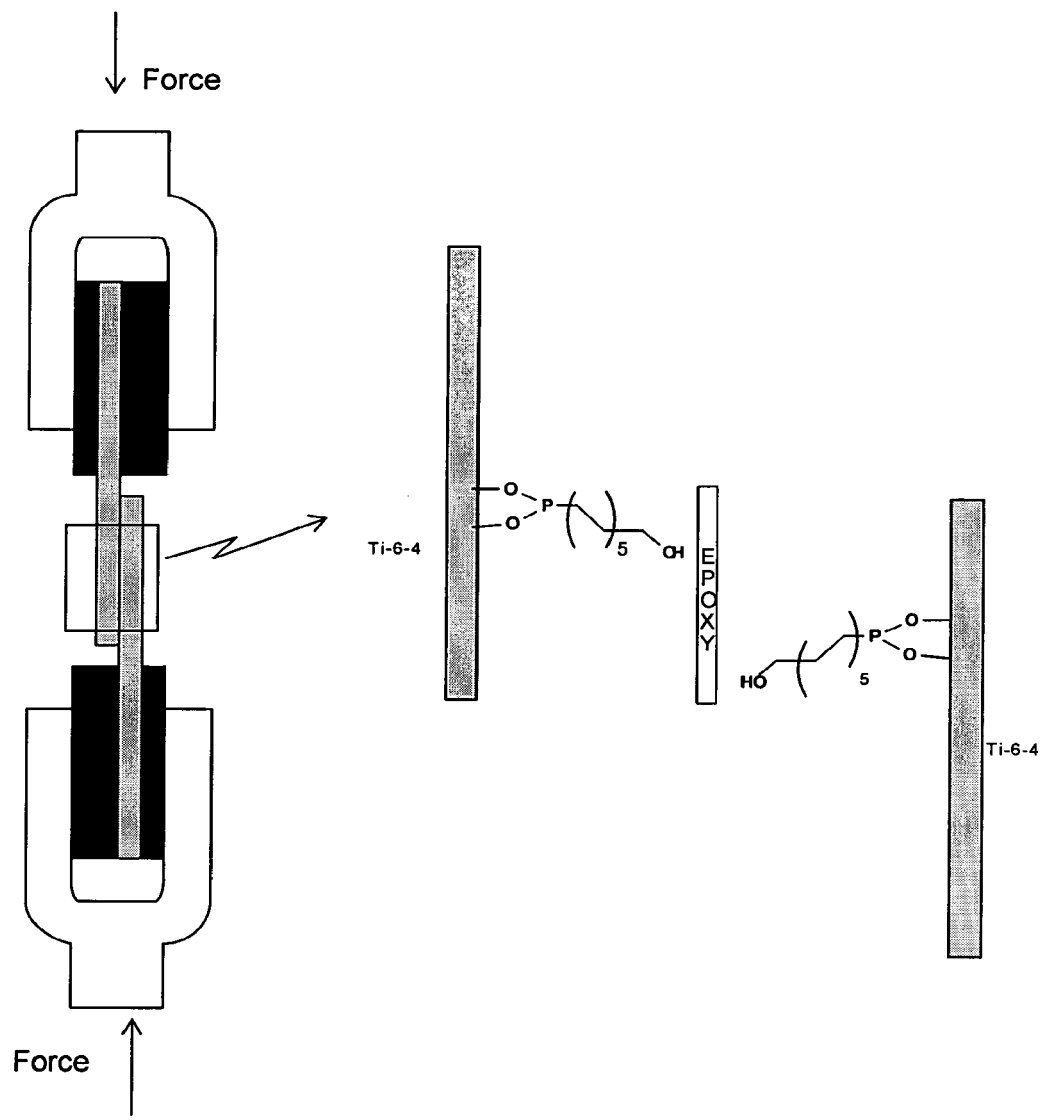
FIG. 11 shows an example of a coating shear strength testing apparatus.

To test the Mode I (shear) stress of the various interfaces, a modified version of ASTM test 1044-99 was used. Coupons of titanium metal and titanium alloy (Ti—6Al—4V) (2"× ½"×⅛") were cut via electric discharge machining and were polished. Surfaces were solvent cleaned and stored at 200° C. until use. Surface SAMs (self-assembled monolayers) were grown by the T-BAG method described in U.S. patent application Ser. No. 10/701,591; coupons were suspended vertically in a 0.1 mM solution of the appropriate phosphonic acid and the solvent was allowed to traverse the surface, leaving a SAM of the phosphonic acid. The SAM was then covalently bonded to the surface as the phosphonate by heating to 140° C. for 48 hours. The coupons were then rinsed extensively with solvent and were analyzed by IR after each rinse. The IR spectra after rinsing demonstrated ordered phosphonate films in which substantially all the phosphonate were covalently bound by at least on one oxygen to the oxide surface of the coupon. Treated coupons were then joined together using Cytec Fiberite Epoxy FM-1000, with a spatial overlap as stipulated by ASTM 1044-99. Curing was performed in a holder, and coupon "sandwiches" were then heated in a programmable furnace, slowly ramping the temperature from room temperature to 170° C. The oven temperature was then held at 170° C. for 90 minutes and was ramped back down to room temperature. Once cured, the sandwiches were placed in a holder to ensure that any force applied is shear (Mode I). The sandwich and holder were placed in an Instron 1331 load cell and a controlled amount of force was applied until failure of the interface occurred, the failure stress was noted. See FIG. 11. Shear stress measurements were conducted on uncoated coupons and on coupons coated with octadecylphosphonate (Ti-Phosphonate18), 11-hydroxy-undecylphosphonate (Ti-Phosphonate-OH), 12-phosphonododecylphosphonate (Ti-Phosphonate-12P), 4-phosphonobutylphosphonate (Ti-Phosphonate-4P), 4-phos-phono-2-butene-1-phosphonate (Ti-Phosphonate-4'P), cross linked 4-phosphono-2-butene-1-phosphonate (Ti-Phosphonate-4'P cross linked), 4-phosphono-p-xylenylphosphonate (Ti-Phosphonate-4XP), and 4-p-anthracenylphosphonate (Ti-Phos-phonate-4A). Surface loadings which for the present invention is equivalent to surface phosphorous-containing group densities, were also measured via QCM as described above. The test results are shown in Table 5 below.

Because strengths of the interfaces on Ti were measured mechanically, only the lower limit for the shear strength of Ti-Phosphonate-OH>52 MPa could be determined because the epoxy, not the interface, fractured.

Differences in interfacial shear strengths of the other comparably loaded interfaces may be attributed to the respective tail group reactivities with the epoxy. In the case of Ti-11-hydroxyundecylphosphonate, the high molecular surface density in the interface also provides a closely packed film of nucleophilic —OH at the film terminus.

TABLE 5

Maximum shear strength and loading of functionalized/derivatized titanium surfaces.

| Sandwich Substrate | Macroscopic Interfacial Shear Strength (MPa) | Surface Loading (nmol/cm²) |
|---|---|---|
| Uncoated Ti—6Al—4V | 40.1 ± 2.9 | N/A |
| Ti-Phosphonate-18 | 11.9 ± 3.5 | 1.18 ± 0.03 |
| Ti-Phosphonate-OH | >52.1 ± 2.1 | 1.00 ± 0.03 |
| Ti-Phosphonate-12P | 51.4 ± 3.1 | 0.52 ± 0.02 |
| 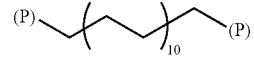 | | |
| Ti-Phosphonate-4P | 40.0 ± 4.0 | 0.40 ± 0.03 |
| 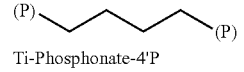 | | |
| Ti-Phosphonate-4'P | 71.2 ± 7.4 | 0.77 ± 0.01 |
| 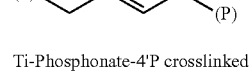 | | |
| Ti-Phosphonate-4'P crosslinked | 50.3 ± 2.4 | 0.77 ± 0.01 |
| 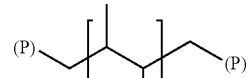 | | |
| Ti-Phosphonate-4XP | 41.1 ± 2.6 | 0.25 ± 0.01 |
| 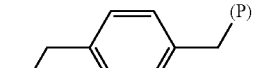 | | |
| Ti-Phosphonate-4A | N/A | 0.1 ± 0.03 |

All interfacial shear strengths exceeded the FDA minimum (20 MPa) required for sprayed coatings on surgical implants except for titanium surfaces coated with octadecylphosphonate. See, e.g., U.S. Provisional Application No. 60/684,159.

The sandwiches made from titanium surfaces coated in octadecylphosphonate (Ti-Phosphonate-18) had the weakest composite shear strength, consistent with the surface being covered essentially by a grease: although the phosphonate-titanium interface may be strong, the methyl-terminus of the SAM affords no points of attachment for the epoxy, and thus the epoxy can simply slide off of the SAM-coated titanium.

The ω-modified SAMs show marked increases in their composite shear strength from that of the methyl-terminated SAM. The sandwiches made from hydroxyl-terminated SAM and the phosphonate-terminated SAM have reactive tail groups that are able to chemically bond to the epoxy. As such, the epoxy can be firmly attached to the SAM-coated titanium. Most importantly, SAM coated titanium composites have shear strength greater than that of native Ti—6Al—4V. The fact that composite shear strength is increased (above the benchmark of the FDA) over untreated titanium is attributed to a greater number of reactive sites on the ω-functionalized SAM films than on native Ti—6Al—4V (the native oxide surface of titanium has only about 16% hydroxyls of its surface oxygen content or lower when treated with high temperatures prior to exposure to oxygen).

In order to test the dependence of shear strength on alkyl chain length for a phosphonate-titanium interface, a short chain diphosphonate film of (4-phosphonobutylphosphonate) was prepared on the surface of titanium. This surface was analyzed via IR to gauge any ordering of the alkyl chains, however $v_{CH2}$ could not be detected, most likely due to the short chain length. However, a broad band for the phosphonate was observed ($v_{PO}$≈1200-1050 cm$^{-1}$). The shear strength of this interface was measured (40.0±4.0 MPa), which is less than that of the 12-carbon analog (>50 MPa). This difference in interfacial shear strength may be attributed to chain length, but differences in surface loadings between the two phosphonic acids were also measured (Table 5): it may be that the greater van der Waals interactions between longer chains may help facilitate ordered SAM formation which may lead to greater surface densities for Ti-Phosphonate-12P (1,12-diphos-phonododecane) than for its C-4 analog and hence greater interfacial shear strength.

Loadings of both Ti-Phosphonate-12P and Ti-Phosphonate-4P were determined gravimetrically via quartz crystal microgravimetry (QCM) (Table 5 above). From these loading data, it is seen that the strength of the interface as measured is proportional to the diphosphonate loading of the surface. If the interfacial shear strength is normalized on a per molecule basis, interfacial shear strengths of long and short chain phosphonates per molecule are the same: the greater loading of Ti-Phosphonate-12P vs. Ti-Phosphonate-4P leads to a greater number of sites of attachment between the surface and the SAM, and between the SAM and the epoxy, thus leading to greater composite shear strength for the longer chain system.

The structure of the alkyl chain was also varied. SAMs of 4-phosphono-2-butene-1-phosphonate were prepared on Ti (Ti-Phosphonate-4'P) to give a SAM containing an olefinic group. Upon exposure to ultraviolet radiation, the SAM was forced to crosslink. SAMs of 4-phosphono-p-xylenyl-phosphonate were prepared on Ti (Ti-Phosphonate-4XP), yielding a surface film containing an aromatic group. SAMs of Ti-Phosphonate-4'P without crosslinking demonstrated the same trend as observed for Ti-Phosphonate-12P and Ti-Phosphonate-4P (i.e. greater loading leads to greater shear strength). Upon crosslinking, the SAM of Ti-Phosphonate-4'P underwent a reduction in interfacial strength, although not losing film loading, demonstrating a dependence of film structure on its shear strength. In further demonstration, SAMs of Ti-Phosphonate-4XP had less shear strength than either Ti-Phosphonate-12P, Ti-Phosphonate-4P, or Ti-Phosphonate-4'P, but this shear strength did not scale simply with film loading; there may be a dependence on film structure in that the aromatic group apparently adds strength to the system.

It will be appreciated that phosphorous and phosphonate based coatings may also be prepared and covalently bound to implantable surfaces at lower surface loading densities. The shear strength of these less densely coated surfaces will be less then the shear strength of the tightly packed coated surfaces listed in Table 5. For example, the shear strength coatings with lower surface loading densities will be, for example, about 35 MPa or about 30 MPa or even at least about 20 MPa.

Example 36

Tensile Testing of Phosphonate Coatings

Figure 12:
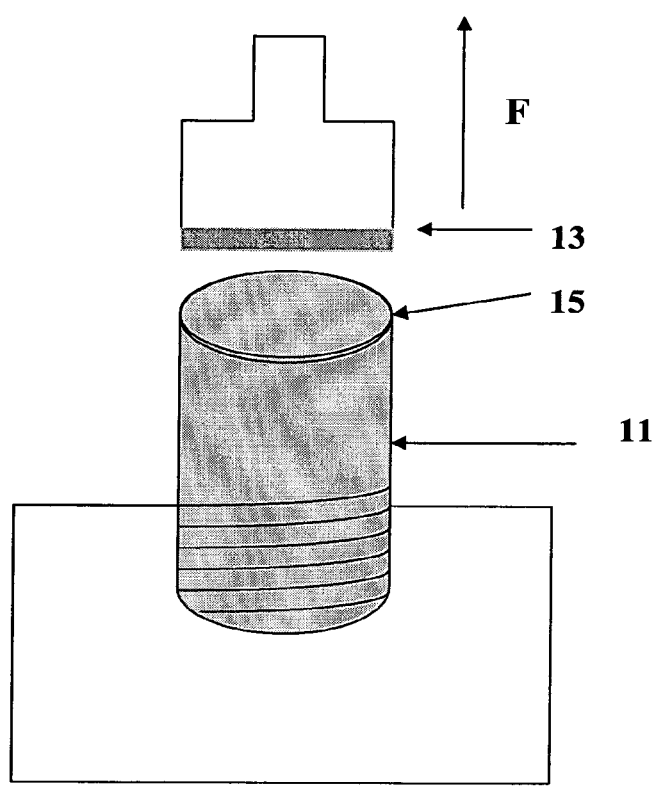
FIG. 12 shows an example of a coating tensile strength testing apparatus.

Tensile strength is an important factor for evaluating interfacial adhesion of coatings on devices. Tensile strength tests of the coatings disclosed herein were conducted using a modified version of ASTM Test #1147-99 with a testing apparatus similar to that shown in FIG. 12. The smooth flat surface of a threaded titanium or Ti—6Al—4V cylindrical fitting 11 was coated with 11-hydroxyundecylphosphonate according to the methods disclosed herein. This was affixed to a matched piece of untreated titanium 13 using Cytec FM-1000 epoxy layer 15. Tensile load (F) was applied to each test specimen at a constant rate until separation of the components was been achieved.

The failure point of was measured to be 81.1 MPa, statistically similar for the failure points for uncoated (82.7 MPa) and uncoated grit blasted (84.5 MPa) samples. The tensile strength for the epoxy was reported to be ~82 MPa, so it is likely that for each sample, the failure of the epoxy layer was what took place during testing. Each interface exceeds this strength, but attaining a value at failure would not be possible without a stronger epoxy bonding layer.

It will be appreciated that the tensile strength of alternate phosphonate coatings, particularly alkylphosphoate coatings, for example. Octadecylphosphonate, will be lower than ~82 MPa, for example at least about 70 Mpa, or at least about 60 MPa, or at least about 40 MPa-50 MPa. In addition, it will be appreciated that phosphorous and phosphonate based coatings may also be prepared and covalently bound to implantable surfaces at lower surface loading densities. The tensile strength of these less densely coated surfaces will be less then the shear strength of the tightly packed coated surfaces. For example, the tensile strength of coatings with lower surface loading densities will be, for example, about 50 MPa or about 35 MPa or about 30 MPa or even at least about 20 MPa.

Example 37

Ostoblast Adhesion on RGD-Coated Phosphonate-Functionalized Titanium

While the shear strength of the chemical films on implant materials is important, often the limiting factor of implant stability is the bone-implant interface. A common guide to measure the osteointegration of potential implant surfaces is to monitor osteoblast adhesion and spreading through in vitro cell studies. The efficacy and biocompatibility of the films were then tested in short term in vitro cell studies. Samples of titanium and Ti-Phosphonate-OH processed with RGD and Ti-Phosphate-OH processed with RGD were exposed to human fetal osteoblast culture.

In Vitro Cell Adhesion Studies

Human fetal osteoblasts (HFOB 1.19; ATCC) were maintained in a 1:1 mixture of Ham's F 12 and Dulbecco's modified Eagle's medium (DMEM) without phenol red (GIBCO, BRL), 10% fetal bovine serum (Hyclone Laboratories) and 0.3 mg/ml G418 (GIBCO, BRL). Cells were labeled with 10 μM Cell Tracker Orange (Molecular Probes, OR) for 30 min at 34° C. After this time, the medium was removed and replaced with fresh medium and serum for an additional 30 min at 34° C. Cells were released from tissue culture dishes using 0.2 mg/ml EDTA in PBS, washed with PBS, resuspended in serum-free medium at $1 \times 10^5$/ml, and 500 ml of the cell suspension was added to wells containing the alloy substrate disks which had been blocked with 1% BSA in PBS for 30 min before cell addition. Cells were allowed to remain on the substrates for specified periods of time. Samples were washed with PBS and visualized using a Nikon Optiphot-2 microscope. Images were captured using a Photometrics Coolsnap camera and analyzed using Coolsnap and IP labs software. A quantitative assessment of cell coverage was carried out by counting the number of cells from three random fields per substrate (0.52 mm$^2$); values are expressed as the mean number of cells present.

To test the stability of the interfaces under physiological conditions and to determine their efficacy for cell adhesion and spreading, human fetal osteoblasts were incubated with unmodified or variously surface-modified Ti—6Al—4V ELI for 90 minutes, 24 hours, and 3 days. Cells were previously tagged with a fluorescent marker so that cell adhesion, spreading, and counting could be monitored by fluorescence microscopy. Very little osteoblast adhesion occurred on unmodified Ti—6Al—4V ELI or ω-hydroxy-terminated alkylphosphonate-modified surfaces. A striking observation was made for the Ti-Phosphate-modified surface, where cell adhesion was initially quite efficient. Without being bound by theory, it is believed that the presence of exposed phosphate groups of Ti-Phosphate in conjunction with chemically bonded RGD creates an especially attractive mixed-function environment for the osteoblasts. Unfortunately, the inherent hydrolytic instability of Ti-Phosphate affects the long-term viability of this interface; after 3 days, loss of surface material was visually apparent. An RGD-modified silane/Ti—6Al—4V surface underwent a similar process in which initial osteoblast adhesion was marked for 24 hours, but showed signs of failure after 3 days. This indicates that the surface bound siloxanes may be hydrolytically labile after prolonged exposure to physiological conditions. In contrast, adhesion and spreading of the osteoblasts on RGD-modified phosphonate: Ti—6Al—4V were quite substantial after 24 hours and even more so after 3 days. The morphology and actin cytoskeleton of cells were observed by staining with rhodamine phalloidin. Cells remained small and rounded with no organized actin cytoskeleton on control substrates. However, more than 90% of cells adherent to RGD-modified substrates became well spread and organized their actin filaments into robust stress fibers. See, e.g., U.S. Provisional Application No. 60/684,159.

Example 38

Cell Resistance and Oxidative Stability of Modified Titanium Surfaces

As set forth in U.S. Provisional Application No. 60/684, 159, two methods were used to surface-treat disks of Ti—6Al—4V with methyl-terminated poly(ethylene glycol). The first involved simply reacting methyl-terminated poly (ethylene glycol) (mPEG) succinimidoyl propionate (MW 5000 Da) with otherwise untreated disks. The Ti-mPEG surface was analyzed by IR and showed peaks corresponding to $v_{CH_2, asymm} \approx 2925$ cm$^{-1}$, $v_{CH_2, symm} \approx 2850$ cm$^{-1}$, $C_{C(O)OC} \approx 1734$ cm$^{-1}$, $v_{EG\ CH_2\ wag} \approx 1346$ cm$^{-1}$, $v_{EG\ CH_2\ twist} \approx 1225$ cm$^{-1}$, and $v_{C-O-C} \approx 1085$ cm$^{-1}$. Reproducibly coating the surface this way was problematic because of the low surface —OH content of the Ti—6Al—4V native oxide. In the second, mPEG was covalently bound to an omega-hydroxy-functionalized phonsphonate titanium surface. The Ti-11-hydroxyundecyl-phosphonate-mPEG surface was analyzed by IR and showed peaks indicative of hydroxy-functional phosphonated titanium, as well as for PEG ($v_{C(O)OC} \approx 1734$ cm$^{-1}$, $v_{EG\ CH_2\ wag} \approx 1352$ cm$^{-1}$, $v_{EG\ CH_2\ twist} \approx 1215$ cm$^{-1}$, and $v_{C-O-C} \approx 1085$ cm$^{-1}$; the latter peak overlaps with $V_{P=O}$ of the underlying monolayer). The third film was a self-assembled monolayer of 11-hydroxyundecylphosphonic acid, which has been described previously. This latter Ti-11-hydroxyundecylphosphonate surface typically exhibits FTIR peaks at ~2920-2910 cm$^{-1}$ (—CH$_2$—, having a peak width at half-height from about 2 to about 10 wavenumbers, also from about 3 to about 8 wavenumbers) and at ~1090 cm$^{-1}$ (—P═O/—P—O, having a peak width at half-height from about 15 to about 45 wavenumbers, or for example from about 20 to about 40 wavenumbers, for example of about 30 wavenumbers).

Human fetal osteoblasts were cultured with untreated alloy discs and the three surfaces described above. After 90 minutes, essentially no cells were attached to any of these surfaces, demonstrating cell resistance at this early time point. After 24 hours, the differential effectiveness of the surface treatments was noticeable. Both PEG-treated surfaces (first and second above) showed greater resistance to osteoblast adhesion compared to the untreated alloy, but Ti-mPEG was the less effective of the two. Some areas of the surface of Ti-mPEG resisted cellular adhesion, but these were intermixed with regions showing an increased number of attached cells which had spread; this may be due to incomplete surface coverage of the Ti by reaction with the mPEG succinimidoyl propionate. Significantly, the simple phosphonate monolayer Ti-11-hydroxyundecylphosphonate (third film) was as effective in resisting osteoblast adhesion as was Ti-11-hydroxyundecylphosphonate-mPEG, with only a small number of poorly spread cells present.

Figure 2:
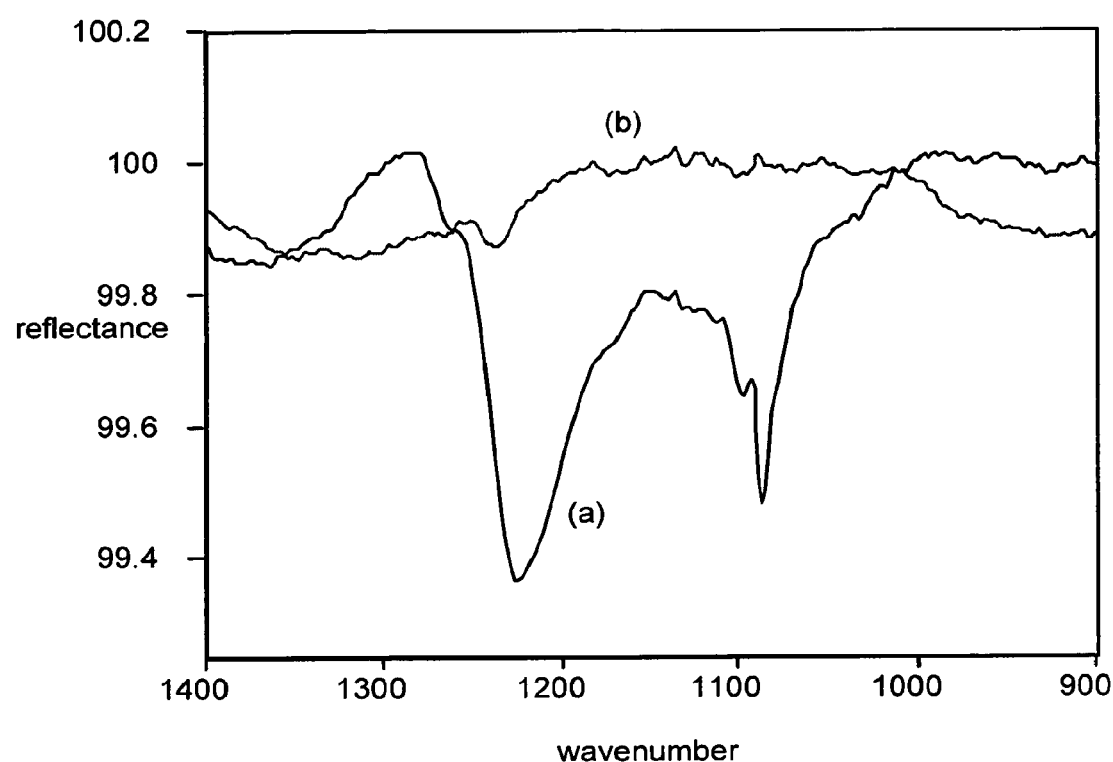
FIG. 2 shows IR spectra of Titanium coated with methyl-terminated poly(ethylene glycol), (a) pre- and (b) post-treatment with the Fenton like reagent.
Figure 3A:
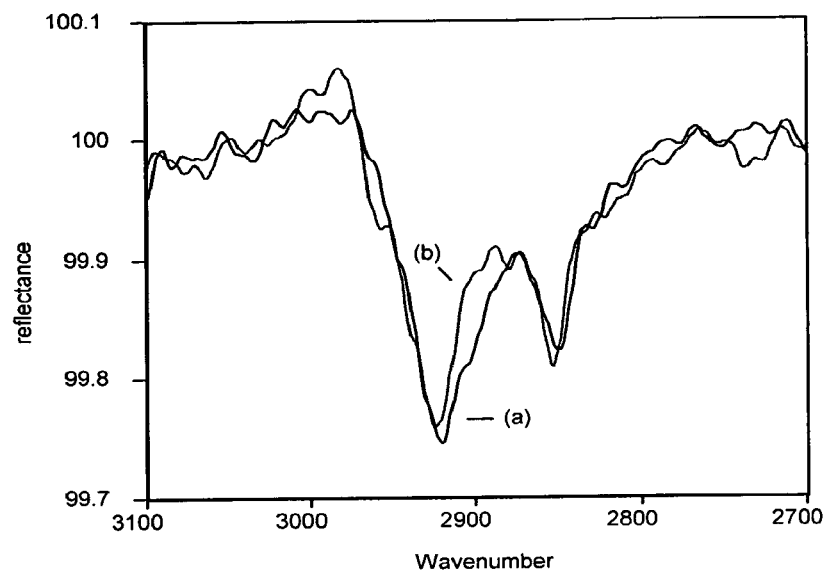
FIGS. 3(a) and 3(b) show IR spectra of Titanium coated with 11-hydroxyundecylphosphonic acid, (a) pre- and (b) post-treatment with the Fenton like reagent between FIG. 3(a) 2700-3100 wave numbers and FIG. 3(b) 1025-1125 wave numbers.
Figure 3B:
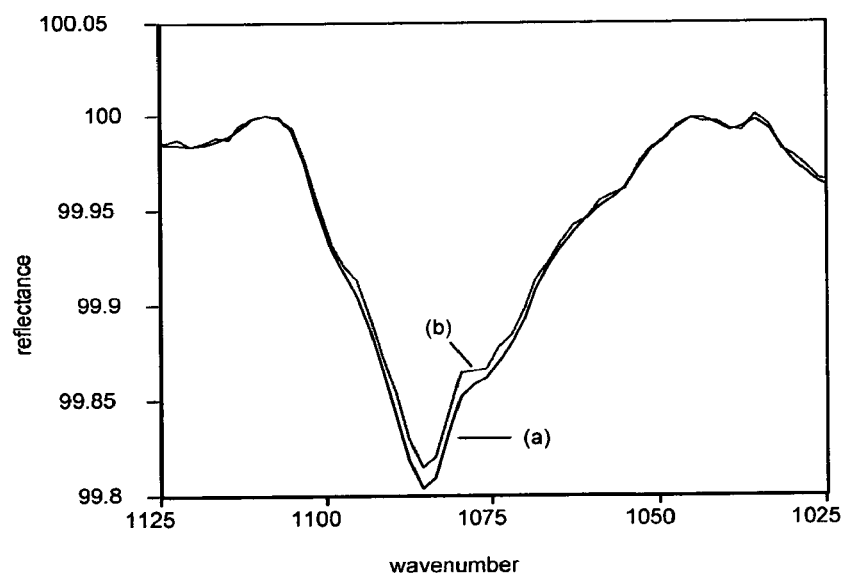

The resistance to oxidation of Ti-mPEG, as well as Ti-11-hydroxyundecylphos-phonate and Ti-11-hydroxyundecylphosphonate-mPEG, were probed using a "Fenton-like" reagent (FLR) mixture of TiCl$_3$, EDTA and 30% aq. H$_2$O$_2$, in a ratio of TiCl$_3$:EDTA:H$_2$O$_2$ of ~14 mM:~14 mM:~80 mM. In particular, a solution of oxidant was prepared in 50 ml Milli-Q water by sequential addition of 0.1 g TiCl$_3$, 0.27 g EDTA, and 0.45 ml of 30% H$_2$O$_2$; the pH of this solution was adjusted to ~7.5 using 0.5 M potassium carbonate. This system is an active source of hydroxyl radical and is known to be an aggressive oxidant that mimics macrophage induced oxidation in response to immunological challenge. Resistance to such oxidation was first noted qualitatively using FTIR before and after treatment. Noteworthy are the observations for Ti-11-hydroxyundecylphosphonate and Ti-11-hydroxyundecylphosphonate-mPEG (FIG. 1) and Ti-mPEG (FIG. 2) surfaces that peaks at ~1215 cm$^{-1}$ ($v_{EG\ CH_2\ twist}$) and at ~1085 cm$^{-1}$ (overlapping $v_{C-O-C}$ and $v_{P=O}$), were markedly diminished by this treatment; in particular, no absorption remained at ~1085 cm$^{-1}$ when DANSYL-ated TiP was treated with the FLR, but the peak at ~1085 cm$^{-1}$ for oxidized Ti-11-hydroxyundecylphosphonate-mPEG was reduced in intensity to that of the starting film of Ti-11-hydroxyundecylphosphonate. In contrast, the spectrum for Ti-11-hydroxyundecylphosphonate (FIGS. 3(a) and 3(b); $v_{CH2, asymm}=2917$ cm$^{-1}$; $v_{CH2,symm}=2848$ cm$^{-1}$; $v_{P=O}=1085$ cm$^{-1}$) was essentially unchanged, and no evidence was found for any carboxylic acid or aldehyde degradation products. Indeed, oxidation of Ti-11-hydroxyundecylphosphonate-mPEG yielded a material that by IR was nearly identical to independently prepared Ti-11-hydroxyundecyl-phosphonate.

Comparative oxidative stability of films Ti-11-hydroxyundecylphosphonate and Ti-11-hydroxyundecylphosphonate-mPEG was assessed quantitatively via fluorescence spectroscopy of surfaces that were derivatized by DANSYLation. In particular, as shown in Table 6 below, Ti-11-hydroxyundecylphosphonate (1 nmol/cm$^2$ surface —OH group density by QCM) is not significantly degraded by exposure to the FLR. This stability may be due to the highly ordered packing of the alkyl chains in the monolayer of Ti-11-hydroxyundecylphosphonate which makes ether group —C—H bond abstraction sterically difficult; such abstraction processes are believed to involve oxygen-stabilized intermediate radicals, which may not be conformationally accessible in the tightly packed film. Simple Ti-mPEG was significantly degraded by the FLR, as shown by IR.

Treating Ti-11-hydroxyundecylphosphonate-mPEG with the FLR also resulted in a noticeable reduction in intensity of PEG-related peaks ($v_{EG\ CH_2\ twist}\approx 1215$ cm$^{-1}$, $v_{C-O-C}\approx 1085$ cm$^{-1}$) in the IR; indeed the IR spectrum of Ti-11-hydroxyundecylphosphonate-mPEG after treatment with the FLR closely resembles that of the starting Ti-11-hydroxyundecylphosphonate. Apparently, radical-initiated cleavage of PEGylated species is not sterically inhibited as it is in Ti-11-hydroxyundecylphosphonate. Oxidative removal of sterically large mPEG groups should expose —OH sites of Ti-11-hydroxyundecylphosphonate to become available for DANSYL coupling, and indeed after Ti-11-hydroxyundecylphosphonate-mPEG was treated with the FLR, the yield of surface DANSYLation actually increased from ~0.17-0.31 nmol/cm$^2$, approaching that for TiP, itself. Thus, it seems that whereas oxidizing conditions substantially degrade the PEG in Ti-11-hydroxyundecylphosphonate-mPEG, they leave the underlying film of Ti—11-hydroxyundecylphosphonate intact.

TABLE 6

Surface coating loadings determined by fluorescence spectroscopy.

| Surface Coating | Loading by QCM (nmol/cm$^2$) | DANSYLated derivative Loading by S (nmol/cm$^2$) | |
|---|---|---|---|
| | | Pre-Oxidation | Post-Oxidation |
| Ti-11-hydroxyundecylphosphonate | 1.00 ± 0.09 | 0.41 ± 0.10 | 0.39 ± 0.11 |
| Ti-11-hydroxyundecylphosphonate-mPEG | 0.11 ± 0.02 | (0.33 ± 0.07; byQCM) | |
| Ti-mPEG | 0.01 ± 0.01 | 0.17 ± 0.04 | 0.31 ± 0.08 |

As a check on this method, surface loadings for "pre-oxidation" Ti-11-hydroxy-undecylphosphonate and Ti-11-hydroxyundecylphosphonate-mPEG species as determined by cleavage/fluorescence spectroscopy were compared with those measured gravimetrically by QCM. Since the amount of DANSYL fluorophore on Ti-11-hydroxyundecylphosphonate is similar in both pre- and post-treatment species (0.41 and 0.39 nmol/cm$^2$, respectively, as measured by cleavage/fluorescence), we conclude that TiP is not significantly degraded by exposure to the FLR. This stability may be due to the highly ordered packing of the alkyl chains in the monolayer of Ti-11-hydroxyundecylphosphonate which makes ether group —C—H bond abstraction sterically difficult; such abstraction processes are believed to involve oxygen-stabilized intermediate radicals, which may not be conformationally accessible in the tightly packed film.

Example 39

Hydrolytic Stability of Modified Titanium Surfaces

For a surface modification technique to be viable for use in vivo, the interface must be stable to hydrolysis under physiological conditions. Current technologies using siloxanes are limited: siloxane derivatized surfaces are hydrolytically labile. Instability of the surface results in desorption of the biomolecules from the surface, which may have deleterious effects in vivo. It has been shown that in vivo tests of titanium surfaces merely coated with bone morphogenic protein-2 (BMP-2) result in encapsulation of the surface by fibrous tissue, which is then coated in bone. It is postulated that desorption from the surface leads to the observed encapsulation. Thus, stable covalent attachment of the drug releasing agent to the surface is believed to be important. The hydrolytic stability of phosphonate interfaces on TiO$_2$ and ZrO$_2$ powders have been studied at neutral pH. It was demonstrated that over the course of one week, 16% of bound octadecylphosphonic acid was lost from the surface of TiO$_2$ and 5% of bound material was lost from the surface of ZrO$_2$, while powders coated with octadecyldimethylchlorosilane showed almost total surface hydrolysis over the course of one week.

To further test the stability of diphosphonate SAMs towards aqueous conditions, fluorimetry was employed. Coupons of Ti-mPEG were then exposed to vapor of DANSYL chloride to yield the surface-bound complex. The complex modified coupons were then treated with a solution of 6-maleimidohexanoic acid in THF and were then rinsed thoroughly, and analyzed via IR ($v_{CO}\approx 1705$ cm$^{-1}$). The coupons were then placed in a solution of N-(5-dimethylamino-1-naphthyl-sulfonyl)-RGDC (DANSYL-RGDC), then rinsed thoroughly, and probed via IR ($v_{peptide-CO}\approx 1650$-$1690$ cm$^{-1}$). The DANSYL group provides a fluorescent "tag" with which to monitor hydrolysis of the surface.

Figure 4A:
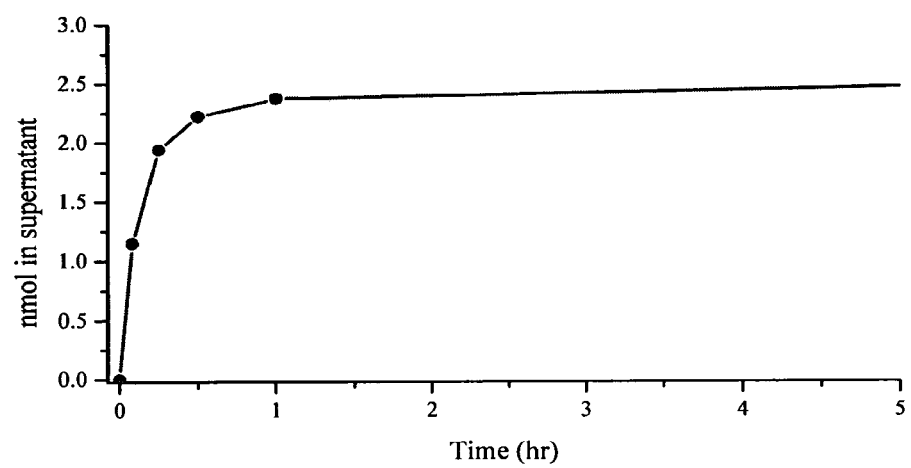
FIGS. 4(a) and 4(b) show plots of nanomoles of supernatant versus time, representing hydrolysis of DANSYL-RGDC from a layered phosphonic acid film over Figure (a) 5 hours, and Figure (b) over 96 hours followed by hydrolysis.
Figure 4B:
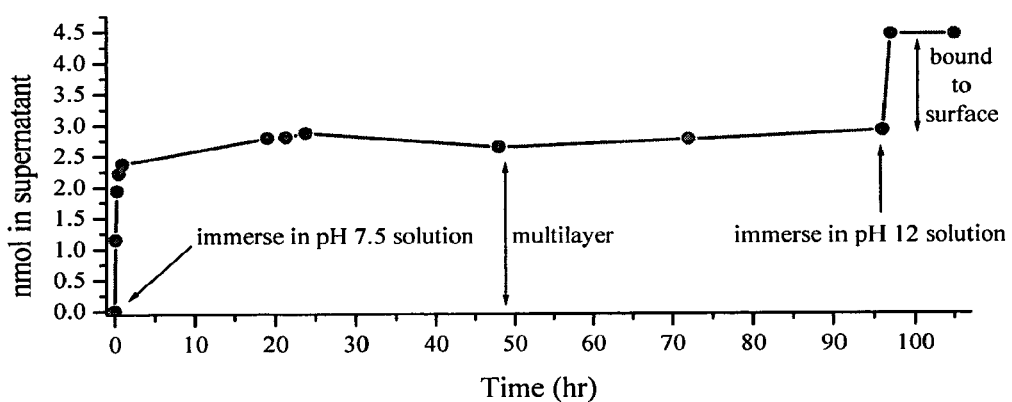

Fluorophore-labeled coupons were immersed in water at about pH 7.5. Fluorescence intensity of the supernatant was measured over about 90 hours; a calibration curve of DANSYL-RGDC was also prepared to relate concentrations in solution with fluorescence intensity, according to Beer's Law. After about 96 hours, the coupons were exposed to a strongly alkaline solution (about pH 12) to completely hydrolyze any remaining zirconium complex from their surface. Fluorescence intensity in the supernatant was measured against a second calibration curve of DANSYL-RGDC at about pH 12, and the solution concentration was determined by Beer's Law. In this way it was shown that the phosphonate film has long term hydrolytic stability at about pH 7.5. During the first 90 minutes, desorption of multilayered peptide occurs. Following the first 90 minutes, little further desorption occurred, even over about 4 days (see FIGS. 4(a) and 4(b)). At this point, the DANSYL-RGDC remaining on the surface was measured by exposing the coupon to strong alkaline (about pH 12) for about 3 hours to cleave any remaining zirconium complex species from the SAM. After this treatment, the fluorescence intensity of the supernatant increased dramatically. Analysis showed the surface loading of DANSYL-RGDC stable at about pH 7.5 to be about 0.58 nmol/cm$^2$ (the surface area of the coupon was about 2.65 cm$^2$). This value is similar to RGDC loadings on SAMs of 11-hydroxyphosphonate on Ti (~0.52 nmol/cm$^2$). Thus, the diphosphonate layered system, for every link of the chain, is stable to aqueous conditions over the long term, which is essential for use in biomaterials.

Example 40

X-Ray Photoelectron Spectroscopy (XPS) of Modified Titanium Surfaces

X-ray photoelectron spectroscopy (XPS) is a powerful technique to analyze the chemical composition of a surface, and XPS spectra of phosphonates bound to the surfaces of various oxides have been measured. In cases involving alkylphos-phonates bound to tantalum or titanium oxides, a single P(2p) signal was detected, evidence of a single phosphorus species on the surface, the surface-bound phosphonate. SAMs of Ti-12-phosphonododecylphosphonate were also investigated via XPS which revealed P(2s)≈192.0 eV with a shoulder at 193.3 eV (the P[2s] signal was analyzed instead of P[2p] due to the inability to resolve P[2p$_{1/2}$] and P[2p] of either a surface bound or free phosphonate). The peak at lower binding energy is indicative of a free phosphonic acid (c.f. the diphosphonic acid powder). The shoulder at higher binding energy is indicative of a surface-bound phosphonate (c.f.~192.5 eV based on bona fide Ti-Phosphate film). The difference in the measured intensities of the two phosphorus species is attributed to the escape depth-based sensitivities of the surface bound species which attenuates the signal of the surface bound phosphorus photoelectron.

Example 41

Figure 5:
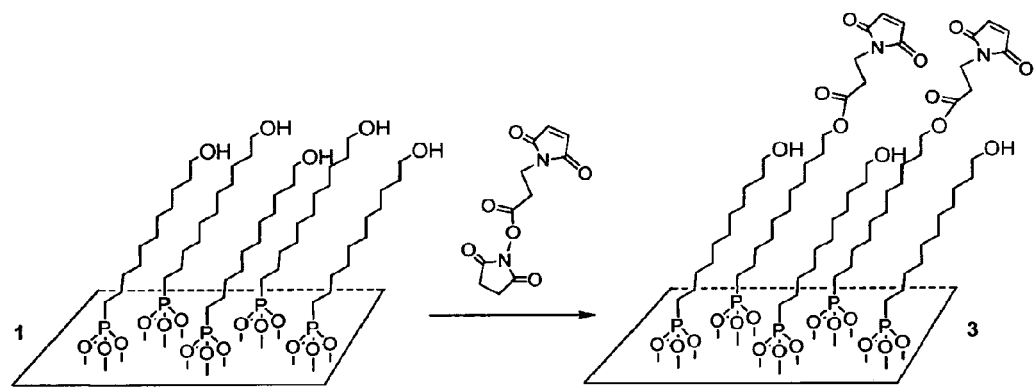
FIG. 5 shows self-assembled monolayer phosphorus-containing films derivatized to give a maleimido "tail" group, which can add cysteine-SH or lysine-$NH_2$ groups.

Mixed Speciation Self Assembled Monolayers of Phosphonates (SAMP) With compositional and spatial control: patterning In this embodiment of the invention, a basic SAMP coating is functionalized with a maleimido coupling reagent to give 3 as shown in FIG. 5.

The water wetting contact angle for 3 is ~70° (the surface does not completely wet), and dithiothreitol (DTT) is water soluble, so an aqueous solution of DTT will not spread out on the surface of 3. Stamping DTT from aqueous media onto 3 is done using masking or microcontact printing to lay down a pattern of DTT on the micron scale (sub-cellular dimension). The mask is then removed and the DTT-patterned surface is treated derivatized with desirable species.

Figure 6:
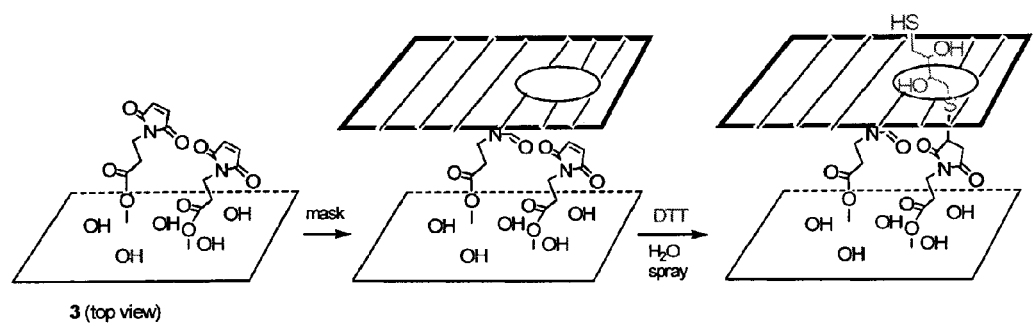
FIG. 6 shows a simple pattern formed by masking the maleimido-derivatized SAMP and adding an aqueous solution of dithiothreitol to it through holes in the mask.

To verify the patterning, the surface is treated first with DANSYL-RGDC (fluoresces green) and then with maleimido-derivatized ALEXA-FLUOR®-cadaverine. Then the printed peptides may be visualized by fluorescence microscopy to verify congruence between the printed and designed patterns. See FIG. 6.

It will be understood that this method allows for essentially unlimited spacial variation of surface patterning with peptides or other organic species by varying the pattern and size of holes in the mask. It will be further understood that the gaps in the mask may be any type of shape or combination of shapes.

Example 42

Hip Implant

Figure 7:
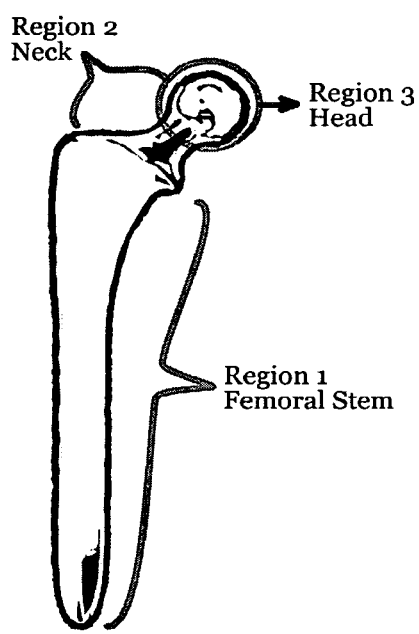
FIG. 7 shows regions of a hip implant with different surface properties and functionality.
Figure 8:
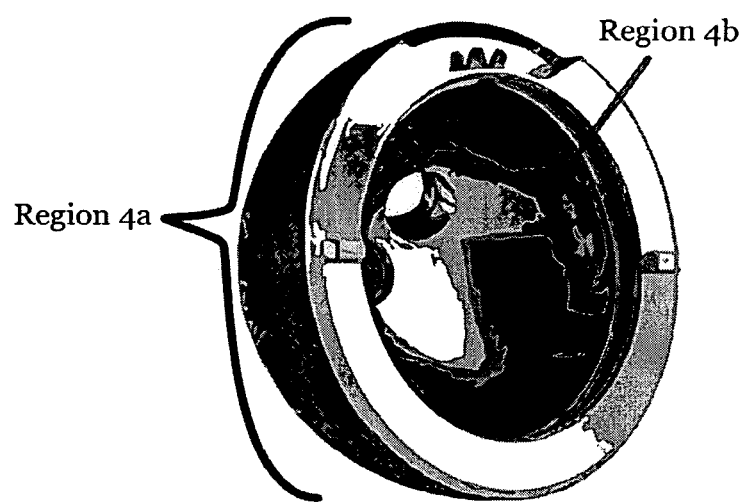
FIG. 8 shows the acetabular cup with its convex surface (Region 9a) and its convex surface (Region 9b)

The surface of a surgically implanted artificial hip encounters multiple environments for which different surface properties and functionality is desirable. These areas where different surface environments exist, as shown in FIGS. 7 and 8 are: The femoral stem (Region 1); the neck (Region 2); the head (Region 3); the interior surface of the acetabular cup (Region 4a) and the exterior surface of the acetabular cup (Region 4b). The surface environment and desirable properties for each of these regions are described below.

Region 1—When implanted, the surface of the femoral stem is placed in contact with the bone and marrow of the femur. For this surface, cell specific adhesion of osteoblasts is desirable to promote osteoconductivity and enable rapid and strong fixation between the native bone and the femoral stem surface.

Region 2—The neck of the implant connects the femoral stem to the head. The neck does not contact bone or metal, but rather muscle and blood. As such, desirable surface properties for the neck are resistance to corrosion, cell non-adherence or anti-inflammation.

Region 3—The ball or head of a hip implant sits against the interior surface of the acetabular cup. To enable movement of the leg, these surfaces should freely move against one another. For these surfaces, osteoconductivity is not desirable. Rather, the ideal surface will resist wear and abrasion and provide lubrication for the interface between the ball and acetabular cup.

Region 4—The acetabular cup contacts bone on its exterior convex surface (Region 4a) and the head of the hip stem on its interior convex surface (Region 4b). In some cases, a lining surface is placed on the interior surface of the acetabular cup. This lining may be ceramic or ultra-high molecular weight polyethylene. Therefore, the ideal surface properties for Region 4a are the same as for Region 1 and the ideal surface properties for region 4b are the same as for Region 3.

In one embodiment of the invention, Region 1 and Region 4a of a titanium hip implant are coated with phosphonoundecanol to which an osteoconductive molecule such as a peptide containing the RGD moiety is attached. Region 2 is coated with underivatized 11-hydroxyundecylphosphonate to prevent leaching of metals. Regions 3 and 4b are coated with octadecylphosphonic acid to lubricate the interface between the ball and interior surface of the acetabular cup and to minimize wear debris generated from abrasion at the interface between the surfaces.

In another embodiment, Region 2 is coated with an anti-infective.

TABLE 7

| Embodiment | Region | Desired Property | Coating |
|---|---|---|---|
| 1 | 1, 4a | Osteoconduction | 11-hydroxyundecylphosphonate - RGDC |
|  | 2 | Anti-corrosion | 11-hydroxyundecylphosphonate |
|  | 3, 4b | Resistance to wear & lubrication | octadeclphosphonic acid |
| 2 | 1, 4a | Osteoconduction | 11-hydroxyundecylphosphonate - RGDC |

TABLE 7-continued

| Embodiment | Region | Desired Property | Coating |
|---|---|---|---|
| | 2 | Anti-infection/anti-microbial | 11-hydroxyundecylphosphonate - anti-microbial |
| | 3, 4b | Resistance to wear & lubrication | octadecyl phosphonic acid |

Example 43

Thickness Calculations for Phosphonate Coatings

The phosphonate coatings may be covalently bound to the coated substrate via a mono-dentate, bi-dentate or tri-dentate bound phosphonate. The thickness of the coating ranges from about 0.3 nm to at least about 100 nm depending on the length of the R group bound to the phosphonic acid having the formula $H_2RPO_3$. Actual ranges and values of coating thicknesses depend on the type or content of the R groups of the phosphonate coating and include coating thicknesses of about 0.3 nm to about 1.0 nm, about 1.0 nm to about 1.6 nm, about 1.6 nm, about 1.5 nm to about 2.2 nm, about 2.0 nm, about 2.2 nm, about 2.2 nm to about 4.0 nm, about 2.5 nm to about 5.0 nm, about 2.8 nm, about 3.0 nm to about 10.0 nm, about 6.0 nm, about 5 nm to 100 nm.

Example coating thicknesses are presented in Table 8. Thicknesses were calculated in both solution and gas phase using Chem3D and Gaussian minimizations, assuming a 33° tilt angle for bi-dentate phosphonate coatings. The example coatings in Table 8 are for illustrative purposes and do not define or limit the scope of the invention. In addition, one of ordinary skill in the art will appreciate that similar calculations can be made for phosphonate coatings not list in Table 8 and will further appreciate that the coating thickness may vary as a function of the solvent and the number of phosphonate bonds (mono- bi- or tri-dentate).

TABLE 8

Phosphonate Coating Thicknesses

| Phosphonic Acid | Thickness (nm) |
|---|---|
| $H_2RPO_3$ where R is an alkylene or arylene hydrocarbon ligand comprising between about 1 and 6 carbon atoms | About 0.3-1.0 |
| $H_2RPO_3$ where R is an alkylene or arylene hydrocarbon ligand comprising between about 7 and 12 carbon atoms. | About 1.0-1.6 |
| 11-hydroxyundecylphosphonic acid | 1.6 |
| $H_2RPO_3$ where R is an alkylene or arylene hydrocarbon ligand comprising between about 13 and 18 carbon atoms | About 1.5-2.2 |
| 11-hydroxyundecylphosphonic acid - maleimide | 2.0 |
| Octadecyl phosphonic acid | 2.2 |
| $H_2RPO_3$ where R is an alkylene or arylene hydrocarbon ligand comprising between about 19 and 40 carbon atoms | About 2.2-4.0 |
| $H_2RPO_3$ where R contains a peptide or poly-petide. | About 2.5-5.0 |
| 11-hydroxyundecylphosphonic acid - maleimide - RGDC | 2.8 |
| $H_2RPO_3$ where R is a functional group (e.g 11-hydroxyundecylphosphonic acid) linked to a globular peptide or protein via maleimide or other peptide linker. | About 3.0-10.0 |
| $H_2RPO_3$ where R contains a globular peptide or protein | About 3.0-10.0 |
| 11-hydroxyundecylphosphonic acid - maleimide - IgG | About 6.0 |
| $H_2RPO_3$ where R contains a polymer | About 5-100 |
| 11-hydroxyundecylphosphonic acid - methyl-terminated poly(ethylene glycol) | About 100 |

Example 44

In-Vivo Osteoconductivity of RGD-Phosphonate-Functionalized Implants

Stable osteoconductive surfaces are desirable on orthopedic implants. An in-vivo study was conducted to assess the stability and osteoconductivity of a functionalized phosphonate coated orthopedic implant surface.

Sixty-two male Sprague-Dawley rats (Harlan, Ind., USA), 12 weeks of age with an average mass of 382±41 grams (range 285 to 466 grams), were bilaterally implanted in the femoral medullary canal of the femur. An RGDC/Au-functionalized smooth titanium implant (15.0 mm×1.6 mm), which served as control, was implanted in one femur and an RGD-SAMP functionalized smooth titanium implant prepared according to the present invention was implanted in the contralateral femur.

Titanium alloy (Ti—6Al—4V) rods, 1.6 mm in diameter, were hand-sanded using sand paper coated with 240, 500, 800, and 1200 grit SiC. For the control group (RGDC/Au), the rods were washed with sonication in dichloromethane (30 minutes), then methyl ethyl ketone (30 minutes), and then methanol (three 15 minute intervals). They were then coated using an Edwards Coating System at reduced pressure. A layer of chromium (~100 Å) was deposited, followed by a layer of gold (~1000 Å). Thickness of the deposited layers was monitored using a QCM crystal located within the evaporating chamber. The rods were, then cut into 15.0 mm pins and cleaned by washing with sonication in acetone (45 minutes), followed by the solvent washing regimen as described above. After solvent cleaning, all samples were placed in an oven at 120° C. for at least an hour or until needed. Following, the pins were immersed in a 0.5 mM solution of RGDC-peptide (Arg-Gly-Asp-Cys) in MilliQ water with final solution pH of 6.5. Containers were covered, and the pins were allowed to react with the RGDC for twenty-four hours with stirring. The pins were then rinsed briefly with sonication in MilliQ water and were blown dry with nitrogen.

For the experimental group (RGD/SAMP), the rods were first cut into 15.0 mm pins. The pins were cleaned by washing with sonication in acetone (45 minutes), then by the solvent washing regime as described above. All samples were placed in an oven at 120° C. for at least an hour. Following, the pins were suspended in a 0.1 mM solution of 11-hydroxyundecylphosphonic acid (PUL) in THF. The solvent was allowed to evaporate at room temperature until its level was below that of the ends of the suspended pins. The pins were then heated in a gravity convection oven at ~130° C. for 48 hours to bond the self-assembled monolayer of the phosphonate. The pins were rinsed with sonication in methanol for 30 minutes to remove any unbound material and were then blown dry with nitrogen. The Ti-PUL pins were immersed in a 0.5 mM solution of 3-maleimidopropionic acid N-hydroxysuccinimide ester (MAL) in dry acetonitrile and were stirred under nitrogen for 24 hours. They were rinsed with acetonitrile, briefly with sonication, to remove any residual uncoupled MAL and were then blown dry with nitrogen. Then the Ti-PUL-MAL pins were immersed in a solution of RGDC, following the same procedure as described above for the control pins.

After coating, all pins were sterilized with ethylene-oxide (ETO) at 55° C. for a period of 3 hours after which they were kept in a stove for 10.5 hours to let the excess ETO fade off. The pins were stored at room temperature.

Postoperative, immediate weight bearing was allowed. No complications were encountered, and no animals were eliminated for reasons of well-being. The animals were also administered bone fluorochromes, i.e., calcium chelators, over 2 distinct time periods. Calcein (20 mg/kg) and tetracycline-HCL (20 mg/kg) were administered subcutaneously at a perivascular location at base of the tail to enable calculations of bone formation and mineralization rates. Interlabeling periods were 7, 6 and 11 days, for the 2, 4 and 8-week groups respectively. Twenty rats were sacrificed at two, four and eight weeks after pin implantation for biomechanical testing (n=10 at each time point) and histomorphometrical analysis (n=10 at each time point). The femora were harvested and cleaned of soft tissue. The specimens were preserved by immersion in 70% ethanol, sectioned, and stained.

Histomorphometric analysis demonstrated that the RGD-SAMP functionalized implants showed improved osteoconduction, bone thickness and implant surface mineralization, particularly at the early 2 week time point. At 8-weeks post-implantation bone thickness increased 3.3-fold with the SAMP-coated pins ($p<0.001$) and 1.9-fold with the control pins ($p<0.05$) compared to the 4-week time point. Also, mineralizing surface had a 1.6-fold increase with the SAMP-coated pins ($p<0.05$) and a 2.2-fold increase with the control pins ($p<0.005$) compared to 4-weeks post-implantation.

Figure 9A:
FIGS. 9(a) and 9(b) show a comparison of in-vivo osteoconductivity and bone structure at 2 weeks on an implanted material functionalized with RGD according to the present invention (FIG. 9(a)) and functionalized with RGD via a thiol gold linker (FIG. 9(b))
Figure 9B:
Figure 10:
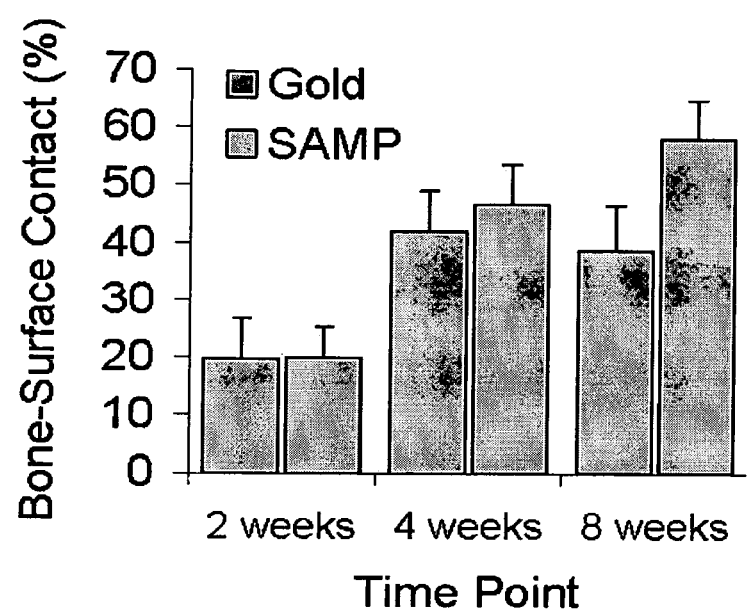
FIG. 10 shows a plot of percent bone surface coverage of an implant versus time at 2, 4 and 8 weeks.

Percentages of bone volume and bone-to-pin contact were significantly affected by the pin coating. The bone volume was significantly greater in the SAMP-coated pin at the 2 week time point ($p<0.05$) but not for later time points (FIGS. 9(a) and 9(b)). The percentage of pin surface covered by bone was also significantly greater with the SAMP-coating compared to control at the 8-week time point, but not earlier time points (FIG. 10). The percentage of bone volume decreased significantly by 8 weeks with the SAMP-coated pins, while bone volume increased significantly with the control pins by 4 weeks with a non-significant tendency to decrease again by 8 weeks.

The histomorphometrical data suggest there is more active bone remodeling occurring with the SAMP-platform than with the conventional gold platform and there is significant effect of time on the thickness of the layer of newly formed bone. There is a greater amount of bone, albeit woven, present after 2 weeks with the SAMP-platform than with the gold platform. This highly trabecularized bone, albeit poor in quality, was more frequently localized at the ends of the pin, either proximal, distal or both. This greater amount of bone at 2 weeks suggests there is increased promotion of attachment and/or activity of osteoblasts with the SAMP-platform. However, this increased amount of bone is resorbed away by 4 and 8 weeks. Present at 4 and 8 weeks are isolated bone trabeculae aligned parallel and adjacent to the area previously occupied by the pin. The reduction in trabecular density (i.e. number) with time confirms a loss in connectivity and the absence of bone bridging beyond the 2-week time point. There is nonetheless a greater amount of bone in contact with pins with the SAMP-platform compared to the gold platform at 8-weeks time.

Although the present invention is described with reference to certain preferred embodiments, it is apparent that modification and variations thereof may be made by those skilled in the art without departing from the spirit and scope of this invention as defined by the appended claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of materials, methods, and components otherwise used in the practice of the invention, which are particularly adapted to specific environments and operative requirements without departing from the principles of the present invention. The presently disclosed embodiments and examples are therefore to be considered in all respects as illustrative and not restrictive, the scope of the invention being indicated by the appended claims, and not limited to the foregoing description.

The disclosures of all patents and publications mentioned herein are hereby incorporated by reference in their entirety.

What is claimed is:

1. A device comprising:
   (i) a substrate comprising an oxide surface;
   (ii) a coating comprising a plurality of organophosphonate moieties covalently bonded to the oxide surface of the substrate; and
   (iii) an anti-infective compound directly attached to said organophosphonate moieties via a reactive functional group on the organophosphonate organo moieties, which reactive functional group is selected from the group consisting of hydroxyl, carboxylic acid, carboxylic ester, amino, thiol, phosphonic acid, phosphoric acid, sulfonic acid, and combinations of two or more thereof, and which reacts directly with said anti-infective compound to form a covalent bond.

2. The device of claim 1, wherein said coating exhibits one or more of the following characteristics:
   (a) the surface phosphorus-containing group density of the coated regions of said substrate is in the range of about 0.1 nmol/cm$^2$ to about 1.5 nmol/cm$^2$;
   (b) the phosphorus-based coating has a thickness of less than about 100 nm; or
   (c) the surface phosphorus-containing group density of the coated regions of said substrate is equal to or greater than the surface hydroxyl group density of the oxide surface of said substrate.

3. A device of claim 2, wherein said substrate comprises a medical device or an implantable device and wherein said native oxide surface comprises a metal surface selected from the group consisting of titanium, titanium alloys, stainless steel, stainless steel alloys, tantalum, silicon, cobalt-chromium and cobalt-chromium alloys.

4. The device of claim 1, wherein said oxide surface comprises a native oxide surface.

5. The device of claim 4, wherein said native oxide surface comprises a metal surface selected from the group consisting of titanium, titanium alloys, stainless steel, stainless steel alloys, tantalum, silicon, cobalt-chromium and cobalt-chromium alloys.

6. The device of claim 4, wherein the coating comprising a phosphonate monolayer covalently attached to the native oxide surface, wherein said phosphonate monolayer comprises quaternary alkylammonium moieties which are remote to the phosphonate groups.

7. The device of claim 6, wherein the native oxide surface comprises a metal.

8. The device of claim 1, wherein said coating has a thickness of less than about 10 nm.

9. The device of claim 1, wherein said anti-infective compound is selected from the group consisting of antimicrobials, antiseptics and antibiotics.

10. The device of claim 9, wherein said anti-infective compound comprises an antiseptic compound selected from the group consisting of chlorhexidine acetate, chlorhexidine, Gentian violet, octenidine, povidone iodine, quaternary ammonium compounds, silver sulfadiazine, triclosan, analogs thereof, derivatives thereof and salts thereof.

11. The device of claim 9, wherein said anti-infective compound comprises an antimicrobial compound selected from the group consisting of taurolidine, triclosan, aminoglycosides, nitrofurantoin, Antiamebics, Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Diphetarsone, Emetine, Fumagillin, Glaucarubin, Glycobiarsol, 8-Hydroxy-7-iodo-5-quinoline-sulfonic Acid, Iodochlorhydroxyquin, Iodoquinol, Paromomycin, Phanquinone, Polybenzarsol, Propamidine, Quinfamide, Scenidazole, Sulfarside, Teclozan, Tetracycline, Thiocarbamizine, Thiocarbarsone, Tinidazole; benzalkonium chloride, nitrofurazone, nystatin, sulfacetamide, clotrimazole; 2,4-Diaminopyrimidines, Brodimoprim, Textroxoprim, Trimethoprim; Nitrofurans, Furaltadone, Furazolium Chloride, Nifuradene, Nifuratel, Nifurfoline, Nifurpirinol, Nifurprazine, Nifurtoinol, Nitrofirantoin; Quinolones, Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nadilixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin; Sulfonamides, Acetyl Sulfamethoxpyrazine, Benzylsulfamide, Chloramine-B, Chloramine-T, Dichloramine T, N2-Formyl-sulfisomidine, N4-D-Glucosylsulfanilamide, Mafenide, 4'-(Methylsulfamoyl)sulfanilanilide, Noprylsulfainide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, 4-Sulfanilamidosalicylic Acid, N4-Sulfanilylsulfanilamide, Sulfanilylurea, N-Sulfanilyl-3, 4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole; Sulfones, Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, Sulfoxone Sodium, Thiazolsulfone; Clofoctol, Hexedine, Methenamine, Methenamine Anhydromethylenecitrate, Methenamine Hippurate, Methenamine Mandelate, Methenamine Sulfosalicylate, Nitroxoline, Taurolidine, Xibomol; leprostatic antibacterials, Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium; Allylamines Butenafine, Naftifine, Terbinafine, Imidazoles, Bifonazole, Butoconazole, Cholordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole Nitrate, Sertaconazole, Sulconazole, Tioconazole, Thiocarbamates, Tolcilate, Tolindate, Tolnaftate; Triazoles, Fluconazole, Itraconazole, Saperconazole, Terconazole; Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole Dihydrochloride, Exalamide, Flucytosine, Halethazole, Hexetidine, Loflucarban, Nifuratel, Propionic Acid, Pyrithione, Salicylanilide, Sodium Propionate, Sulbentine, Tenonitrozole, Triacetin, Ujothion, Undecylenic Acid, Zinc Propionate, derivatives thereof; salts thereof; and combinations thereof.

12. The device of claim 9, wherein said anti-infective compound comprises an antibiotic compound selected from the group consisting of Amino-glycosides, Amikacin, Apramycin, Arbekacin, Bambermycins, Butirosin, Dibekacin, Dihydrostreptomycin, Fortimicin, Gentamicin, Isepamicin, Kaniamycin, Micronomicin, Neomycin, Neomycin Undecylenate, Netilmicin, Paromomycin, Ribostamycin, Sisomicin, Spectinomycin, Streptomycin, Tobramycin, Trospectomycin; Amphenicols, Azidamfenicol, Chloramphenicol, Florfenicol, Thiamphenicol; Ansamycins, Rifamide, Rifampin, Rifamycin, Rifapentine, Rifaximin; beta-Lactams, Carbacephems, Loracarbef, Carbapenems, Biapenem, Imipenem, Meropenem, Panipenem; Cephalosporins, Cefaclor, Cefadroxil, Cefamandole, Cefatrizine, Cefazedone, Cefazolin, Cefcapene Povoxil, Cefclidin, Cefdinir, Cefditoren, Cefepime Cefetamet, Cefixime, Cefinenoxine, Cefodizime, Cefonicid, Cefoperazone, Ceforanide, Cefotaxime, Cefotiam, Cefozopran, Cefpimizole, Cefpiramide, Cefpirome, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin; Cephamycins, Cefbuperazone, Cefmetazole, Cefminox, Cefotetan, Cefoxitin; Monobactams, Aztreonam, Carumonam, Tigemonam; Oxacephens, Flomoxef, Moxalactam; Penicillins, Amdinocillin, Amdinocillin Pivoxil, Amoxicillin, Ampicillin, Apalcillin, Aspoxicillin, Azidocillin, Azlocillin, Bacampicillin, Benzylpenicillic Acid, Benzylpenicillin Sodium, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Naacillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicllin V Benzathine, Penicillin V Hydrabamine, Penimepicycline, Phenethicillin Potassium, Piperacillin, Pivampicillin, Propicillin, Quinacillin, Sulbenicillin, Sultamicillin, Talampicillin, Temocillin, Ticarcillin; Ritipenem, Lincosamides, Clindamycin, Lincomycin; Macrolides, Azithromycin, Capbomycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin; Polypeptides, Amphomycin, Bacitracin, Capreomycin, Colistin, Enduracidin, Enviomycin, Fusafungine, Gramicidin S, Gramicidin, Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin; Tetracyclines, Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Tetracycline; Cycloserine, Mupirocin, Tuberin; cefuroxime, ciprofloxacin, tobramycin, cefoperazone, erythromycin, gentamycin, cefuroxime/gentamicin; vancomycin; linezolid; bleomycin, dactinomycin, mitomycin; and fradiomycin sulfate.

13. The device of claim 1, wherein said substrate comprises an implantable substrate.

14. The device of claim 13, wherein said phosphorus-based coating comprises a surface phosphorus-containing group density of at least about 1.3 times the surface hydroxyl group density of the oxide surface of the implantable substrate.

15. The phosphorus-based coating of claim 13, wherein said phosphorus-based coating comprises a surface phosphorus-containing group density of at least about 2 times the surface hydroxyl group density of the oxide surface of the implantable substrate.

16. The device of claim 13, wherein said coating comprises a first, inner surface and a second, outer surface, said first, inner surface being defined by the organophosphonate moieties being covalently bonded to the oxide surface of the implantable substrate; and said second, outer surface exhibiting said anti-infective compound directly attached to the omega-positions of said organophosphonate organic moieties.

17. The device of claim 13, wherein the implantable substrate is selected from the group consisting of vascular devices, artificial hearts, heart assist devices, orthopedic devices, dental devices, drug delivery devices, ophthalmic devices, urological devices, catheters, neurological devices, neurostimulation devices, electrostimulation devices, electrosensing devices and synthetic prostheses.

18. The device of claim 17, wherein the implantable substrate is selected from the group consisting of vascular devices, artificial hearts, heart assist devices, orthopedic devices and dental devices.

19. The device of claim 18, wherein the implantable substrate is a dental device or an orthopedic device.

20. The device of claim 17 wherein:
(a) the phosphorus-based coating comprises a surface phosphorus-containing group density in the range of about 0.5 nmol/cm$^2$ to about 1.5 nmol/cm$^2$;
(b) the phosphorus-based coating has a thickness of less than about 10 nm; or
(c) the phosphorus-based coating comprises a surface phosphorus-containing group density of at least about 1.3 times the surface hydroxyl group density of the oxide surface of the implantable substrate.

21. The device of claim 17, wherein the implantable substrate comprise a metal.

22. The device of claim 21, wherein said metal comprises titanium or an alloy thereof.

23. The device of claim 17, wherein the implantable substrate is a vascular device and is selected from the group consisting of grafts, stents, stent grafts, catheters, valves, artificial hearts and pacemakers.

24. The device of claim 17, wherein the implantable substrate is an orthopedic device and is selected from the group consisting of fracture repair devices and artificial tendons.

25. The device of claim 17, wherein the implantable substrate is a glaucoma drain shunt.

26. The device of claim 17, wherein the implantable substrate is a urological device and is selected from the group consisting of penile devices, sphincter devices, urethral devices, bladder devices and renal devices.

27. The device of claim 17, wherein the implantable substrate is a synthetic prosthesis and is selected from the group consisting of breast prostheses and artificial organs.

28. The device of claim 17, wherein the implantable substrate is selected from the group consisting of dialysis tubing, dialysis membranes, blood oxygenator tubing, blood oxygenator membranes, blood bags, sutures, membranes, cell culture devices, chromatographic support materials, biosensors, anastomotic connectors, surgical instruments, angioplasty balloons, wound drains, shunts, tubing, urethral inserts, blood oxygenator pumps, and wound tubing.

29. The device of claim 17, wherein the implantable substrate is an electrostimulation or neurostimulation device and is selected from the group consisting of electrical stimulation leads, brain tissue stimulators, central nerve stimulators, peripheral nerve stimulators, spinal cord nerve stimulators and sacral nerve stimulators.

\* \* \* \* \*